United States Patent
Gibbons

(10) Patent No.: US 12,398,262 B1
(45) Date of Patent: Aug. 26, 2025

(54) TRIBLOCK COPOLYMER-BASED CELL STABILIZATION AND FIXATION SYSTEM AND METHODS OF USE THEREOF

(71) Applicant: 10x Genomics, Inc., Pleasanton, CA (US)

(72) Inventor: Michael Gibbons, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 269 days.

(21) Appl. No.: 17/580,947

(22) Filed: Jan. 21, 2022

Related U.S. Application Data

(60) Provisional application No. 63/140,750, filed on Jan. 22, 2021.

(51) Int. Cl.
| | |
|---|---|
| *C08L 53/00* | (2006.01) |
| *A61K 47/60* | (2017.01) |
| *A61K 47/69* | (2017.01) |
| *C08G 65/329* | (2006.01) |
| *C08L 71/02* | (2006.01) |

(52) U.S. Cl.
CPC ............ *C08L 53/005* (2013.01); *A61K 47/60* (2017.08); *A61K 47/6907* (2017.08); *C08G 65/329* (2013.01); *C08L 71/02* (2013.01)

(58) Field of Classification Search
CPC ... A61K 47/6907; A61K 47/60; C08L 53/005; C08L 71/02; C08G 65/329
See application file for complete search history.

(56) References Cited

U.S. PATENT DOCUMENTS

| | | | |
|---|---|---|---|
| 4,124,638 | A | 11/1978 | Hansen |
| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 5,185,099 | A | 2/1993 | Delpuech et al. |
| 5,270,183 | A | 12/1993 | Corbett et al. |
| 5,478,893 | A | 12/1995 | Ghosh et al. |
| 5,512,462 | A | 4/1996 | Cheng |
| 5,736,330 | A | 4/1998 | Fulton |
| 5,756,334 | A | 5/1998 | Perler et al. |
| 5,846,719 | A | 12/1998 | Brenner et al. |

(Continued)

FOREIGN PATENT DOCUMENTS

| | | |
|---|---|---|
| EP | 1019496 B1 | 9/2004 |
| EP | 1841879 A2 | 10/2007 |

(Continued)

OTHER PUBLICATIONS

Hatakeyama et al. "Systemic delivery of SiRNA to tumors using a lipid nanoparticle containing a tumor-specific cleavable PEG-lipid" in Biomaterials 32 (2011) 4306-4316. (Year: 2011).*

(Continued)

*Primary Examiner* — Blessing M Fubara
(74) *Attorney, Agent, or Firm* — WILSON SONSINI GOODRICH & ROSATI

(57) ABSTRACT

Systems and methods are provided for stabilization of cells and retention of biomolecules therein for further analysis. Block copolymers are inserted into membranes of biological particles, cell membranes or organelles (e.g., organelle membranes) and polymerized to form an intra-biological particle (e.g., intracellular) polymer network.

22 Claims, 21 Drawing Sheets

(56) References Cited

U.S. PATENT DOCUMENTS

| | | |
|---|---|---|
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,265,552 B1 | 7/2001 | Schatz |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,264,929 B2 | 9/2007 | Rothberg et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,709,198 B2 | 5/2010 | Luo et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,604,182 B2 | 12/2013 | Luo et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,951,726 B2 | 2/2015 | Luo et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,727,810 B2 | 8/2017 | Fodor et al. |
| 9,764,322 B2 | 9/2017 | Hiddessen et al. |
| 9,783,841 B2 | 10/2017 | Nolan et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,002,316 B2 | 6/2018 | Fodor et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,480,022 B2 | 11/2019 | Chee |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,550,429 B2 | 2/2020 | Harada et al. |
| 10,557,158 B2 | 2/2020 | Hardenbol et al. |
| 10,590,244 B2 | 3/2020 | Delaney et al. |
| 10,724,078 B2 | 7/2020 | Van et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,920,183 B2 | 3/2024 | Bharadwaj et al. |
| 11,952,626 B2 | 4/2024 | Pfeiffer et al. |
| 12,065,688 B2 | 8/2024 | Bell |
| 12,084,715 B1 | 9/2024 | Lund |
| 12,163,179 B2 | 12/2024 | Bell et al. |
| 12,169,198 B2 | 12/2024 | Price et al. |
| 12,188,014 B1 | 1/2025 | Price et al. |
| 12,235,262 B1 | 2/2025 | Giresi |
| 2002/0005354 A1 | 1/2002 | Spence et al. |
| 2002/0051971 A1 | 5/2002 | Stuelpnagel et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |

(56) References Cited

U.S. PATENT DOCUMENTS

| | | |
|---|---|---|
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0010511 A1 | 1/2010 | Harris et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2013/0171621 A1 | 7/2013 | Luo et al. |
| 2014/0065234 A1 | 3/2014 | Shum et al. |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0000854 A1 | 1/2015 | Gann-Fetter et al. |
| 2015/0267191 A1 | 9/2015 | Steelman et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0108458 A1 | 4/2016 | Frei et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0016053 A1 | 1/2017 | Beechem et al. |
| 2017/0029875 A1 | 2/2017 | Zhang et al. |
| 2017/0067096 A1 | 3/2017 | Wassie et al. |
| 2017/0089811 A1 | 3/2017 | Tillberg et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0241911 A1 | 8/2017 | Rockel et al. |
| 2017/0260584 A1 | 9/2017 | Zheng et al. |
| 2018/0030515 A1 | 2/2018 | Regev et al. |
| 2018/0051322 A1 | 2/2018 | Church et al. |
| 2018/0080075 A1 | 3/2018 | Brenner et al. |
| 2018/0105808 A1 | 4/2018 | Mikkelsen et al. |
| 2018/0216161 A1 | 8/2018 | Chen et al. |
| 2018/0245142 A1 | 8/2018 | So et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0371545 A1 | 12/2018 | Wong et al. |
| 2019/0055594 A1 | 2/2019 | Samusik et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0127731 A1 | 5/2019 | McDermott |
| 2019/0134633 A1 | 5/2019 | Bharadwaj et al. |
| 2019/0161796 A1 | 5/2019 | Hauling et al. |
| 2019/0176152 A1 | 6/2019 | Bharadwaj et al. |
| 2019/0177800 A1 | 6/2019 | Boutet et al. |
| 2019/0194709 A1 | 6/2019 | Church et al. |
| 2019/0264268 A1 | 8/2019 | Frisen et al. |
| 2019/0314291 A1* | 10/2019 | Besin .................. A61K 39/245 |
| 2019/0323088 A1 | 10/2019 | Boutet et al. |
| 2019/0330617 A1 | 10/2019 | Church et al. |
| 2019/0345636 A1 | 11/2019 | McDermott et al. |
| 2019/0352717 A1 | 11/2019 | Schnall-Levin |
| 2019/0367969 A1 | 12/2019 | Belhocine et al. |
| 2019/0367997 A1 | 12/2019 | Bent et al. |
| 2019/0376118 A1 | 12/2019 | Belhocine et al. |
| 2020/0005902 A1 | 1/2020 | Mellen et al. |
| 2020/0024641 A1 | 1/2020 | Nolan et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0080136 A1 | 3/2020 | Zhang et al. |
| 2020/0105373 A1 | 4/2020 | Zheng |
| 2020/0224244 A1 | 7/2020 | Nilsson et al. |
| 2020/0239946 A1 | 7/2020 | Dewal |
| 2020/0256867 A1 | 8/2020 | Hennek et al. |
| 2020/0263232 A1 | 8/2020 | Bell et al. |
| 2020/0277663 A1 | 9/2020 | Ramachandran Iyer et al. |
| 2020/0291454 A1 | 9/2020 | Belhocine et al. |
| 2020/0407775 A1 | 12/2020 | Bharadwaj et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0190770 A1 | 6/2021 | Delaney et al. |
| 2021/0270703 A1 | 9/2021 | Abousoud |
| 2022/0162671 A1 | 5/2022 | Pfeiffer et al. |
| 2022/0403375 A1 | 12/2022 | Martinez |
| 2024/0002914 A1 | 1/2024 | Pfeiffer et al. |
| 2024/0272044 A1 | 8/2024 | Bava |

FOREIGN PATENT DOCUMENTS

| | | |
|---|---|---|
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |

(56) References Cited

FOREIGN PATENT DOCUMENTS

| | | |
|---|---|---|
| WO | WO-2001002850 A1 | 1/2001 |
| WO | WO-0114589 A2 | 3/2001 |
| WO | WO-0190418 A1 | 11/2001 |
| WO | WO-2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2014210353 A2 | 12/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016168584 A1 | 10/2016 |
| WO | WO-2017015075 A1 | 1/2017 |
| WO | WO-2017066231 A1 | 4/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018075693 A1 | 4/2018 |
| WO | WO-2018091676 A1 | 5/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165181 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020061108 A1 | 3/2020 |
| WO | WO-2020123320 A2 | 6/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020176788 A1 | 9/2020 |
| WO | WO-2020198532 A1 | 10/2020 |
| WO | WO-2021046475 A1 | 3/2021 |
| WO | WO-2021067514 A1 | 4/2021 |
| WO | WO-2021102005 A1 | 5/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023018799 A1 | 2/2023 |
| WO | WO-2023076528 A2 | 5/2023 |

OTHER PUBLICATIONS

10X Genomics, Inc. CG000153 Rev A. Chromium Single Cell DNA Reagent Kits User Guide. 2018.

10X Genomics, Inc. CG000184 Rev A. Chromium Single Cell 3' Reagent Kits v3 User Guide with Feature Barcoding Technology for CRISPR Screening. 2018.

10X Genomics, Inc. CG000185 Rev B. Chromium Single Cell 3' Reagent Kits User Guide with Feature Barcoding Technology for Cell Surface Protein. 2018.

10X Genomics, Inc. CG000208 Rev E. Chromium Next GEM Single Cell V(D)J reagent Kits v1.1 User Guide with Feature Barcode Technology for Cell Surface Protein. 2020.

10X Genomics, Inc. CG000209 Rev D. Chromium Next GEM Single Cell ATAC Reagent Kits v1.1 User Guide. 2020.

10X Genomics, Inc. CG000239 Rev B. Visium Spatial Gene Expression Reagent Kits User Guide. 2020.

10X Genomics, Inc. CG000239 Rev D. Visium Spatial Gene Expression Reagent Kits User Guide. Oct. 2020.

10X Genomics, Inc. CG00026. Chromium Single Cell 3' Reagent Kit User Guide. 2016.

10X Genomics, Inc. LIT00003 Rev B Chromium Genome Solution Application Note. 2017.

Abate, A.R. et al. "Beating Poisson encapsulation statistics using close-packed ordering" Lab on a Chip (2009 Sep. 21) 9(18):2628-2631.

Adamson et al., "Production of arrays of chemically distinct nanolitre plugs via repeated splitting in microfluidic devices", Lab Chip 6(9): 1178-1186 (Sep. 2006).

(56) References Cited

OTHER PUBLICATIONS

Agard et al. A Strain-Promoted [3 + 2] Azide-Alkyne Cycloaddition for Covalent Modification of Biomolecules in Living Systems. J Am Chem Soc 2004, 126, 46, 15046-15047.
Agasti, S.S. et al. "Photocleavable DNA barcode-antibody conjugates allow sensitive and multiplexed protein analysis in single cell" J Am Chem Soc (2012) 134(45):18499-18502.
Altschul et al. Basic local alignment search tool. J Mol Biol 215(3):403-410 (1990).
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Blackman et al. Tetrazine Ligation: Fast Bioconjugation Based on Inverse-Electron-Demand Diels-Alder Reactivity. J Am Chem Soc 2008, 130, 41, 13518-13519.
Braeckmans et al., Scanning the Code. Modern Drug Discovery. 2003:28-32.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chen, et al. Spatially resolved, highly multiplexed RNA profiling in single cells. Science. 348.6233 (2015).
Chien et al. "Multiport flow-control system for lab-on-a-chip microfluidic devices", Fresenius J. Anal Chem, 371:106-111 (Jul. 27, 2001).
Choi, et al., Recent advances in photo-crosslinkable hydrogels for biomedical applications. BioTechniques 66: 40-53 (Jan. 2019) 10.2144/btn-2018-0083.
Chu, et al. Controllable monodisperse multiple emulsions. Angew Chem Int Ed Engl. 2007;46(47):8970-4.
Clark, Sheila. Single cell RNA-seq: An introductory overview and tools for getting started. 10X Genomics—Blog. Sep. 6, 2022. 6 pages. https://www.10xgenomics.com/blog/single-cell-rna-seq-an-introductory-overview-and-tools-for-getting-started.
Clausell-Tormos et al., "Droplet-based microfluidic platforms for the encapsulation and screening of mammalian cells and multicellular organisms", Chem. Biol. 15:427-437 (2008).
Codelli et al. Second-Generation Difluorinated Cyclooctynes for Copper-Free Click Chemistry. J. Am. Chem. Soc. 2008. 130: 11486-11493.
Co-pending U.S. Appl. No. 16/434,076, inventor Giresi; Paul, filed on Jun. 6, 2019.
Co-pending U.S. Appl. No. 16/434,084, inventor Giresi; Paul, filed on Jun. 6, 2019.
Co-pending U.S. Appl. No. 16/434,102, inventors Price; Andrew D. et al., filed on Jun. 6, 2019.
Co-pending U.S. Appl. No. 16/737,762, inventors Price; Andrew D. et al., filed on Jan. 8, 2020.
Co-pending U.S. Appl. No. 16/737,770, inventors Belhocine; Zahara Kamila et al., filed on Jan. 8, 2020.
Co-pending U.S. Appl. No. 16/789,273, inventors Maheshwari; Arundhati Shamoni et al., filed on Feb. 12, 2020.
Co-pending U.S. Appl. No. 16/800,450, inventor Katherine; Pfeiffer, filed on Feb. 25, 2020.
Co-pending U.S. Appl. No. 17/014,909, inventor Giresi; Paul, filed on Sep. 8, 2020.
Co-pending U.S. Appl. No. 17/148,942, inventors Mcdermott; Geoffrey et al., filed on Jan. 14, 2021.
Co-pending U.S. Appl. No. 17/166,982, inventors Mcdermott; Geoffrey et al., filed on Feb. 3, 2021.
Co-pending U.S. Appl. No. 17/175,542, inventors Maheshwari; Arundhati Shamoni et al., filed on Feb. 12, 2021.
Co-pending U.S. Appl. No. 17/220,303, inventor Walter; Dagmar, filed on Apr. 1, 2021.
Co-pending U.S. Appl. No. 17/318,364, inventors Bava; Felice Alessio et al., filed on May 12, 2021.
Co-pending U.S. Appl. No. 17/381,612, inventor Martinez; Luigi Jhon Alvarado, filed on Jul. 21, 2021.
Co-pending U.S. Appl. No. 17/512,241, inventors Hill; Andrew John et al., filed on Oct. 27, 2021.
Co-pending U.S. Appl. No. 17/517,408, inventors Salmanzadeh; Alireza et al., filed on Nov. 2, 2021.
Co-pending U.S. Appl. No. 17/518,213, inventor Lund; Paul Eugene, filed on Nov. 3, 2021.
Co-pending U.S. Appl. No. 17/522,741, inventors Zheng; Xinying et al., filed on Nov. 9, 2021.
Co-pending U.S. Appl. No. 17/545,862, inventor Katherine; Pfeiffer, filed on Dec. 8, 2021.
Co-pending U.S. Appl. No. 17/573,350, inventor Corey; M. Nemec, filed on Jan. 11, 2022.
Co-pending U.S. Appl. No. 17/957,781, inventor Bava; Felice Alessio, filed on Sep. 30, 2022.
Co-pending U.S. Appl. No. 18/046,843, inventor Toh; Mckenzi, filed on Oct. 14, 2022.
Co-pending U.S. Appl. No. 18/152,650, inventor Shastry; Shankar, filed on Jan. 10, 2023.
Credle et al. Multiplexed analysis of fixed tissue RNA using Ligation in situ Hybridization. Nucleic Acids Research, 2017, vol. 45, No. 14, e128.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Deforest et al. Peptide-Functionalized Click Hydrogels with Independently Tunable Mechanics and Chemical Functionality for 3D Cell Culture. Chem. Mater 2010, 22, 4783-4790.
Deforest et al. Sequential Click Reactions for Synthesizing and Patterning 3D Cell Microenvironments. Nat Mater 2009; 8(8): 659-664.
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Echeverria et al. Functional Stimuli-Responsive Gels: Hydrogels and Microgels. Gels. 2018(4) 54. 37 pages.
Elbert et al. Protein delivery from materials formed by self-selective conjugate addition reactions. 2001. J Controlled Release 76: 11-25.
Esser-Kahn, et al. Triggered release from polymer capsules. Macromolecules. 2011; 44:5539-5553.
Fairbanks et al. A Versatile Synthetic Extracellular Matrix Mimic via Thiol-Norbornene Photopolymerization. Adv. Mater 2009; 21(48): 5005-5010.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Gao et al., Q&A: Expansion microscopy, BMC Biology vol. 15 Article 50; Published Jun. 19, 2017.

(56) References Cited

OTHER PUBLICATIONS

Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gupta et al., Single-cell isoform RNA sequencing characterizes isoforms in thousands of cerebellar cells. Nat Biotechnol vol. 36; pp. 1197-1202; Published: Oct. 15. 2018.
Gutsmiedl et al. Copper-Free "Click" Modification of DNA via Nitrile Oxide-Norbornene 1,3-Dipolar Cycloaddition. Org. Lett. 2009, 11, 11, 2405-2408.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Henikoff et al. Amino acid substitution matrices from protein blocks. PNAS USA 89(22):10915-10919 (1992).
Higgins, et al. Clustal: A Package for Performing Multiple Sequence Alignment on a Microcomputer. Gene. 73 (1988): 237-244.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hug, et al. Measurement of the No. of molecules of a single mRNA species in a complex mRNA preparation. J Theor Biol. Apr. 21, 2003;221(4):615-24.
Hughes, et al. Choose Your Label Wisely: Water-Soluble Fluorophores Often Interact with Lipid Bilayers. Dept. of Chem. 2014. Plos One. Feb. 4; 9(2):e87649.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(suppl5):4742.
Jewett, et al. Cu-free click cycloaddition reactions in chemical biology. Chem Soc Rev. Apr. 2010;39(4):1272-9.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karlin, et al. Applications and statistics for multiple high-scoring segments in molecular sequences. PNAS USA 90:5873-5877 (1993).
Kenis, et al. Microfabrication Inside Capillaries Using Multiphase Laminar Flow Patterning. Science. 1999; 285:83-85.
Kivioja, et al. Counting absolute Nos. of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chern. 8: 1110-1115 (2008).
Lagally, et al. Single-Molecular DNA Amplification and Analysis in an Integrated Microfluidic Device. Anal Chem. Feb. 1, 2001;73(3):565-70.
Lee et al. Fluorescent in situ sequencing (FISSEQ) of RNA for gene expression profiling in intact cells and issues. Nat Protoc. 2015; 10(3): 442-458.

Lennon et al. A scalable, fully automated process for construction of sequence-ready barcoded libraries for 454. Genome Biology 11:R15 (2010).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
Mccoy, R. et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009.
Navin. The first five years of single-cell cancer genomics and beyond. Genome Res. Oct. 2015;25(10):1499-507. doi: 10.1101/gr.191098.115.
Ning et al. Protein Modification by Strain-Promoted Alkyne-Nitrone Cycloaddition. Angewandte Chemie International Edition. 2010(49), 3065-3068.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidically generated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.
Pearson et al. Improved Tools for Biological Sequence Comparison. PNAS USA 85:2444-48 (1988).
Periyannan Rajeswari PK, et al. Multiple pathogen biomarker detection using an encoded bead array in droplet PCR. J Microbiol Methods. Aug. 2017;139:22-28. doi: 10.1016/j.mimet.2017.04.007. Epub Apr. 20, 2017. PMID: 28434824.
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Phelps et al. Maleimide cross-linked bioactive PEG hydrogel exhibits improved reaction kinetics and cross-linking for cell encapsulation and in-situ delivery. Adv Mater 2012; 24(1): 64-2.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Prescher, et al. Copper-free click chemistry for dynamic in vivo imaging. Proceedings of the National Academy of Sciences. 104 (2007): 16793-16797.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 27:847-850.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL: http://454.com/downloads/my454/documentation/technical-bulletins/TCB-09004 Using MultiplexIdentifierAdaptorsForTheGSFLXTitaniumSeriesChemistry-BasicMIDSet.pdf.

(56) References Cited

OTHER PUBLICATIONS

Rodriques, et al. Slide-seq: A scalable technology for measuring genome-wide expression at high spatial resolution. Science 363. 6434 (2019): 1463-1467.
Rotem, A. et al., "High-throughput single-cell labeling (Hi-SCL) for RNA-Seq using drop-based microfluidics" PLOS One (May 22, 2015) 0116328 (14 pages).
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Saxon et al., Cell surface engineering by a modified Staudinger reaction. Science. Mar. 17, 2000;287(5460):2007-10.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. Polymer. vol. 51, Issue 25, Nov. 26, 2010, pp. 5883-5889.
Seiffert, S et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Sletten et al. A Bioorthogonal Quadricyclane Ligation. Journal of the American Chemical Society 2011. 17570-17573.
Sletten, et al. Bioorthogonal chemistry: fishing for selectivity in a sea of functionality. Angew Chem Int Ed Engl. 2009;48(38):6974-98. doi: 10.1002/anie.200900942.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Stockmann et al. Exploring isonitrile-based click chemistry for ligation. Organic & Biomolecular Chemistry. Issue 21. 2011. 7303-7305.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)107-121.
Trejo et al., Extraction-free whole transcriptome gene expression analysis of FFPE sections and histology-directed subareas of tissue. PLoS ONE 14(2): e0212031; Feb. 22, 2019.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Van Berkel et al. Metal-Free Triazole Formation as a Tool for Bioconjugation. ChemBioChem 2007. 8(13): 1504-1508.

Visium Spatial Gene Expression Reagent Kits—Tissue Optimization User Guide, 10X Genomics, CG000238 Rev D, Oct. 2020.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Yarema et al. Metabolic delivery of ketone groups to sialic acid residues. Application To cell surface glycoform engineering. J Biol Chem 1998; 273(47): 31168-79.
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
Arslan, M., et al., "Polymer Nanocomposites via Click Chemistry Reactions", Polymers, 24 pages, Oct. 11, 2017.
Azagarsamy, M., et al., "Bioorthogonal Click Chemistry: An Indispensabe Tool to Create Multifaceted Cell Culture Scaffolds", American Chemical Society: ACS Macro Letters, 2013, 2, 5-9.
Elchinger, P., et al., "Polysaccharides: The "Click" Chemistry Impact", Polymers 2011, 3, 1607-1651.
Le Droumaguet, B., et al., "Click Chemistry: A Powerful Tool to Create Polymer-Based Macromolecular Chimeras", Macromolecular Journals, DOI: 10.1002/marc.200800155, 2008, 29, 1073-1089.
Leal-Egana, A., et al., "A simple non-destructive method for the fixation and immunostaining of cultured cells encapsulated in alignate", Biotechnol. Appl. Biochem (2006) 44, 143-150.
Li, J., et al., "Development and aplicaiton of bond cleavage reactions in bioorthogonal chemistry", Nature Chemical Biology, Perspective, vol. 12, Feb. 16, 2016.
Martindale, J., et al., "Uncoupling of increased cellular oxidative stress and myocardial ischemia reperfusion injury by directed sarcolemma stabilization", J Mol Cell Cardiol., Feb. 2014; 67: 26-37.
Moloughney, J., et al., "Poloxamer 188 (P188) as a Membrane Resealing Reagent in Biomedical Applications", National Institutes of Health, Recent Pat Biotechnol. Dec. 2012; 6(3): 200-211.
Patterson, D., et al., "Finding the Right (Bioorthogonal) Chemistry", ACS Chemical Biology, Mar. 2014, 9(3) 592-605.
Zou, Y., et al., "Click" chemistry in polymeric scaffolds: Bioactivbe materials for tissue engineering, Journal of Controlled Release 273 (2018) 160-179.
Co-pending U.S. Appl. No. 18/392,684, inventors Fernandes; Sunjay Jude et al., filed on Dec. 21, 2023.
Co-pending U.S. Appl. No. 18/743,583, inventor Nagendran; Monica, filed on Jun. 14, 2024.
Co-pending U.S. Appl. No. 18/795,976, inventors Meer; Elliott et al., filed on Aug. 6, 2024.
Co-pending U.S. Appl. No. 18/824,258, inventor Stott; Ryan Timothy, filed on Sep. 4, 2024.
Co-pending U.S. Appl. No. 18/959,351, inventor Schnall-Levin; Michael, filed on Nov. 25, 2024.
Co-pending U.S. Appl. No. 19/044,383, inventors Smibert; Peter et al., filed on Feb. 3, 2025.

\* cited by examiner

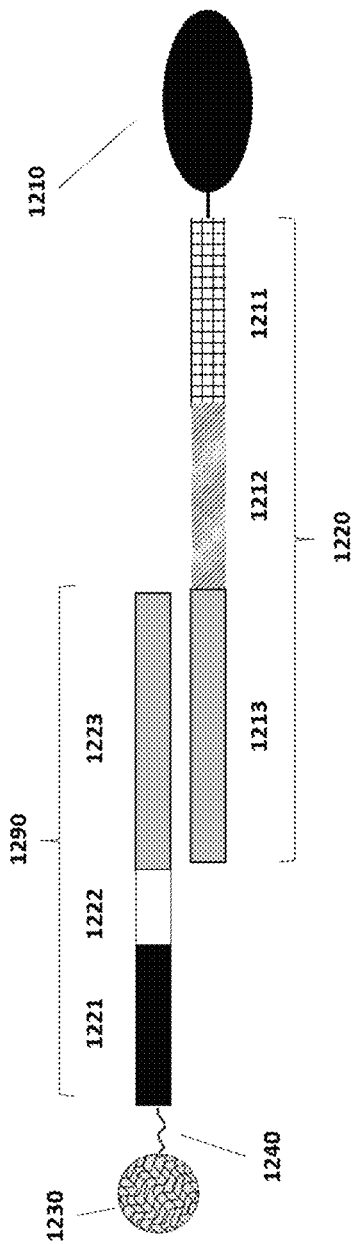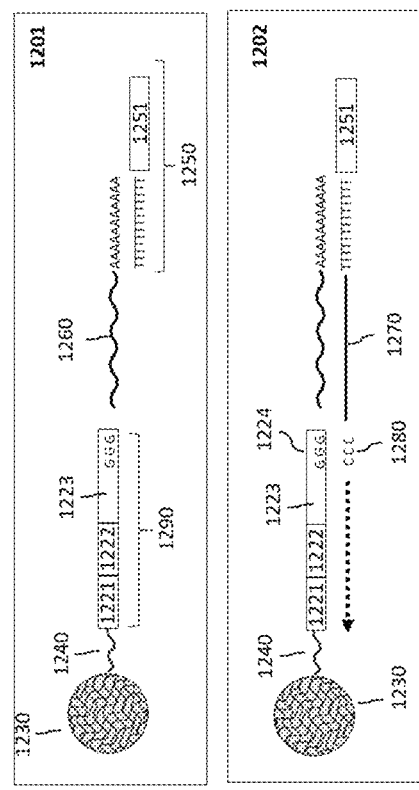
FIG. 11A
FIG. 11B

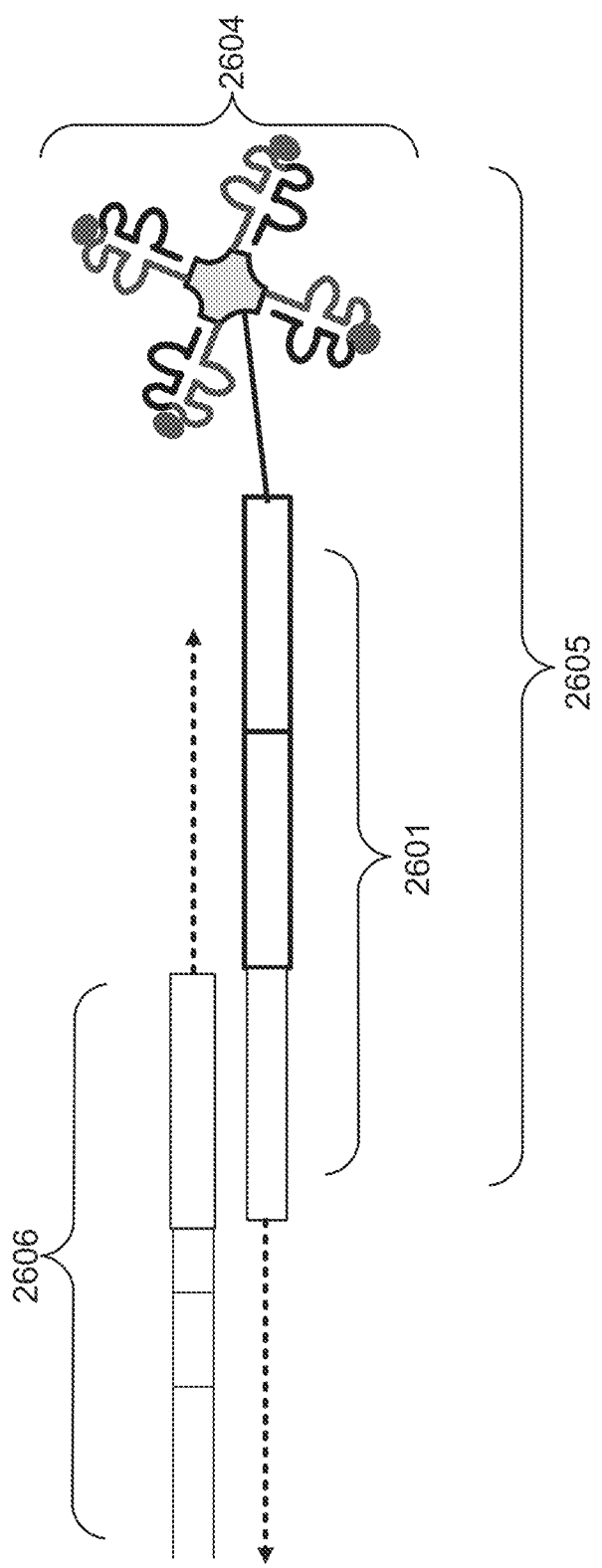

TRIBLOCK COPOLYMER-BASED CELL STABILIZATION AND FIXATION SYSTEM AND METHODS OF USE THEREOF

CROSS-REFERENCE TO RELATED APPLICATIONS

This application claims the benefit of U.S. Provisional Application No. 63/140,750, filed on Jan. 22, 2021, which is incorporated herein by reference in its entirety.

FIELD OF THE INVENTION

The invention relates to methods and systems for stabilization of cells, in particular formation of a cell-internal polymer network that retains biomolecules for analysis.

BACKGROUND

A major challenge in single cell analysis is the ability to perform assays after cell fixation. While the stability of biomolecules of interest (e.g., RNA, DNA, surface proteins) is important for both bulk cell and single cell analysis, a unique challenge in single cell analysis is biomolecule retention within each individual cell. Many solutions exist for stabilization of biomolecules in bulk (e.g., paraformaldehyde, methanol, and many commercial buffers that control pH, osmotic pressure, etc.), but these fixation methods have poor downstream compatibility with single cell RNA sequencing and other assays. One contributor to this problem is poor RNA retention and resulting high ambient RNA noise in sequencing data. Therefore, a method that reduces biomolecule escape from cells while remaining compatible with biomolecule stabilization/fixation and downstream single cell assays (such as single cell sequencing) would increase flexibility of sample collection, transportation and storage, while preserving or improving data quality and yield.

BRIEF SUMMARY OF THE INVENTION

Systems and methods are provided for stabilization of cells and preservation of biomolecules therein.

In one aspect, a block copolymer is provided. The block copolymer includes: a hydrophobic core region that has a first end and a second end; and first and second hydrophilic regions adjacent to the first and second ends of the hydrophobic core region, respectively, wherein the first hydrophilic region, and optionally the second hydrophilic region, comprises a bioorthogonal reactive moiety, wherein the hydrophobic region is capable of stable insertion into and retention within a cell membrane, and wherein when the hydrophobic region is inserted into a continuous cell membrane (i.e., with an extracellular side that faces the outside of a cell and an intracellular side that faces the inside of the cell), the first hydrophilic region and the bioorthogonal reactive moiety thereof are oriented on the intracellular side of the cell membrane and the second hydrophilic region of the block copolymer is oriented on the extracellular side of the cell membrane.

In one embodiment, the second hydrophilic region includes a bioorthogonal reactive moiety, which may be the same as or different from the bioorthogonal reactive moiety of the first hydrophilic region. In another embodiment, the second hydrophilic region of the block copolymer includes a cell membrane impermeable moiety, and when the hydrophobic region is inserted into the continuous cell membrane, the cell membrane impermeable moiety is oriented on the extracellular side of the cell membrane.

In some embodiments, the hydrophobic region of the block copolymer comprises or consists of poly(propylene oxide). In some embodiments, the first and/or second hydrophilic region of the block copolymer comprises or consists of poly(ethylene oxide). In some embodiments, the first hydrophilic region, and optionally the second hydrophilic region, of the block copolymer includes an alkyne group or an azide group bioorthogonal reactive moiety.

In some embodiments, the second hydrophilic region of the block copolymer includes a cell membrane impermeable moiety, which may include, for example, an affinity moiety and/or a detectable moiety. For example, in some embodiments, the cell membrane impermeable moiety may include a nanoparticle, a fluorophore, and/or a radiolabel. In some embodiments, the cell membrane impermeable moiety includes an affinity moiety, which may comprise or consist of a member of an affinity binding pair, such as, for example, avidin, streptavidin, biotin, digoxigenin, a lectin, a carbohydrate, a lipid, an antibody or antigen-binding fragment thereof, an oligonucleotide, a receptor, or a receptor ligand.

In another aspect, a system for cell stabilization is provided. The system includes: (i) a plurality of block copolymers as described herein; and (ii) a plurality of monomers or oligomers that are capable of accumulating within a cell and that comprises: a first bioorthogonal moiety that is capable of reacting with the bioorthogonal moiety of the first hydrophilic region of the block copolymer, and a second bioorthogonal moiety that is capable of reacting with the first bioorthogonal moiety (e.g., the bioorthogonal moieties are capable of reacting to form a stable covalent bond between a monomer and the first hydrophilic region, between monomers or oligomers), therefore polymerizing monomers or oligomers to form an internal polymer network within the cell, that is attached to the hydrophilic regions of a plurality of the block copolymers as membrane-bound anchors for the polymer network. The first bioorthogonal moiety of the monomers or oligomers may react with both the bioorthogonal moiety of the first hydrophilic region of the block copolymer and with the second bioorthogonal moiety of monomers or oligomers in the cell stabilization system. In some embodiments, the second hydrophilic region of the block copolymer may include a bioorthogonal reactive moiety, which may be the same or different as the bioorthogonal reactive moiety of the first hydrophilic region, and may optionally react with bioorthogonal reactive moieties of monomers or oligomers to form an extracellular polymer network.

In one embodiment, the first bioorthogonal reactive moiety of the monomers or oligomer includes an azide group, the second bioorthogonal reactive moiety of the monomers or oligomers includes an alkyne group, and the bioorthogonal reactive moiety of the first hydrophilic region, and optionally the second hydrophilic region, of the block copolymer includes an alkyne group. In another embodiment, the first bioorthogonal reactive moiety of the monomers or oligomers includes an alkyne group, the second bioorthogonal reactive moiety of the monomers or oligomers includes an azide group, and the bioorthogonal reactive moiety of the first hydrophilic region, and optionally the second hydrophilic region, of the block copolymer includes an azide group.

In some embodiments, the monomers or oligomers include amino acids, peptides, sugar molecules, nucleosides, nucleotides, cell penetrating peptides, or toxin molecules.

In an aspect, biological particles, (e.g. stabilized biological particles are provided. The biological particle may be selected from the group comprising cells and organelles. A biological particle (e.g., cell, organelle) may include a plurality of block copolymers as described herein, wherein the biological particle comprises a biological particle membrane comprising an intra-biological particle face that faces the inside of the biological particle and an extra-biological particle facing side that faces the outside of the biological particle, and wherein the hydrophobic regions of the block copolymers are inserted into the biological particle membrane. The biological particle may comprise an intra-biological particle network formed by polymerization of a plurality of monomers or oligomers that are capable of accumulating within the biological particle and that comprise a first bioorthogonal moiety that is capable of reacting with the bioorthogonal moiety of the first hydrophilic regions of the inserted block copolymers, and a second bioorthogonal moiety that is capable of reacting with the first bioorthogonal moiety.

In another aspect, cells (e.g., stabilized cells) are provided. A cell may include a plurality of block copolymers as described herein inserted into the cell membrane. The first hydrophilic regions of the block copolymers, on the interior of the cell, are polymerized via reaction of the bioorthogonal reactive moiety of the first hydrophilic region with the first bioorthogonal reactive moiety of monomers or oligomers as described herein and subsequent reaction of first and second bioorthogonal reactive moieties between monomers or oligomers to form an intracellular polymer network on the inside of the cell.

In another aspect, organelles (e.g., stabilized organelles) are provided. An organelle may include a plurality of block copolymers as described herein inserted into the organelle membrane. The first hydrophilic regions of the block copolymers, on the interior of the cell, are polymerized via reaction of the bioorthogonal reactive moiety of the first hydrophilic region with the first bioorthogonal reactive moiety of monomers or oligomers as described herein and subsequent reaction of first and second bioorthogonal reactive moieties between monomers or oligomers to form an intra-organellar polymer network on the inside of the organelle.

In some embodiments, the second hydrophilic regions of the block copolymers inserted into the membrane include a bioorthogonal reactive moiety, with may be the same or different as the bioorthogonal reactive moiety of the first hydrophilic region, and the bioorthogonal reactive moieties of the second hydrophilic regions of the block copolymers are polymerized to form an extracellular polymer network on the outside of the cell. For example, the bioorthogonal reactive moiety of the second hydrophilic region may react with a bioorthogonal reactive moiety of monomers or oligomers, which may be the same or different as the monomers or oligomers that react to form the intra-biological particle polymer network, and subsequent reaction between bioorthogonal reactive moieties (for example, but not limited to, first and second bioorthogonal reactive moieties of the monomers or oligomers that react with the bioorthogonal reactive moiety of the first hydrophilic region to form the intra-biological particle polymer network), thereby forming an extra-biological particle polymer network on the outside of the biological particle.

In other embodiments, the second hydrophilic regions of inserted block copolymers include a membrane impermeable moiety, which is oriented on the extra-biological particle face of the biological particle membrane. In some aspects, the second hydrophilic regions of inserted block copolymers include a cell membrane impermeable moiety, which is oriented on the extracellular side of the cell membrane. In some aspects, the second hydrophilic regions of inserted block copolymers include an organelle membrane impermeable moiety, which is oriented on the extracellular side or face of the organelle membrane.

In some embodiments, a biomolecule of interest in the cell (for example, but not limited to, a nucleic acid, a protein, a lipid, or a carbohydrate) is not degraded by formation of the polymer network. In an aspect, a biomolecule of interest in the cell (for example, but not limited to, a nucleic acid, a protein, a lipid, or a carbohydrate) is not degraded by formation of the intra-biological particle polymer network. In an aspect, a biomolecule of interest in the organelle (for example, but not limited to, a nucleic acid, a protein, a lipid, or a carbohydrate) is not degraded by formation of the intra-organellar polymer network. In an embodiment, the biomolecule of interest is RNA.

In some embodiments, the biological particle further comprises a fixative to stabilize the biological particle architecture. In some embodiments, the cell is further treated with a fixative to stabilize the cell architecture. In some aspects, the organelle further comprises a fixative to stabilize the biological particle architecture. For example, the fixative may include paraformaldehyde, formalin, methanol, hypothermisol, or RNAlater.

In some embodiments, the biological particle is in a biological tissue or tumor sample. In some embodiments, the cell is in a biological tissue or tumor sample. In some embodiments, the organelle is in a biological tissue or tumor sample. In other embodiments, the cell is isolated from a biological sample, such as isolated from a tissue sample or tumor sample. In other embodiments, the organelle is isolated from a biological sample, such as isolated from a tissue sample or a tumor sample. In an embodiment, the cell is in a suspension of cells from the biological sample, such as a suspension of cells from a biological tissue or tumor sample.

In another aspect, methods are provided for stabilization of biological particles, e.g., for biomolecule analysis. The methods include: (a) contacting a biological particle with a plurality of block copolymers as described above, wherein the hydrophobic regions of at least a portion of the plurality of block copolymers insert into the membrane, and wherein the first hydrophilic regions of the block copolymers are oriented on the intra-biological particle side of the biological particle membrane; and (b) polymerizing the bioorthogonal reactive moieties of the first hydrophilic regions to form an intracellular polymer network, wherein a biomolecule of interest is retained within the biological particle and is not degraded by formation of the intracellular polymer network. The methods may include (a) contacting a cell with a plurality of block copolymers as described above, wherein the hydrophobic regions of at least a portion of the plurality of block copolymers insert into the cell membrane.

In some embodiments, step (b) includes contacting the biological particle with a plurality of monomers or oligomers, as described above, that are capable of accumulating within the cell and that include: a first bioorthogonal moiety of the first hydrophilic region, and a second bioorthogonal moiety that is capable of reacting with the first bioorthogonal moiety, wherein the monomers or oligomers are polymerized inside the cell via reaction of the first and second bioorthogonal reaction moieties. In some embodiments, step (b) includes contacting the cell with a plurality of monomers or oligomers, as described above, that are capable of accumulating within the cell and that include: a first bioorthogonal moiety that is capable of reacting with the bioorthogonal moiety of the first hydrophilic region, and a second bioorthogonal moiety that is capable of reacting with the first bioorthogonal moiety, wherein the monomers or oligomers are polymerized inside the cell via reaction of the first and second bioorthogonal reactive moieties. The first hydrophilic regions of the block copolymers, as described herein, are polymerized via reaction of the bioorthogonal reactive moieties of the first hydrophilic regions with the first bioorthogonal reactive moiety of the monomers or oligomers and subsequent reaction between the first and second bioorthogonal reactive moieties between monomers or oligomers to form an intracellular polymer network on the inside of the biological particle.

In some embodiments, the second hydrophilic regions of the plurality of block copolymers include a bioorthogonal reactive moiety, which may be the same or different as the bioorthogonal reactive moiety of the first hydrophilic region, and step (b) includes polymerizing the bioorthogonal reactive moieties of the second hydrophilic regions to form an extra-biological particle polymer network. In some embodiments, the second hydrophilic regions of the plurality of block copolymers include a bioorthogonal reactive moiety, which may be the same or different as the bioorthogonal reactive moiety of the first hydrophilic region, and step (b) includes polymerizing the bioorthogonal reactive moieties of the second hydrophilic regions to form an extracellular polymer network. In some embodiments, the bioorthogonal reactive moieties of the second hydrophilic regions of the block copolymers are polymerized via reaction of the bioorthogonal reactive moiety of the second hydrophilic region with the first or second bioorthogonal reactive moiety of the monomers or oligomers, and subsequent reaction of the first and second bioorthogonal reactive moieties between monomers and or oligomers to form an extra-biological particular polymer network on the outside of the biological particle. In some embodiments, the bioorthogonal reactive moieties of the second hydrophilic regions of the block copolymers are polymerized via reaction of the bioorthogonal reactive moiety of the second hydrophilic region with the first or second bioorthogonal reactive moiety of the monomers or oligomers, and subsequent reaction of the first and second bioorthogonal reactive moieties between monomers or oligomers to form an extracellular polymer network on the outside of the cell.

In some embodiments, the monomers or oligomers include amino acids, peptides, sugar molecules, nucleosides, nucleotides, cell penetrating peptides, or toxin molecules.

In some embodiments, the second hydrophilic regions of the plurality of inserted block copolymers include biological particle membrane impermeable moieties that are oriented on the extra-biological particle facing side of the biological particle membrane. In some embodiments, the second hydrophilic regions of the plurality of inserted block copolymers include cell membrane impermeable moieties that are oriented on the extracellular side of the cell membrane. For example, the membrane impermeable moiety may include, for example, an affinity moiety, and/or a detectable label (e.g., a nanoparticle, a fluorophore, and/or a radiolabel). In some embodiments, the membrane impermeable moiety includes an affinity moiety, which may comprise or consist of a member of an affinity binding pair, such as, for example, avidin, streptavidin, biotin, digoxigenin, a lectin, a carbohydrate, a lipid, an antibody or antigen-binding fragment thereof, an oligonucleotide, a receptor, or a receptor ligand. In some embodiments, the method may include contacting the biological particle with a molecule that binds to the affinity moiety, such as, for example, a member of an affinity binding pair that binds to the affinity moiety.

In some embodiments, the biomolecule of interest is a nucleic acid, a protein, a lipid, or a carbohydrate. For example, in one embodiment, the biomolecule of interest is RNA, and the method may further include reverse transcription of the RNA.

In some embodiments of the method, the biological particle is in a biological tissue or tumor sample. In other embodiments, the biological particle is isolated from a biological sample, such as isolated from a tissue sample or tumor sample. In an embodiment, the biological particle is in a suspension of biological particles from the biological sample. In an embodiment, the cell is in a suspension of cells from the biological sample, such as a suspension of cells from a biological tissue or tumor sample.

In some embodiments, the method includes contacting the biological particle or a tissue that includes the biological particle with a fixative to stabilize the biological particle architecture, for example, in conjunction with or after formation of the intra-biological particle polymer network. In some embodiments, the method includes contacting the cell or a tissue that includes the cell with a fixative to stabilize the cell architecture, for example, in conjunction with or after formation of the intracellular polymer network. For example, the fixative may include paraformaldehyde, formalin, methanol, hypothermisol, or RNAlater.

In some embodiments of the method, the hydrophobic regions of the block copolymers comprise or consist of poly(propylene oxide). In some embodiments, the first and/or second hydrophilic regions of the block copolymers comprise or consist of poly(ethylene oxide).

In some embodiments, the bioorthogonal reactive moieties on the first hydrophilic regions, and optionally on the second hydrophilic regions of the block copolymers, include an alkyne group or an azide group. In one embodiment, the first bioorthogonal moiety of the monomers or oligomers includes an azide group, the second bioorthogonal moiety of the monomers or oligomers includes an alkyne group, and the bioorthogonal moiety of the first hydrophilic region, and optionally the second hydrophilic region, of the block copolymer includes an alkyne group. In another embodiment, the first bioorthogonal moiety of the monomers or oligomers includes an alkyne group, the second bioorthogonal moiety of the monomers or oligomers includes an azide group, and the bioorthogonal moiety of the first hydrophilic region, and optionally the second hydrophilic region, of the block copolymer includes an azide group.

In some embodiments, the method further includes depolymerizing the intra-biological particle polymer network, and optionally the extra-biological particle polymer network if present, prior to analysis of the biomolecule of interest, e.g. to release or render accessible for analysis one or more biomolecules of interest. In some embodiments, the method further includes depolymerizing the intracellular polymer network, and optionally the extracellular polymer network if present, prior to analysis of the biomolecule of interest, e.g., to release or render accessible for analysis one or more biomolecule of interest. For example, analysis of biomolecule(s) of interest may include determination of the presence or absence, and/or quantity, of the biomolecule(s) of interest in the cell. Single cells may be analyzed or a sample that contains a plurality of cells, such as a tissue sample, may be analyzed, and presence, absence, quantity, and/or spatial location of one or more biomolecule is determined.

In some embodiments, a multiplexed assay for biomolecules of interest is provided, including performing a method for stabilization of cells as described herein, and further including determining the presence or absence, and/or quantity, of two or more biomolecules of interest that are retained in the cell. Single cells may be analyzed or a sample that contains a plurality of cells, such as a tissue sample, may be analyzed, and presence, absence, quantity, and/or spatial location of two or more biomolecules is determined.

In another aspect, methods are provided for spatial analysis of one or more analyte in a biological sample. The methods include: (a) contacting a biological sample with a plurality of block copolymers as described above, wherein the hydrophobic regions of at least a portion of the block copolymers insert into membranes of biological particles within the biological sample, and the first hydrophilic regions of the block copolymers are oriented on the intra-biological particle facing side of the biological particle membrane; (b) polymerizing the bioorthogonal reactive moieties on the first hydrophilic regions to form an intra-biological particle polymer network, as describe above, and optionally forming an extra-biological particle polymer network, as described above, wherein one or more biological analyte of interest is retained within the biological particles and is not degraded by formation of the intra-biological particle polymer network; and (c) determining presence, absence, quantity, and/or spatial location of the one or more biological analytes in the biological sample. The methods include: (a) contacting a biological sample with a plurality of block copolymers as described above, wherein the hydrophobic regions of at least a portion of the block copolymers insert into cell membranes of cells within the biological sample, and the first hydrophilic regions of the block copolymers are oriented on the intracellular side of the cell membrane; (b) polymerizing the bioorthogonal reactive moieties on the first hydrophilic regions to form an intracellular polymer network, as described above, and optionally forming an extracellular polymer network, as described above, wherein one or more biological analyte of interest is retained within the cells and is not degraded by formation of the intracellular polymer network; and (c) determining presence, absence, quantity, and/or spatial location of the one or more biological analyte in the biological sample. In some embodiments, the biological sample is a tissue sample, and the method further includes sectioning the tissue sample

BRIEF DESCRIPTION OF THE DRAWINGS

The following drawings illustrate certain embodiments of the features and advantages of this disclosure. These embodiments are not intended to limit the scope of the appended claims in any manner. Like reference symbols in the drawings indicate like elements.

FIG. 11A schematically shows an example of labelling agents. FIG. 11B schematically shows another example workflow for processing nucleic acid molecules.

FIGS. 18A, 18B, and 18C are schematics illustrating how streptavidin cell tags can be utilized in an array-based system to produce spatially-barcoded cells or cellular contents.

DETAILED DESCRIPTION

I. Introduction

Figure 1:
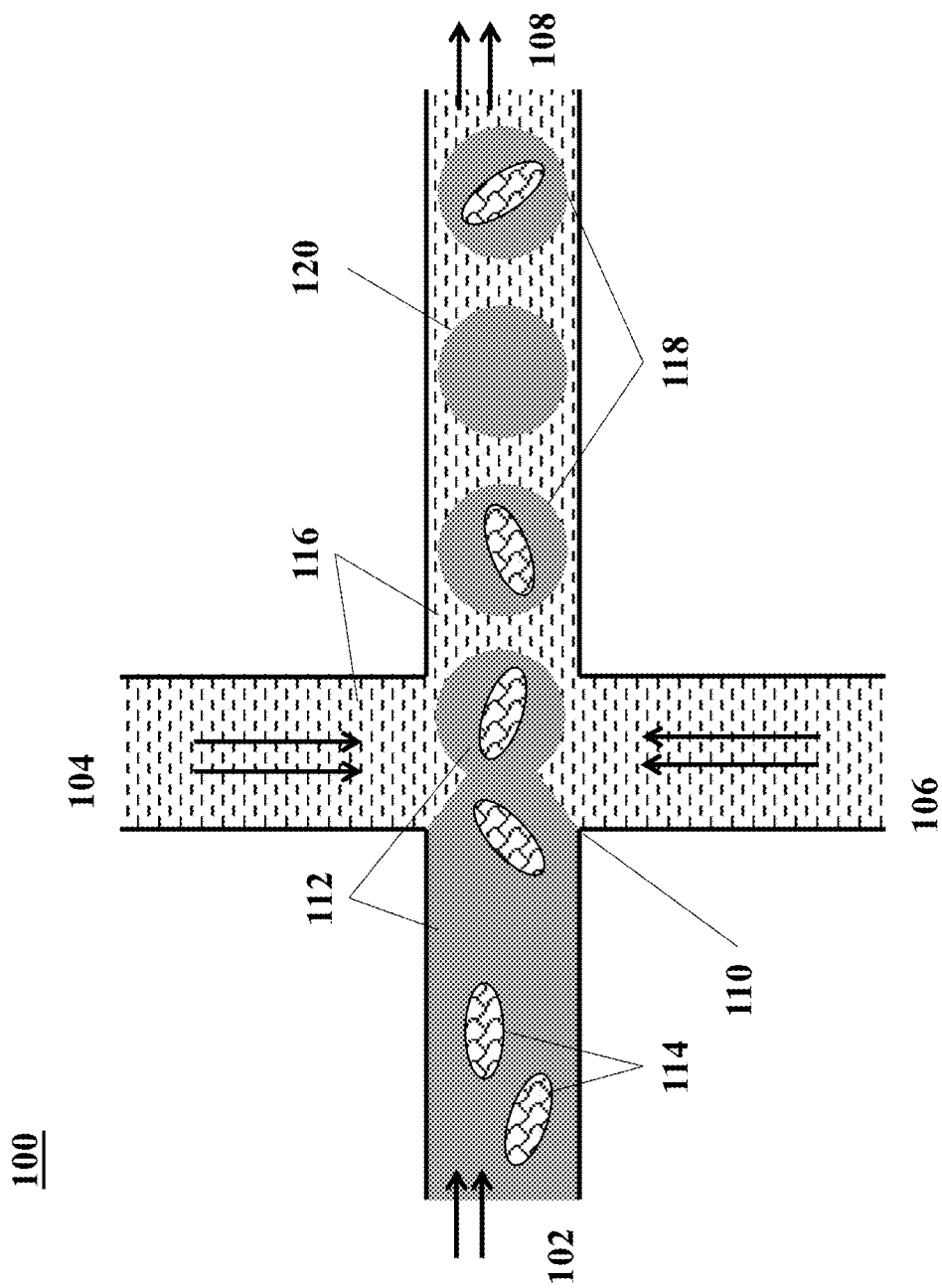
FIG. 1 shows an example of a microfluidic channel structure for partitioning individual biological particles.

Systems and methods for biological particles stabilization are provided herein. Systems and methods for cell stabilization are provided herein. A system for biological particle stabilization and a system for cell stabilization as described herein include two primary components. The first component is a triblock copolymer with a hydrophobic core and hydrophilic flanking regions, one or both of which is modified with a bioorthogonal reactive moiety, such as, but not limited to, an azide or alkyne moiety.

In the asymmetric case, i.e., one hydrophilic region modified with a bioorthogonal reactive moiety, the other hydrophilic region of the block copolymer may be covalently bonded to a large handle molecule, such as, but not limited to, streptavidin, or another molecule or moiety that is impermeable to the membrane, which serves to orient the block copolymer with the handle molecule on the extra-biological particle facing side side of the membrane. The handle molecule may be used, for example, in biological particle multiplexing, biological particle purification, cell multiplexing, cell purification, or some other assay-specific function. The bioorthogonal reactive moiety on the intra-biological particle facing side of the biological particle membrane may serve as a membrane-bound anchor for polymerization of biological particle internal polymer network. The bioorthogonal reactive moiety on the intracellular side of the cell membrane may serve as a membrane-bound anchor for polymerization of a cell internal polymer network. The second component of the system include chemical compounds or biomolecule monomers (or short oligomers) modified with first and second bioorthogonal reactive moieties. A first bioorthogonal reactive moiety is compatible for reaction with the bioorthogonal reactive moiety of the first component, i.e., the first hydrophilic region of the block copolymer described above, and with a second bioorthogonal reactive moiety. Reaction of the first and second moieties of the monomers and oligomers results in formation of an intra-biological particle polymer network. Reaction of the first and second moieties of the monomers and oligomers results in formation of an intracellular polymer network. The second component is capable of: accumulation inside of an intact biological particle (e.g., a monomer/oligomer that can cross the biological particle membrane); polymerization (e.g., sequential reaction between first and second bioorthogonal moieties of monomers or oligomers), without degradation of or interference with biomolecules of interest or biological particle integrity (e.g., polymerization conditions are not destructive to the structural integrity of the monomer or oligomer); and formation of a polymer network inside the biological particle from polymerization of the bioorthogonal relative moieties of the first and second compounds that does not interfere with downstream applications of use, such as, but not limited to, detection, analysis, quantitation, and/or spatial analysis of one or more biomolecule(s) within a biological particle or within a biological sample that includes the biological particle, partitioning of the biological particles, preparation of sequencing libraries, or reverse transcription and/or translation. The second component is capable of: accumulation inside of an intact cell (e.g., a monomer/oligomer that can cross the cell membrane); polymerization (e.g., sequential reaction between first and second bioorthogonal moieties of monomers or oligomers), without degradation of or interference with biomolecules of interest or cell integrity (i.e., polymerization conditions are not destructive to the structural integrity of the monomer or oligomer); and formation of a polymer network inside of a cell from polymerization of the bioorthogonal reactive moieties of the first and second components that does not interfere with downstream applications of use, such as, but not limited to, detection, analysis, quantitation, and/or spatial analysis of one or more biomolecule(s) within a cell or within a biological sample that includes the cell, partitioning of cells or cell nuclei, preparation of sequencing libraries, or reverse transcription and/or translation. Nonlimiting applications of use include, but are not limited to, single-cell RNA-seq (scRNA-seq) technology, e.g., gel beads in emulsion technology ("GEM") (see, e.g., www.10xgenomics.com/blog/single-cell-rna-seq-an-introductory-overview-and-tools-for-getting-started) and spatial analysis, such as spatial transcriptomics (see, e.g., assets.ctfassets.net/an68im79xiti/5UJrN0cH17rEk0 UXwd19It/e54d99fb08a8f1500aba503005a04a56/ CG000238_VisiumSpatialTissueOptimizationUserGuide_ RevD.pdf). The polymer network formed inside a biological particle may be optionally degradable or depolymerizable by a second chemistry or enzyme, e.g., a chemistry or enzyme that is compatible with a downstream application of use, such as, but not limited to scRNA-seq (e.g., GEM) or spatial analysis (e.g., spatial transcriptomics).

Nonlimiting examples of bioorthogonal reactive moieties include "click" chemistry reactive moieties (e.g., copper-free click chemistry) (Baskin, J., et al. (2007) *Proc Natl Acad Sci USA* 104(43):16793-16797). Nonlimiting examples of membrane permeable monomers or oligomers include amino acids, dipeptides, and sugar (carbohydrate) molecules (e.g., sugar molecules that can be transported through cell membrane transporters but that are not compatible with cell metabolism). Loss of biological molecules of interest from the interior of a biological particle results in data loss and less accurate results. Leakage is particularly an issue when working with a single biological particle (e.g. single cell). Prior fixatives allowed biological molecules of interest (such as, but not limited to RNA) to leak out of the biological particle resulting in data loss. The block copolymers of the current application can advantageously stabilize biological particle membranes. Biological particles stabilized by the current methods and materials exhibit an improved signal to noise ratio as compared to biological particles stabilized with prior fixatives. Without being limited by mechanism, the block copolymers may prevent leaks of biological molecules of interest and may improve retention of biological molecules of interest. The block copolymers form robust polymer networks within biological particles. Biological particles stabilized by block copolymers better retain biological molecules of interest. The systems for biological particle stabilization result in stabilized membranes with reduced brittleness. The reduced brittleness may decrease porosity and reduce the leak of biological molecules of interest.

II. Definitions

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

Numeric ranges provided herein are inclusive of the numbers defining the range.

"A," "an" and "the" include plural references unless the context clearly dictates otherwise.

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add one or more function, e.g., spacer sequences, primer sequences/sites, barcode sequences, unique molecular identifier sequences.

As used herein, an "adhesive" generally refers to a substance used for sticking objects or materials together. Adhesives include, for example, glues, pastes, liquid tapes, epoxy, bioadhesives, gels, and mucilage. In some embodiments, an adhesive is liquid tape. In some embodiments, the adhesive is glue.

An "affinity group" is a molecule or molecular moiety which has a high affinity or preference for associating or binding with another specific or particular molecule or moiety. The association or binding with another specific or particular molecule or moiety can be via a non-covalent interaction, such as hydrogen bonding, ionic forces, and van der Waals interactions. An affinity group can, for example, be biotin, which has a high affinity or preference to associate or bind to the protein avidin or streptavidin. An affinity group, for example, can also refer to avidin or streptavidin which has an affinity to biotin. Other examples of an affinity group and specific or particular molecule or moiety to which it binds or associates with include, but are not limited to, antibodies or antibody fragments and their respective antigens, such as digoxigenin and anti-digoxigenin antibodies, lectin, and carbohydrates (e.g., a sugar, a monosaccharide, a disaccharide, or a polysaccharide), and receptors and receptor ligands.

Any pair of affinity group and its specific or particular molecule or moiety to which it binds or associates with can have their roles reversed, for example, such that between a first molecule and a second molecule, in a first instance the first molecule is characterized as an affinity group for the second molecule, and in a second instance the second molecule is characterized as an affinity group for the first molecule.

The apparatus, systems, methods, and compositions described in this disclosure can be used to detect and analyze a wide variety of different analytes. For the purpose of this disclosure, an "analyte" can include any biological substance, structure, moiety, or component to be analyzed. The term "target" can similarly refer to an analyte of interest.

An "analyte binding moiety" is a molecule capable of binding to an analyte, e.g., a molecule or moiety capable of binding to a macromolecular constituent (e.g., an analyte, e.g., a biological analyte).

As used herein, the term "analyte binding moiety barcode" refers to a barcode that is associated with or otherwise identifies an analyte binding moiety.

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also include single domain antibodies (VHH domains and VNAR domains), scFvs, and Fab fragments.

In general, a sequence element located "at the 3' end" includes the 3'-most nucleotide of the oligonucleotide, and a sequence element located "at the 5' end" includes the 5'-most nucleotide of the oligonucleotide.

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

The term "base pair" or "bp" as used herein refers to a partnership (i.e., hydrogen bonded pairing) of adenine (A) with thymine (T), or of cytosine (C) with guanine (G) in a double stranded DNA molecule. In some embodiments, a base pair may include A paired with Uracil (U), for example, in a DNA/RNA duplex.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence or a non-targeted sequence. The nucleic acid barcode molecule may be coupled to or attached to the nucleic acid molecule comprising the nucleic acid sequence. For example, in the methods and systems described herein, hybridization and reverse transcription of a nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). The processing of the nucleic acid molecule comprising the nucleic acid sequence, the nucleic acid barcode molecule, or both, can include a nucleic acid reaction, such as, in non-limiting examples, reverse transcription, nucleic acid extension, ligation, etc. The nucleic acid reaction may be performed prior to, during, or following barcoding of the nucleic acid sequence to generate the barcoded nucleic acid molecule. For example, the nucleic acid molecule comprising the nucleic acid sequence may be subjected to reverse transcription and then be attached to the nucleic acid barcode molecule to generate the barcoded nucleic acid molecule, or the nucleic acid molecule comprising the nucleic acid sequence may be attached to the nucleic acid barcode molecule and subjected to a nucleic acid reaction (e.g., extension, ligation) to generate the barcoded nucleic acid molecule. A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the nucleic acid molecule (e.g., mRNA).

"Bioorthogonal" chemistry refers to a chemical reaction that can occur inside of a living system or a cell, without interfering with a biochemical process, such as an enzymatic reaction or production of a biomolecule, within the system or cell, e.g., the bioorthogonal reaction is biologically inert.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle, e.g., a nucleus, a mitochondrion, a liposome, a plastid, endoplasmic reticulum, a lysosome, a ribosome, a vacuole, a vesicle, a flagellum, and a centriole. A cell may be a live cell. The live cell may be capable of being cultured, for example, being cultured when enclosed in a gel or polymer matrix, or cultured when comprising a gel or polymer matrix. The biological particle may comprise a membrane surrounding the biological particle, wherein the membrane comprises an intra-biological particle facing side and an extra-biological particle facing side that faces the outside of the biological particle.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

A "bioorthogonal reactive moiety" is a small molecule or functional group that can react in a bioorthogonal manner within a living system or cell.

A "capture probe" refers to any molecule capable of capturing (directly or indirectly) and/or labelling an analyte (e.g., an analyte of interest) in a biological sample.

A "cell-penetrating peptide" (CPP) or "protein transduction domain" refers to a short peptide that facilitates cellular intake and uptake of molecules (cargo) ranging from nano-size particles to small chemical compounds to larger molecules such as fragments of DNA. The "cargo" may be associated with the peptide through chemical linkage (covalent bonds) or through non-covalent interaction.

A "cell-permissive coating" is a coating that allows or helps cells to maintain cell viability (e.g., remain viable) on a substrate.

In general, a "complement" of a given nucleic acid sequence is a sequence that is fully complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g., thermodynamically more stable under a given set of conditions, such as stringent conditions commonly used in the art) in comparison with hybridization with non-target sequences during a hybridization reaction. Typically, hybridizable sequences share a degree of sequence complementarity over all or a portion of their respective lengths, such as 25%-100% complementarity, including at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "complementary" herein refers to the broad concept of sequence complementarity in duplex regions of a single polynucleotide strand or between two polynucleotide strands between pairs of nucleotides through base-pairing. It is known that an adenine nucleotide is capable of forming specific hydrogen bonds ("base pairing") with a nucleotide, which is thymine or uracil. Similarly, it is known that a cytosine nucleotide is capable of base pairing with a guanine nucleotide. However, in certain circumstances, hydrogen bonds may also form between other pairs of bases, e.g., between adenine and cytosine, etc. "Essentially complementary" herein refers to sequence complementarity in duplex regions of a single polynucleotide strand or between two polynucleotide strands, for example, wherein the complementarity is less than 100% but is greater than 90%, and retains the stability of the duplex region.

A "conditionally removable coating" is a coating that can be removed from the surface of a substrate upon application of a releasing agent.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g., DNA polymerase activity of the wild-type sequence. Mutations can affect the activity profile of the enzymes, e.g., enhance or reduce the rate of polymerization, under different reaction conditions, e.g., temperature, template concentration, primer concentration, etc. Mutations or sequence-modifications can also affect the exonuclease activity and/or thermostability of the enzyme.

The term "derived from" encompasses the terms "originated from," "obtained from," "obtainable from," "isolated from," and "created from," and generally indicates that one specified material finds its origin in another specified material or has features that can be described with reference to another specified material.

The terms "detectable label," "optical label," and "label" are used interchangeably herein to refer to a directly or indirectly detectable moiety that is associated with (e.g., conjugated to or bound to) a molecule to be detected, e.g., a capture probe or analyte, or a molecule that binds to a capture probe or analyte. The detectable label can be directly detectable by itself (e.g., radioisotope labels, fluorescent labels, or metal labels) or, in the case of an enzymatic label, can be indirectly detectable, e.g., by catalyzing chemical alterations of a chemical substrate compound or composition, which chemical substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, dyes, and metals.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to or bound to a feature, capture probe, or composition to be detected. For example, detectable labels can be incorporated during nucleic acid polymerization or amplification (e.g., Cy5®-labelled nucleotides, such as Cy5®-dCTP).

Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7® Cychrome (PE-Cy5), Dansylamine, Dansyl cadaverine, Dansylchloride, DAPI, Dapoxyl, DCFH, DHR, DiA (4-Di-16-ASP), DiD (DilC18(5)), DIDS, Dil (DilC18(3)), DiO (DiOC18 (3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorophyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Re®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66 W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705,5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

In some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate chemical substrates (e.g., an oxidizing reagent plus a chemiluminescent compound). A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinium esters, luciferins, lucigenins, or acridinium esters.

The term "duplex" herein refers to a region of complementarity that exists between two polynucleotide sequences. The term "duplex region" refers to the region of sequence complementarity that exists between two oligonucleotides or two portions of a single oligonucleotide.

An "extendible 3' end" refers an oligonucleotide with a terminal 3' nucleotide that may be extended, for example, by a polymerase enzyme, e.g., a 3' nucleotide that contains a 3' hydroxyl group.

A "gel" refers to a semi-rigid material permeable to liquids and gases.

A "gene" refers to a DNA segment that is involved in producing a polypeptide and includes regions preceding and following the coding regions as well as intervening sequences (introns) between individual coding segments (exons).

A "genome" generally refers to genomic information from a subject, which can be, for example, at least a portion of, or the entirety of, the subject's gene-encoded hereditary information. A genome can include coding regions (e.g., that code for proteins) as well as non-coding regions. A genome can include the sequences of some or all of the subject's chromosomes. For example, the human genome ordinarily has a total of 46 chromosomes. The sequences of some or all of these can constitute the genome.

As used herein, the term "histone protein" refers to a linker histone protein (e.g., H1) and/or a core histone protein (e.g., H2A, H2B, H3, and H4).

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

The term "hydrogel" herein refers to a macromolecular polymer gel including a network. Within the network, some polymer chains can optionally be cross-linked, although cross-linking does not always occur.

When referring to immobilization or attachment of molecules (e.g., nucleic acids) to a support, e.g., a solid support, the terms "immobilized" and "attached" are used interchangeably herein, and both terms are intended to encompass direct or indirect, covalent or non-covalent attachment, unless indicated otherwise. In some embodiments, covalent attachment may be preferred, but generally all that is required is that the molecules (e.g., nucleic acids) remain immobilized or attached to the support under the conditions in which it is intended to use the support, for example in nucleic acid amplification and/or sequencing applications. "Covalent attachment" is intended to encompass both direct attachment and indirect attachment such as through a linker.

The terms "isolated," "purified," "separated," and "recovered" as used herein refer to a material (e.g., a protein, nucleic acid, or cell) that is removed from at least one component with which it is naturally associated, for example, at a concentration of at least 90% by weight, or at least 95% by weight, or at least 98% by weight of the sample in which it is contained. For example, these terms may refer to a material which is substantially or essentially free from components which normally accompany it as found in its native state, such as, for example, an intact biological system. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

The terms "joining" and "ligation" as used herein, with respect to two polynucleotides, such as an adapter oligonucleotide and a sample polynucleotide, refers to the covalent attachment of two separate polynucleotides to produce a single larger polynucleotide with a contiguous backbone. "Covalent attachment" is intended to encompass both direct attachment and indirect attachment such as through a linker.

As used herein, a "linker" generally refers to a multifunctional (e.g., bifunctional, trifunctional) reagent used for conjugating two or more chemical moieties.

A "monomer" refers to a molecule that can be covalently bonded to other molecules to form a polymer. An "oligomer"

refers to a polymer whose molecules consist of relatively few monomers (e.g., dimer, trimer).

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule (i.e., an extension product). For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope, fluorophore, or metal).

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments. A variety of different vessels are described in, for example, U.S. Patent Application Publication No. 2014/0155295. Emulsion systems for creating stable droplets in non-aqueous or oil continuous phases are described in detail in, e.g., U.S. Patent Application Publication No. 2010/010511.

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4, 5, 6, 8, 9, 10, 11, 12, 13, 14, 15, 16, 17, 18, 19, 20, 25, 30, or 35 base pairs (bp), and can be as long as 40 bp or longer, where the length of the primers will generally range from 18 to 50 bases. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oNTM DNA ligase, available from New England Biolabs, Ipswich, MA), and Ampligase™ (available from Epicentre Biotechnologies, Madison, WI). Derivatives, e.g., sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g., reverse transcriptase, activity of the wild-type sequence. The reverse transcriptase enzyme can be provided as part of a composition that includes other components, e.g., stabilizing components that enhance or improve the activity of the reverse transcriptase enzyme, such as RNase inhibitor(s), inhibitors of DNA-dependent DNA synthesis, e.g., actinomycin D. Many sequence-modified derivative or mutants of reverse transcriptase enzymes, e.g., M-MLV, and compositions including unmodified and modified enzymes are commercially available, e.g., ArrayScript™, MultiScribe™, ThermoScript™, and SuperScript® I, II, III, and IV enzymes.

Certain reverse transcriptase enzymes (e.g., Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g., an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

"Peptide" refers to a compound consisting of two or more amino acids linked in a chain, the carboxyl group of each acid being joined to the amino group of the next by a bond of the type R—OC-NH-R', for example, about 2 to about 50 amino acids.

A "photo-crosslinkable polymer precursor" refers to a compound that cross-links and/or polymerizes upon exposure to light. In some embodiments, one or more photoinitiators may also be included to induce and/or promote polymerization and/or cross-linking. See, e.g., Choi et al. *Biotechniques*. 2019 January; 66(1):40-53, which is incorporated herein by reference in its entirety.

The term "polymerase" herein refers to an enzyme that catalyzes the polymerization of nucleotides (i.e., the polymerase activity). The term polymerase encompasses DNA polymerases, RNA polymerases, and reverse transcriptases. A "DNA polymerase" catalyzes the polymerization of deoxyribonucleotides. An "RNA polymerase" catalyzes the polymerization of ribonucleotides. A "reverse transcriptase" catalyzes the polymerization of deoxyribonucleotides that are complementary to an RNA template.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may include modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

A "primer" is a single-stranded nucleic acid sequence having a 3' end that can be used as a chemical substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases.

A "primer extension" refers to any method where two nucleic acid sequences (e.g., a constant region from each of two distinct capture probes) become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

As used herein, the term "RNA protectant" refers to a reagent that protects RNA from RNA nucleases (e.g., RNases).

A "releasing agent" or "external trigger" is an agent that allows for the removal of a conditionally removable coating from a substrate when the releasing agent is applied to the conditionally removable coating. An external trigger or releasing agent can include physical triggers such as thermal, magnetic, ultrasonic, electrochemical, and/or light stimuli as well as chemical triggers such as pH, redox reactions, supramolecular complexes, and/or biocatalytically driven reactions. See, e.g., Echeverria, et al., Gels (2018), 4, 54; doi:10.3390/gels4020054, which is incorporated herein by reference in its entirety. The type of "releasing agent" or "external trigger" can depend on the type of conditionally removable coating. For example, a conditionally removable coating featuring a redox-responsive hydrogel can be removed upon application of a releasing agent that includes a reducing agent such as dithiothreitol (DTT). As another example, a pH-responsive hydrogel can be removed upon the application of a releasing agent that changes the pH.

"Selective permeabilization" refers to a permeabilization method that can permeabilize a membrane of a subcellular region while leaving a different subcellular region substantially intact (e.g., biological analytes are not released from subcellular region due to the applied permeabilization method).

"Selective lysing" refers to a lysis method that can lyse a membrane of a subcellular region while leaving a different subcellular region substantially intact (e.g., biological analytes are not released from subcellular region due to the applied lysis method).

A "splint oligonucleotide" is an oligonucleotide that, when hybridized to other polynucleotides, acts as a "splint" to position the polynucleotides next to one another so that they can be ligated together. In some embodiments, the splint oligonucleotide is DNA or RNA. The splint oligonucleotide can include a nucleotide sequence that is partially complimentary to nucleotide sequences from two or more different oligonucleotides. In some embodiments, the splint oligonucleotide assists in ligating a "donor" oligonucleotide and an "acceptor" oligonucleotide. In general, an RNA ligase, a DNA ligase, or another other variety of ligase is used to ligate two nucleotide sequences together In some embodiments, the splint oligonucleotide is between 10 and 50 oligonucleotides in length, e.g., between 10 and 45, 10 and 40, 10 and 35, 10 and 30, 10 and 25, or 10 and 20 oligonucleotides in length. In some embodiments, the splint oligonucleotide is between 15 and 50, 15 and 45, 15 and 40, 15 and 35, 15 and 30, 15 and 30, or 15 and 25 nucleotides in length.

A "subject" or "individual" refers to the source from which a biological sample is obtained, for example, but not limited to, a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (i.e., human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, or honey bee; an arachnid such as a spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*.

The phrases "substantially similar" and "substantially identical" in the context of at least two nucleic acids typically means that a polynucleotide includes a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) *J. Mol. Biol.* 215:403-410; Henikoff et al. (1989) *Proc. Natl. Acad. Sci.* 89:10915; Karlin et al. (1993) *Proc. Natl. Acad. Sci.* 90:5873; and Higgins et al. (1988) Gene 73:237). Software for performing BLAST analyses is publicly available through the National Center for Biotechnology Information. Also, databases may be searched using FASTA (Pearson et al. (1988) *Proc. Natl. Acad. Sci.* 85:2444-2448.) In some embodiments, substantially identical nucleic acid molecules hybridize to each other under stringent conditions (e.g., within a range of medium to high stringency).

A "substrate" is a support that is insoluble in aqueous liquid and which allows for positioning of biological samples, analytes, features, and/or capture probes on the substrate. Further, a "substrate" as used herein, and when not preceded by the modifier "chemical", refers to a member with at least one surface that generally functions to provide physical support for biological samples, analytes, and/or any of the other chemical and/or physical moieties, agents, and structures described herein.

Nucleic acid "synthesis" herein refers to any in vitro method for making a new strand of polynucleotide or elongating an existing polynucleotide (i.e., DNA or RNA) in a template dependent manner. Synthesis, according to the invention, can include amplification, which increases the number of copies of a polynucleotide template sequence with the use of a polymerase. Polynucleotide synthesis (e.g., amplification) results in the incorporation of nucleotides into a polynucleotide (e.g., extension from a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, polymerase chain reaction (PCR), and may include the use of labeled nucleotides, e.g., for probes and oligonucleotide primers, or for polynucleotide sequencing.

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

Nucleic acid "synthesis" herein refers to any in vitro method for making a new strand of polynucleotide or elongating an existing polynucleotide (i.e., DNA or RNA) in a template dependent manner. Synthesis, according to the invention, can include amplification, which increases the number of copies of a polynucleotide template sequence with the use of a polymerase. Polynucleotide synthesis (e.g., amplification) results in the incorporation of nucleotides into a polynucleotide (e.g., extension from a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, polymerase chain reaction (PCR), and may include the use of labeled nucleotides, e.g., for probes and oligonucleotide primers, or for polynucleotide sequencing.

The term "tag" refers to a detectable moiety that may be one or more atom(s) or molecule(s), or a collection of atoms and molecules. A tag may provide an optical, electrochemical, magnetic, or electrostatic (e.g., inductive, capacitive) signature.

The term "tagged nucleotide" herein refers to a nucleotide that includes a tag (or tag species) that is coupled to any location of the nucleotide including, but not limited to a phosphate (e.g., terminal phosphate), sugar or nitrogenous base moiety of the nucleotide. Tags may be one or more atom(s) or molecule(s), or a collection of atoms and molecules. A tag may provide an optical, electrochemical, magnetic, or electrostatic (e.g., inductive, capacitive) signature.

As used herein, the term "target polynucleotide" refers to a nucleic acid molecule or polynucleotide in a population of nucleic acid molecules having a target sequence to which one or more oligonucleotides are designed to hybridize. In some embodiments, a target sequence uniquely identifies a sequence derived from a sample, such as a particular genomic, mitochondrial, bacterial, viral, or RNA (e.g., mRNA, miRNA, primary miRNA, or pre-miRNA) sequence. In some embodiments, a target sequence is a common sequence shared by multiple different target polynucleotides, such as a common adapter sequence joined to different target polynucleotides. "Target polynucleotide" may be used to refer to a double-stranded nucleic acid molecule that includes a target sequence on one or both strands, or a single-stranded nucleic acid molecule including a target sequence, and may be derived from any source of or process for isolating or generating nucleic acid molecules. A target polynucleotide may include one or more (e.g., 1, 2, 3, 4, 5, 6, 7, 8, 9, 10, or more) target sequences, which may be the same or different. In general, different target polynucleotides include different sequences, such as one or more different nucleotides or one or more different target sequences.

The term "template DNA molecule" herein refers to a strand of a nucleic acid from which a complementary nucleic acid strand is synthesized by a DNA polymerase, for example, in a primer extension reaction.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

A "template switching oligonucleotide" is an oligonucleotide that hybridizes to untemplated nucleotides added by a reverse transcriptase (e.g., enzyme with terminal transferase activity) during reverse transcription. In some embodiments, a template switching oligonucleotide hybridizes to untemplated poly(C) nucleotides added by a reverse transcriptase. In some embodiments, the template switching oligonucleotide adds a common 5' sequence to full-length cDNA that is used for cDNA amplification.

In some embodiments, the template switching oligonucleotide adds a common sequence onto the 5' end of the RNA being reverse transcribed. For example, a template switching oligonucleotide can hybridize to untemplated poly(C) nucleotides added onto the end of a cDNA molecule and provide a template for the reverse transcriptase to continue replication to the 5' end of the template switching oligonucleotide, thereby generating full-length cDNA ready for further amplification. In some embodiments, once a full-length cDNA molecule is generated, the template switching oligonucleotide can serve as a primer in a cDNA amplification reaction.

In some embodiments, a template switching oligonucleotide is added before, contemporaneously with, or after a reverse transcription, or other terminal transferase-based reaction. In some embodiments, a template switching oligonucleotide is included in the capture probe. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target. In some embodiments, the hybridization region can, e.g., include a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In other embodiments, the hybridization region can include at least one base in addition to at least one G base. In other embodiments, the hybridization can include bases that are not a G base. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 1, 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

III. Systems for Biological Particle Stabilization

Systems for biological particle stabilization and systems for cell stabilization are provided. The systems described herein include two components, a block copolymer component, and a monomer/oligomer component. Both components contain bioorthogonal reactive moieties, capable of reaction to create an intracellular network of polymerized monomer/oligomer components within a cell. A stabilization system as described herein may include buffers and/or compounds (e.g., a "preservation buffer") to maintain biomolecule structure and stability, such as, but not limited to, RNase inhibitors, protease inhibitors, macromolecular osmotic stabilizers, etc.

A. Block Copolymers

Block copolymer (e.g., triblock copolymer) molecules are provided that are capable of insertion into membranes. A block copolymer herein includes a hydrophobic core region that is capable of stable insertion into and retention within a membrane. The block copolymer also includes two hydrophilic regions, a first hydrophilic region and a second hydrophilic region, which flank opposite ends of the hydrophobic core region. When a block copolymer is inserted into a biological particle membrane, e.g. a continuous, intact organelle membrane or a continuous, intact cell membrane, the first hydrophilic region is oriented on the inside of the biological particle membrane (e.g. intra-biological particle orientation) and the second hydrophilic region is oriented on the outside of the cell membrane (e.g. extra-biological particle orientation). When the block copolymer is inserted into a cell membrane, e.g., a continuous, intact cell membrane, the first hydrophilic region is oriented on the inside of the cell membrane (e.g., intracellular orientation) and the second hydrophilic region is oriented on the outside of the cell membrane (e.g., extracellular orientation).

At least the first hydrophilic region includes a bioorthogonal reactive moiety, e.g., the first hydrophilic region is modified with a bioorthogonal reactive moiety. In some embodiments, both the first hydrophilic region and the second hydrophilic region each includes a bioorthogonal reactive moiety, e.g., the first and second hydrophilic regions are both modified with bioorthogonal reactive moieties, which may be the same or different. In other embodiments, the first hydrophilic region includes a bioorthogonal reactive moiety and the second hydrophilic region includes a handle moiety that orients the second hydrophilic region to the extra-biological particle facing side of the biological particle membrane when the block copolymer is inserted into the membrane, e.g., the second hydrophilic region is membrane impermeable or includes a membrane impermeable moiety.

In some embodiments, the hydrophobic region includes a hydrophobic polymer, such as, but not limited to, poly(propylene oxide), polyethylene, polystyrene, poly(vinyl chloride), polytetrafluorethylene, polydimethylsiloxane, polyester, polyurethane, polyacrylic (e.g., acrylonitrile, acrylamide, maleic anhydride), epoxy, polyamide, polyimide polymer, polycarbonate, polydiene, polyester, polyether, polyolefin (polyethylene, polypropylene), poly(vinyl acetal), poly(vinyl acetate), poly(vinyl ether), and poly(vinyl pyrrolidone) polymers and copolymers thereof. In one embodiment, the hydrophobic region includes a poly(propylene oxide) polymer or copolymer.

In some embodiments, a hydrophilic region (the first hydrophilic region and/or the second hydrophilic region) includes a hydrophilic polymer, such as, but not limited to, poly(ethylene oxide), poly(N-isopropylacrylamide), polyacrylamide, poly(2-oxazoline), polyethylenimide, poly(acrylic acid), polymethacrylate, acrylic, poly(ethylene glycol), poly(ethylene oxide), poly(vinyl alcohol), poly(vinylpyrrolidone), maleic anhydride, and polyether polymers and copolymers thereof. In one embodiment, a hydrophilic region includes a poly(ethylene oxide) polymer or copolymer.

In some embodiments, the second hydrophilic region includes a handle moiety (extra-biological particle membrane anchor) which orients the second hydrophilic region to the extra-biological particle facing side of the membrane. In some embodiments, the second hydrophilic region includes a handle moiety (extracellular membrane anchor), which orients the second hydrophilic region to the extracellular side of a cell membrane. The handle moiety may include any moiety or molecule that is impermeable to and does not insert into a membrane. In some embodiments, the handle moiety may include an affinity moiety. For example, the affinity moiety may be a member of an affinity binding pair, such as, but not limited to, avidin, streptavidin, biotin, digoxigenin, a lectin, a carbohydrate, a lipid, an antibody or antibody-fragment thereof, an oligonucleotide, a receptor, or a receptor ligand. In some embodiments, the handle moiety may include a detectable label, such as, but not limited to, a radiolabel or a fluorophore, In some embodiments, the handle moiety may include a nanoparticle. In some embodiments, the handle moiety may include a protein or peptide. In some embodiments, the handle moiety may include a non-reactive or low affinity molecule.

When inserted into a biological particle membrane, the first hydrophilic regions of a plurality of block copolymer molecules as described herein serve as anchors on the intra-biological particle side of the membrane for formation of an internal polymer network. When inserted into a cell membrane, the first hydrophilic regions of a plurality of block copolymer molecules as described herein serve as anchors on the intracellular side of the membrane for formation of an internal polymer network. In some embodiments, bioorthogonal reactive monomers or oligomers, as described herein, may react with the bioorthogonal reactive moieties of the first hydrophilic regions of the block copolymers, and then sequentially react with each other to form the internal polymer network.

B. Monomers and Oligomers

Monomers and oligomers are provided that are capable of traversing a biological particle membrane and accumulating within a biological particle (e.g., inside of a continuous biological particle membrane, e.g., within the intra-biological particular region of a cell) and are capable of reacting with the bioorthogoonal reactive moiety of the first hydrophile region of the block copolymer, and with other monomers/oligomers within the biological particle to form an interior polymeric network within the intra-biological particular region of the biological particle. Optionally, monomers and oligomers react with a bioorthogonal moiety on the second hydrophilic region and form an exterior polymeric network on the outside of the biological particle. Monomers and oligomers are provided that are capable of traversing a cell membrane and accumulating within the cell (e.g., inside of a continuous cell membrane, e.g., within the intracellular region of a cell) and are capable of reacting with the bioorthogonal reactive moiety of the first hydrophilic region of the block copolymer, and with other monomers/oligomers within the cell to form an interior polymeric network within the intracellular region of the cell. Optionally, monomers/oligomers react with a bioorthogonal moiety on the second hydrophilic region and form an exterior polymeric network on the outside of the cell. Nonlimiting examples of monomers or oligomers that are suitable for use in the methods and systems described herein include amino acids, peptides (e.g., dipeptides), sugar molecules (e.g., sugar molecules that can be transported into the cell via cell membrane transporters but that are not compatible with cell metabolism), nucleosides, nucleotides, cell penetrating peptides/protein transduction domains, and toxins (e.g., cholera toxin). Chemical compound monomers or oligomers may also be used in the methods and systems described herein.

A monomer or oligomer as disclosed herein is capable of accumulation inside of an intact cell (e.g., can cross the cell membrane) and is capable of polymerization without degradation of or interference with biomolecules of interest or cell integrity (e.g., polymerization conditions and the final polymer network are not destructive to the structure and/or function of biomolecules of interest or destructive to cell integrity, e.g., integrity of cell architecture). In some embodiments, the final polymer network does not interfere with a desired application of use, such as, for example, single cell analysis, formation of a gel bead emulsion of single cells, reverse translation of RNA within a cell, determination of presence, absence, and/or quantity of a biomolecule of interest (e.g., RNA, DNA, protein, e.g., intracellular or cell surface protein, lipid), or spatial analysis (e.g., determination of presence, absence, quantity, and/or spatial location) of one or more analyte (e.g., biomolecule) of interest within a biological sample, such as a tissue sample.

A monomer or oligomer may include two or more bioorthogonal reactive moieties. For example, a monomer or oligomer may include 2, 3, 4, or more bioorthogonal reactive moieties. First and second monomers or oligomers, as described herein, may include the same or different number of bioorthogonal reactive moieties.

In some embodiments, a monomer or oligomer includes a plurality of bioorthogonal reactive moieties that are all the same or that contain the same functional group, such as, but not limited to, a plurality of azide or alkyne moieties. For example, first monomers may include a plurality of first bioorthogonal reactive moieties are capable of reacting with the bioorthogonal reactive moiety of the first hydrophilic region of the block copolymer, and second monomers may include a plurality of second bioorthogonal reactive moieties that are capable of reacting with the first bioorthogonal reactive moiety.

In other embodiments, monomers or oligomers may include both first and second different bioorthogonal reactive moieties (one or a plurality of first bioorthogonal reactive moiety and one or a plurality of second bioorthogonal reactive moiety), such as, but not limited to, azide and alkyne moieties, and the first bioorthogonal reactive moiety of the monomers or oligomers is capable of reacting with the bioorthogonal reactive moiety of the first hydrophilic region of the block copolymer and with the second bioorthogonal reactive moiety of other monomers or oligomers. of a monomer or oligomer is capable of reacting with the bioorthogonal reactive moiety of a first and/or second hydrophilic region of the block copolymer, and a second bioorthogonal reactive moiety of the monomer or oligomer is capable of reacting with the first bioorthogonal reactive moiety on another monomer or oligomer. For example, in one embodiment, a monomer or oligomer may include two bioorthogonal reactive moieties that are configured such that they do not react with each other but are capable of reacting with the bioorthogonal moiety of the first and/or second hydrophilic region of the block copolymer and with bioorthogonal moieties of other monomers/oligomers to form a polymer network. In an embodiment, a dimer, such as a dipeptide, disaccharide, etc. includes a first bioorthogonal reactive moiety on a first monomer of the dimer and a second bioorthogonal reactive moiety on a second monomer of the dimer, configured such that they do not react with each other in the dimer but are capable of reacting with the bioorthogonal moiety of the first and/or second hydrophilic region of the block copolymer and with bioorthogonal moieties of other dimers to form a polymer network.

Sequential reactions between first and second bioorthogonal reactive moieties of monomers or oligomers result in formation of a polymer network within a biological particle and/or on the outside of the biological particle membrane, under conditions suitable for polymerization. Sequential reactions between first and second bioorthogonal reactive moieties of monomers or oligomers result in formation of a polymer network within a cell and/or on the outside of the cell membrane, under conditions that are suitable for polymerization.

The polymer network formed by reaction of bioorthogonal moieties of monomers/oligomers may optionally be degradable (e.g., depolymerizable) by a second chemistry or by an enzyme. For example, in one nonlimiting embodiment, a dimer or oligomer that includes monomers joined by an ester-based chemical linkage may be depolymerized by an esterase enzyme. In a nonlimiting embodiment, the esterase may be temperature sensitive and may be doped into cells prior to a downstream application of use or into an environment surrounding the cells, such as into gel beads; a temperature increase for a downstream process such as reverse transcription could activate the enzyme, thus initiating or accelerating depolymerization of the polymer network.

C. Bioorthogonal Reactive Moieties

The first hydrophilic region, and optionally the second hydrophilic region, of the block copolymer, and monomers/oligomers, as described above, contain bioorthogonal reactive moieties. A bioorthogonal reactive moiety is capable of a chemical reaction that can occur within a living system (e.g., a cell) without disrupting a native biochemical process or degrading a native biomolecule (e.g., nucleic acid, polypeptide, lipid, carbohydrate, glycan), thus forming an intracellular polymer network, as described above.

A number of bioorthogonal reaction strategies are available, including, but not limited to, 1,3-dipolar cycloaddition between azides and cyclooctynes (copper-free click chemistry) (Baskin, J., et al. (2007) *Proc. Natl. Acad. Sci.* 104 (43):16793-16797) or between nitrones and cyclooctynes (Ning, X., et al. (2010) *Angewandte Chemie International Edition* 49(17):3065-3068), oxime/hydrazone formation from aldehydes and ketones (Yarema, K., et al. (1998) *J. Biol. Chem.* 273(47):31168-31179), tetrazine ligation (Blackman, M., et al. (2008) *Journal of the American ChemicalSociety* 130(41):13518-13519), isocyanide-based click reaction ([4+1]cycloaddition followed by a retro-Diels Alder elimination of $N_2$) (Stöckmann, H., et al. (2011) *Organic & Biomolecular Chemistry* 9(21):7303-7305), quadricyclane ligation (Sletten, E., et al., (2011) *Journal of the American Chemical Society* 133(44):17570-17573), Staudinger (azide-triarylphosphine) ligation (Saxon, E., et al. (2000) *Science* 287(5460):2007-2010), norbornene cycloaddition (nitrile oxide-norbornene) (Gutsmiedl, K., et al. (2009) *Organic Letters* 11(11):2405-2408), oxanorbornadiene cycloaddition (1,3-dipolar cycloaddition followed by a retro-Diels Alder reaction to generate a triazole-linked conjugate with the elimination of a furan molecule) (Van Berkel, S., et al. (2007) *Chem Bio Chem* 8(13): 1504-1508), and tetrazole photoclick chemistry (photoinduced cyclor-eversion to release $N_2$, generating a short-lived nitrile imine intermediate, which undergoes a 1,3-dipolar cycloaddition with an alkene to generate pyrazoline cycloadduct) (Stöckmann, H., et al. (2011) *Organic & Biomolecular Chemistry* 9(21):7303-7305)

Bioorthogonal reactions may include the following features: (1) Selectivity—avoids reaction with endogenous functional groups of biomolecules; (2) Biological inertness—does not disrupt bioprocesses; (3) Chemical inertness—covalent bond that is formed in the bioorthogonal reaction is strong and inert with respect to biological reactions; (4) Rapid kinetics—prevent competition from cellular processes; (5) Reaction compatibility—non-toxic to the cell and functioning under biological conditions, e.g., pH, aqueous environment, temperature.

The bioorthogonal moiety of the hydrophilic region and/or the monomers/oligomers may include, but is not limited to, an alkyne, an azide, a phosphine, a cyclooctyne, a nitrone, a norbornene, an oxanorbornadiene, a tetrazine, an isocyanide, a tetrazole, a quadricyclane, a nitrile imine, or an alkene. In some embodiments, the bioorthogonal moiety is an alkyne or an azide.

In methods described herein, polymerization conditions are not destructive to the biological particle architecture, the cell architecture or to biomolecule(s) of interest. Polymerization may include the use of a catalyst or may rely on features of the bioorthogonal reactive moieties, such as ring strain. Polymerization conditions that are compatible with cellular systems and processes, and preservation of biomolecular structures, are known in the art. (See, e.g., Azagarsamy, M., et al. (2013) *ACS Macro Lett.* 2:5-9; Zou, Y., et al. (2018) *Journal of Controlled Release* 273:160-179; Le Droumaguet, B., et al. (2008) *Macromol. Rapid Commun.* 29:1073-1089) In general, the reagents used should be nontoxic to cells, and the reaction should be unaffected by media or cellular components or functional groups. Nonlimiting examples of polymerization conditions include: strain-promoted azide-alkyne cycloaddition (SPAAC); base-catalyzed thiol-vinyl sulfone Michael addition; base-catalyzed thiol-maleimide Michael addition; and thermal or photoinitiated thiol-ene photocoupling.

Step-growth polymerization of monomers/oligomers as described herein occurs when bi-functional or multifunctional monomers/oligomers react sequentially, e.g., forming dimers of the monomers/oligomers, then trimers, then longer oligomers, and eventually long chain polymers. In nonlimiting embodiments, multifunctional first monomers/oligomers (i.e., with at least three first bioorthogonal reactive moiety groups, e.g., trifunctional, tetrafunctional, etc.) are reacted with bifunctional crosslinkers (i.e., bifunctional second monomers/oligomers with two second bioorthogonal reactive moiety groups), where the first and second bioorthogonal reactive moiety groups react covalently with each other (i.e., to form covalent bonds) in a sequential manner to form a step-growth polymeric network (e.g., hydrogel). The density and three-dimensional structure of the polymeric network may be varied by varying the density and configuration of bioorthogonal reactive moieties in the first and second monomers/oligomers.

In some embodiments, a Michael addition reaction is deployed. Typically, a Michael-type addition includes a base-catalyzed addition of a Michael donor, such as a thiol or amine) to an electrophilic carbon-carbon double bond conjugated to with a carbonyl group (i.e., a Michael acceptor). A large variety of Michael acceptors have been characterized for hydrogel formation, including acrylates, acrylamides, vinyl sulfones, and maleimides. Thiol-based Michael donors are widely used, due to their higher nucleophilicity and selectivity at physiological pH and temperature. (See, e.g., Elbert, D., et al. (2001) *J. Controlled Release* 76:11-25) Base-catalyzed Michael reactions may be managed by inclusion of buffering agents, such as triethanolamine (TEA) or HEPES. These basic buffers may be toxic to some cell types, for example, cells in ovarian follicles, and pancreatic islets). Maleimide-based Michael acceptors require much a much lower amount of TEA, thus reducing toxicity. (Phelps, E., et al. (2012) *J. Adv. Mater.* 24:64-70)

In some embodiments, a thiol-ene reaction is deployed, as a radically mediated step growth polymerization. Radicals are created either thermally or photochemically. In one nonlimiting embodiment, a multi-functional norbornene first monomer/oligomer (e.g., a 4-arm tetra-norbornene, such as a 4-arm PEG tetra-norbornene) may be reacted with a dicysteine-terminated (e.g., matrix metalloproteinase (MMP) and/or chymotrypsin cleavable) degradable peptide second monomer/oligomer. A step-growth polymeric network may be rapidly formed (e.g., in seconds to minutes) using a water-soluble photoinitiator, such as lithium phenyl-2,4,6-trimethylbenzoylphosphinate (LAP), and a 365-420 nm single photon light or 720 nm multiphoton light. (Fairbanks, B., et al. (2009) *Adv. Mater.* 21:5005-5010; DeForest, C., et al. (2009) *Nat. Mater.* 8:659-664) Variation of time of exposure, light intensity, initiator concentration, and stoichiometric ratio of reactive functional groups provides control over the physical structure and properties of the resulting polymeric network.

In some embodiments, an azide-alkyne cycloaddition reaction is deployed. To overcome cellular toxicity of a copper catalyst in driving the azide-alkyne reaction, strained molecules, e.g., strained alkynes (e.g., cyclooctynes) may be used, in a strain-promoted azide-alkyne cycloaddition (SPAAC) reaction. (Agard, N., et al. (2004) *J. Am. Chem. Soc.* 126:15046-15047) Strained alkynes rapidly react with azides without the need for a copper catalyst, and none of the functionalities in the reaction are reactive toward biological systems. (Sletten, E., et al. (2009) *Agnew. Chem., Int. Ed.* 48:6974-6998) In one nonlimiting embodiment, a multi-functional azide first monomer/oligomer (e.g., 4-arm tetra azide (such as a 4-arm PEG tetra azide) may be reacted with a dicyclooctyne-flanked (e.g., MMP cleavable) degradable peptide second monomer/oligomer. (DeForest, C., et al. (2009) *Nat. Mater.* 8:659-664; DeForest, C. et al. (2010) *S. Chem. Mater.* 22:4783-4790) In certain embodiments, a gem-difluoro cyclooctane may be used (DIFO), which exhibits faster reaction kinetics due to the presence of strong electron withdrawing fluorines in addition to the ring strain. (Codelli, J., et al. (2008) *J. Am. Chem. Soc.* 130:11486-11493) SPAAC-based polymer formation proceeds under physiological conditions and does not require additional reagents, such as buffers, initiators, or catalysts.

Copper-Free Click Chemistry

Copper-catalyzed azide-alkyne cycloaddition is an extremely fast and efficient reaction for bioconjugation, but it is not suitable for use with live cells due to toxicity of copper (Cu(I)) ions, which cause oxidative damage from reactive oxygen species formed by the copper catalyst. Copper complexes also induce changes in cellular metabolism. Copper-free click chemistry was developed as a non-toxic variant of this reaction. (Jewett, J., et al. (2010) *Chem Soc Rev* 39(4):1272-1279)

The azide group is bioorthogonal because it is extremely small, metabolically stable, and does not exist naturally in cells, thus having no competing biological side reactions. The alkyne group is not as small as an azide group, but it exhibits stability and bioorthogonality in cells. Cyclooctynes are often used; they are the smallest stable alkyne ring.

The reaction of an azide with an alkyne (e.g., cyclooctyne) is a 1,3-dipolar cycloaddition, an asynchronous, concerted pericyclic shift. Nonlimiting examples of cyclooctynes include:

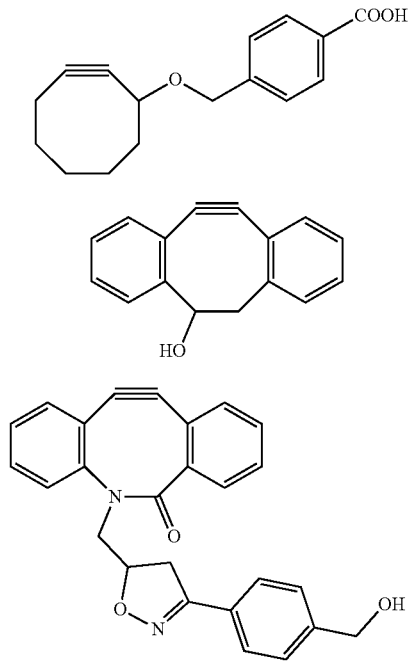

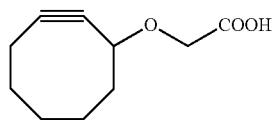

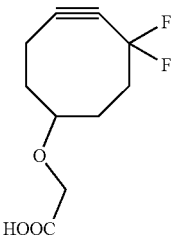

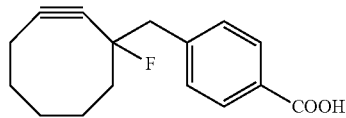

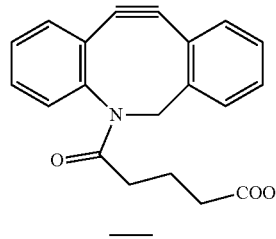

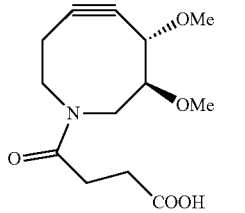

In some embodiments of the systems and methods described herein, the triblock copolymer and monomer/oligomer components contain azide and alkyne groups that react to form an internal polymer network within a biological particle. An azide or alkyne group on a first hydrophilic region of a triblock copolymer reacts with an alkyne group or azide group on a monomer/oligomer component, respectively, and monomer/oligomers contain azide and alkyne groups that further react to produce a polymer matrix within the biological particle.

In one embodiment, the first hydrophilic region, and optionally the second hydrophilic region of the triblock copolymer includes an alkyne group. In one embodiment, the triblock copolymer is an alkyne-modified membrane anchor, e.g., containing an alkyne group on the first hydrophilic region and a handle moiety on the second hydrophilic region.

In one embodiment the first hydrophilic region, and optionally the second hydrophilic region of the triblock copolymer includes an azide group. In one embodiment, the triblock copolymer is an azide-modified membrane anchor, e.g., containing an azide group on the first hydrophilic region and a handle moiety on the second hydrophilic region.

In one embodiment, a monomer/oligomer contains an azide group. In another embodiment, a monomer/oligomer contains an alkyne group. In another embodiment, a monomer/oligomer contains both an azide group and an alkyne group. In another embodiment, an oligomer is a dimer that contains both an azide group on one monomer of the dimer and an alkyne group on the other monomer of the dimer.

IV. Methods of Use

Methods are provided for stabilization of biological particles (e.g., cells, organelles) or biological samples, such as tissues, that contain cells. The stabilized biological particles (e.g., cells, organelles) or biological samples (e.g., tissues) may be used in a method for analysis of biomolecule(s) therein.

Biological particles or biological samples (e.g., tissues) are contacted with a plurality of block copolymers as described herein, which are polymerized to provide an intra-biological particle polymer network, and optionally an extra-biological particle polymer network. For example, monomers/oligomers as described herein that contain bioorthogonal reactive moieties may be used to form an intracellular polymer network, using the bioorthogonal reactive moiety of the intracellular first hydrophilic region of the block copolymer as a starting anchor for the intracellular polymer network. The second hydrophilic region of the block copolymer may contain a bioorthogonal reactive moiety, which may be polymerized to form an extracellular polymer network, or may contain a cell membrane impermeable moiety, which may optionally be used to sort and/or detect the cell into which it the block copolymer inserted.

Optionally, the polymer network may be depolymerized prior to analysis of biomolecule(s). Optionally, the stabilized cells or biological samples (e.g., tissues) may be treated with a fixative. Optionally, a stabilized tissue sample may be sectioned prior to analysis.

Fixed Samples

A sample may be a fixed sample. For example, a sample may comprise a plurality of fixed samples, such as a plurality of fixed cells or fixed nuclei. Alternatively or in addition, a sample may comprise a fixed tissue. Fixation of cell or cellular constituent, or a tissue comprising a plurality of cells or nuclei, may comprise application of a chemical species or chemical stimulus. The term "fixed" as used herein with regard to biological samples generally refers to the state of being preserved from decay and/or degradation. "Fixation" generally refers to a process that results in a fixed sample, and in some instances can include contacting the biomolecules within a biological sample with a fixative (or fixation reagent) for some amount of time, whereby the fixative results in covalent bonding interactions such as crosslinks between biomolecules in the sample. These crosslinks may involve linker molecules joining one or more biomolecules in the sample. A "fixed biological sample" may generally refer to a biological sample that has been contacted with a fixation reagent or fixative. For example, a formaldehyde-fixed biological sample has been contacted with the fixation reagent formaldehyde. "Fixed cells" or "fixed tissues" generally refer to cells or tissues that have been in contact with a fixative under conditions sufficient to allow or result in the formation of intra- and inter-molecular covalent crosslinks between biomolecules in the biological sample, including via a linker molecule. Generally, contact of biological sample (e.g., a cell or nucleus) with a fixation reagent (e.g., paraformaldehyde or PFA) results in the formation of intra- and inter-molecular covalent crosslinks between biomolecules in the biological sample. In some cases, provision of the fixation reagent, such as formaldehyde, may result in covalent aminal crosslinks within RNA, DNA, and/or protein molecules. For example, the widely used fixative reagent, paraformaldehyde or PFA, fixes tissue samples by catalyzing crosslink formation between basic amino acids in proteins, such as lysine and glutamine. Both intra-molecular and inter-molecular crosslinks can form in the protein. These crosslinks can preserve protein secondary structure and also eliminate enzymatic activity in the preserved tissue sample. Examples of fixation reagents include but are not limited to aldehyde fixatives (e.g., formaldehyde, also commonly referred to as "paraformaldehyde," "PFA," and "formalin"; glutaraldehyde; etc.), imidoesters, NHS (N-Hydroxysuccinimide) esters, and the like.

Other examples of fixation reagents include, for example, organic solvents such as alcohols (e.g., methanol or ethanol), ketones (e.g., acetone), and aldehydes (e.g., paraformaldehyde, formaldehyde (e.g., formalin), or glutaraldehyde). As described herein, cross-linking agents may also be used for fixation including, without limitation, disuccinimidyl suberate (DSS), dimethylsuberimidate (DMS), formalin, and dimethyladipimidate (DMA), dithio-bis(-succinimidyl propionate) (DSP), disuccinimidyl tartrate (DST), and ethylene glycol bis(succinimidyl succinate) (EGS). In some cases, a cross-linking agent may be a cleavable cross-linking agent (e.g., thermally cleavable, photocleavable, etc.). In some cases, more than one fixation reagent can be used in combination when preparing a fixed biological sample. Changes to a characteristic or a set of characteristics of a cell or cellular constituents (e.g., incurred upon interaction with one or more fixation agents) may be at least partially reversible (e.g., via rehydration or de-crosslinking). Alternatively, changes to a characteristic or set of characteristics of a cell or cellular constituents (e.g., incurred upon interaction with one or more fixation agents) may be substantially irreversible.

A. Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion or a well. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more beads. A partition may comprise one or more gel beads. A partition may include a single gel bead. A partition may include one or more reagents. Alternatively, a partition may be unoccupied. For example, a partition may not comprise a bead. Unique identifiers, such as barcodes, may be injected into the droplets previous to, subsequent to, or concurrently with droplet generation, such as via a particle (e.g., bead), as described elsewhere herein.

B. Droplet-Based Systems and Methods for Sample Compartmentalization

The methods and systems of the present disclosure may comprise methods and systems for generating one or more partitions such as droplets. The droplets may comprise a plurality of droplets in an emulsion. In some examples, the droplets may comprise droplets in a colloid. In some cases, the emulsion may comprise a microemulsion or a nanoemulsion. In some examples, the droplets may be generated with aid of a microfluidic device and/or by subjecting a mixture of immiscible phases to agitation (e.g., in a container). In some cases, a combination of the mentioned methods may be used for droplet and/or emulsion formation.

Droplets can be formed by creating an emulsion by mixing and/or agitating immiscible phases. Mixing or agitation may comprise various agitation techniques, such as vortexing, pipetting, tube flicking, or other agitation techniques. In some cases, mixing or agitation may be performed without using a microfluidic device. In some examples, the droplets may be formed by exposing a mixture to ultrasound or sonication. Systems and methods for droplet and/or emulsion generation by agitation are described in International Application No. PCT/US20/17785, which is entirely incorporated herein by reference for all purposes.

Microfluidic devices or platforms comprising microfluidic channel networks (e.g., on a chip) can be utilized to generate partitions such as droplets and/or emulsions as described herein. Methods and systems for generating partitions such as droplets, methods of encapsulating biological particle, methods of increasing the throughput of droplet generation, and various geometries, architectures, and configurations of microfluidic devices and channels are described in U.S. Patent Publication Nos. 2019/0367997 and 2019/0064173, each of which is entirely incorporated herein by reference for all purposes.

In some examples, individual particles can be partitioned to discrete partitions by introducing a flowing stream of particles in an aqueous fluid into a flowing stream or reservoir of a non-aqueous fluid, such that droplets may be generated at the junction of the two streams/reservoir, such as at the junction of a microfluidic device provided elsewhere herein.

The methods of the present disclosure may comprise generating partitions and/or encapsulating particles, such as biological particles, in some cases, individual biological particles such as single cells. In some examples, reagents may be encapsulated and/or partitioned (e.g., co-partitioned with biological particles) in the partitions. Various mechanisms may be employed in the partitioning of individual particles. An example may comprise porous membranes through which aqueous mixtures of cells may be extruded into fluids (e.g., non-aqueous fluids).

The partitions can be flowable within fluid streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (such as cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

As will be appreciated, the above-described occupancy rates are also applicable to partitions that include both biological particles and additional reagents, such as particles or beads (e.g., gel beads) carrying barcoded nucleic acid molecules (e.g., oligonucleotides). In some cases, the occupied partitions (e.g., at least about 10%, 20%, 30%, 40%, 50%, 60%, 70%, 80%, 90%, 95%, or 99% of the occupied partitions) may comprise both a particle (e.g., bead) comprising barcoded nucleic acid molecules and a biological particle.

Figure 9:
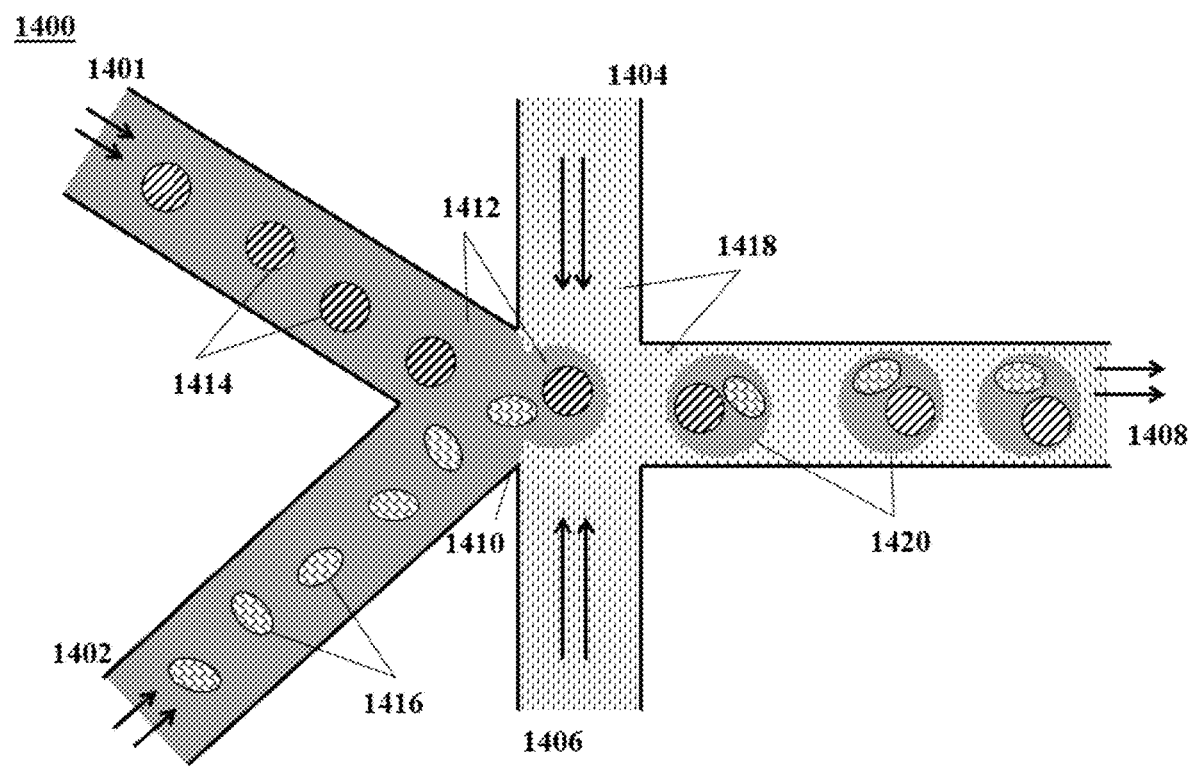
FIG. 9 depicts an exemplary microfluidic channel structure for delivering barcode carrying beads to droplets.

FIG. 9 shows an example of a microfluidic channel structure 1400 for delivering beads and/or biological particles to droplets. The channel structure 1400 can include channel segments 1401, 1402, 1404, 1406 and 1408 communicating at a channel junction 1410. In operation, the channel segment 1401 may transport an aqueous fluid 1412 that includes a plurality of beads 1414 (e.g., with nucleic acid molecules, e.g., nucleic acid barcode molecules or barcoded oligonucleotides, molecular tags) along the channel segment 1401 into junction 1410. The plurality of beads 1414 may be sourced from a suspension of beads. For example, the channel segment 1401 may be connected to a reservoir comprising an aqueous suspension of beads 1414. The channel segment 1402 may transport the aqueous fluid 1412 that includes a plurality of biological particles 1416 along the channel segment 1402 into junction 1410. The plurality of biological particles 1416 may be sourced from a suspension of biological particles. For example, the channel segment 1402 may be connected to a reservoir comprising an aqueous suspension of biological particles 1416. In some instances, the aqueous fluid 1412 in either the first channel segment 1401 or the second channel segment 1402, or in both segments, can include one or more reagents, as further described below. A second fluid 1418 that is immiscible with the aqueous fluid 1412 (e.g., oil) can be delivered to the junction 1410 from each of channel segments 1404 and 1406. Upon meeting of the aqueous fluid 1412 from each of channel segments 1401 and 1402 and the second fluid 1418 from each of channel segments 1404 and 1406 at the channel junction 1410, the aqueous fluid 1412 can be partitioned as discrete droplets 1420 in the second fluid 1418 and flow away from the junction 1410 along channel segment 1408. The channel segment 1408 may deliver the discrete droplets to an outlet reservoir fluidly coupled to the channel segment 1408, where they may be harvested. As an alternative, the channel segments 1401 and 1402 may meet at another junction upstream of the junction 1410. At such junction, beads and biological particles may form a mixture that is directed along another channel to the junction 1410 to yield droplets 1420. The mixture may provide the beads and biological particles in an alternating fashion, such that, for example, a droplet comprises a single bead and a single biological particle.

Figure 2:
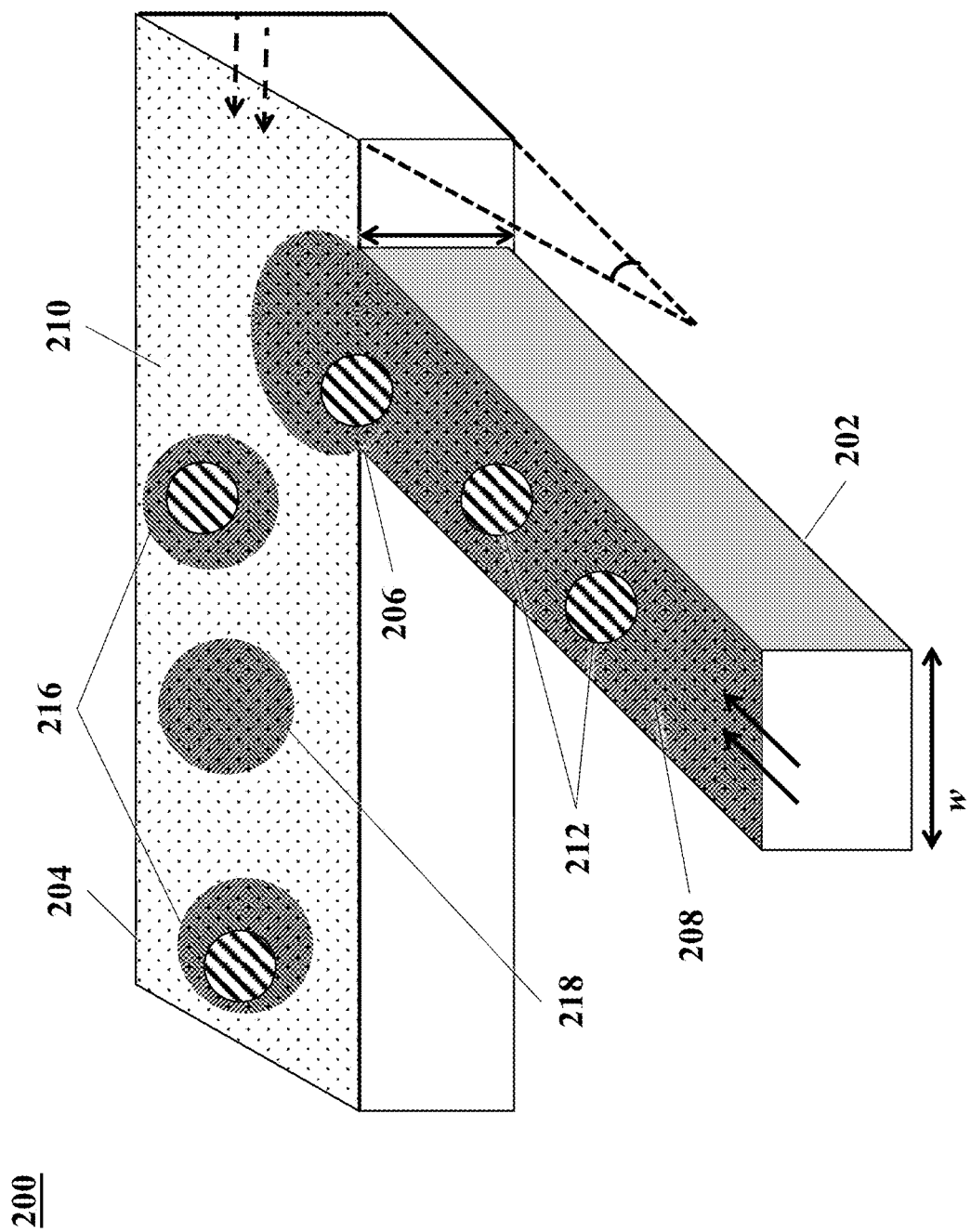
FIG. 2 shows an example of a microfluidic channel structure for the controlled partitioning of beads into discrete droplets.

FIG. 2 shows an example of a microfluidic channel structure 200 for delivering beads (e.g., barcode carrying beads) and/or biological particles to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

In some examples, beads, biological particles, and droplets may flow along channels (e.g., the channels of a microfluidic device). Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220. A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Systems and methods for controlled partitioning are described further in WO2019040637, which is hereby incorporated by reference in its entirety.

C. Well-Based Systems and Methods for Sample Compartmentalization

As described herein, one or more processes may be performed in a partition, which may be a well. The well may be a well of a plurality of wells of a substrate, such as a microwell of a microwell array or plate, or the well may be a microwell or microchamber of a device (e.g., microfluidic device) comprising a substrate. The well may be a well of a well array or plate, or the well may be a well or chamber of a device (e.g., fluidic device). In some embodiments, a well of a fluidic device is fluidically connected to another well of the fluidic device. Accordingly, the wells or microwells may assume an "open" configuration, in which the wells or microwells are exposed to the environment (e.g., contain an open surface) and are accessible on one planar face of the substrate, or the wells or microwells may assume a "closed" or "sealed" configuration, in which the microwells are not accessible on a planar face of the substrate. In some instances, the wells or microwells may be configured to toggle between "open" and "closed" configurations. For instance, an "open" microwell or set of microwells may be "closed" or "sealed" using a membrane (e.g., semi-permeable membrane), an oil (e.g., fluorinated oil to cover an aqueous solution), or a lid, as described elsewhere herein. A fluidic device may be selected from the group comprising nanopens.

The well may have a volume of less than 1 milliliter (mL). For instance, the well may be configured to hold a volume of at most 1000 microliters (μL), at most 100 μL, at most 10 μL, at most 1 μL, at most 100 nanoliters (nL), at most 10 nL, at most 1 nL, at most 100 picoliters (pL), at most 10 (pL), or less. The well may be configured to hold a volume of about 1000 μL, about 100 μL, about 10 μL, about 1 μL, about 100 nL, about 10 nL, about 1 nL, about 100 pL, about 10 pL, etc. The well may be configured to hold a volume of at least 10 pL, at least 100 pL, at least 1 nL, at least 10 nL, at least 100 nL, at least 1 μL, at least 10 μL, at least 100 μL, at least 1000 μL, or more. The well may be configured to hold a volume in a range of volumes listed herein, for example, from about 5 nL to about 20 nL, from about 1 nL to about 100 nL, from about 500 pL to about 100 pL, etc. The well may be of a plurality of wells that have varying volumes and may be configured to hold a volume appropriate to accommodate any of the partition volumes described herein.

In some instances, a microwell array or plate comprises a single variety of microwells. In some instances, a microwell array or plate comprises a variety of microwells. For instance, the microwell array or plate may comprise one or more types of microwells within a single microwell array or plate. The types of microwells may have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate may comprise any number of different types of microwells. For example, the microwell array or plate may comprise 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well may have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate comprises different types of microwells that are located adjacent to one another within the array or plate. For instance, a microwell with one set of dimensions may be located adjacent to and in contact with another microwell with a different set of dimensions. Similarly, microwells of different geometries may be placed adjacent to or in contact with one another. The adjacent microwells may be configured to hold different articles; for example, one microwell may be used to contain a cell, cell bead, or other sample (e.g., cellular components, nucleic acid molecules, etc.) while the adjacent microwell may be used to contain a microcapsule, droplet, bead, or other reagent. In some cases, the adjacent microwells may be configured to merge the contents held within, e.g., upon application of a stimulus, or spontaneously, upon contact of the articles in each microwell.

As is described elsewhere herein, a plurality of partitions may be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000,000 wells, at least about 500,000,000 wells, at least about 1,000,000,000 wells, or more wells can be generated or otherwise provided. Moreover, the plurality of wells may comprise both unoccupied wells (e.g., empty wells) and occupied wells.

A well may comprise any of the reagents described herein, or combinations thereof. These reagents may include, for example, barcode molecules, enzymes, adapters, and combinations thereof. The reagents may be physically separated from a sample (e.g., a cell, cell bead, or cellular components, e.g., proteins, nucleic acid molecules, etc.) that is placed in the well. This physical separation may be accomplished by containing the reagents within, or coupling to, a microcapsule or bead that is placed within a well. The physical separation may also be accomplished by dispensing the reagents in the well and overlaying the reagents with a layer that is, for example, dissolvable, meltable, or permeable prior to introducing the polynucleotide sample into the well. This layer may be, for example, an oil, wax, membrane (e.g., semi-permeable membrane), or the like. The well may be sealed at any point, for example, after addition of the microcapsule or bead, after addition of the reagents, or after addition of either of these components. The sealing of the well may be useful for a variety of purposes, including preventing escape of beads or loaded reagents from the well, permitting select delivery of certain reagents (e.g., via the use of a semi-permeable membrane), for storage of the well prior to or following further processing, etc.

Once sealed, the well may be subjected to conditions for further processing of a cell (or cells) in the well. For instance, reagents in the well may allow further processing of the cell, e.g., cell lysis, as further described herein. Alternatively, the well (or wells such as those of a well-based array) comprising the cell (or cells) may be subjected to freeze-thaw cycling to process the cell (or cells), e.g., cell lysis. The well containing the cell may be subjected to freezing temperatures (e.g., 0° C., below 0° C., −5° C., −10° C., −15° C., −20° C., −25° C., −30° C., −35° C., −40° C., −45° C., −50° C., −55° C., −60° C., −65° C., −70° C., −80° C., or −85° C.). Freezing may be performed in a suitable manner, e.g., sub-zero freezer or a dry ice/ethanol bath. Following an initial freezing, the well (or wells) comprising the cell (or cells) may be subjected to freeze-thaw cycles to lyse the cell (or cells). In one embodiment, the initially frozen well (or wells) are thawed to a temperature above freezing (e.g., 4° C. or above, 8° C. or above, 12° C. or above, 16° C. or above, 20° C. or above, room temperature, or 25° C. or above). In another embodiment, the freezing is performed for less than 10 minutes (e.g., 5 minutes or 7 minutes) followed by thawing at room temperature for less than 10 minutes (e.g., 5 minutes or 7 minutes). This freeze-thaw cycle may be repeated a number of times, e.g., 2, 3, 4 or more times, to obtain lysis of the cell (or cells) in the well (or wells). In one embodiment, the freezing, thawing and/or freeze/thaw cycling is performed in the absence of a lysis buffer. Additional disclosure related to freeze-thaw cycling is provided in WO2019165181A1, which is incorporated herein by reference in its entirety.

A well may comprise free reagents and/or reagents encapsulated in, or otherwise coupled to or associated with, microcapsules, beads, or droplets. Any of the reagents described in this disclosure may be encapsulated in, or otherwise coupled to, a microcapsule, droplet, or bead, with any chemicals, particles, and elements suitable for sample processing reactions involving biomolecules, such as, but not limited to, nucleic acid molecules and proteins. For example, a bead or droplet used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, oligonucleotides, nucleotides, deoxyribonucleotide triphosphates (dNTPs), dideoxyribonucleotide triphosphates (ddNTPs), DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, polymerase, ligase, restriction enzymes, proteases, nucleases, protease inhibitors, nuclease inhibitors, chelating agents, reducing agents, oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds. As described herein, one or more reagents in the well may be used to perform one or more reactions, including but not limited to: cell lysis, cell fixation, permeabilization, nucleic acid reactions, e.g., nucleic acid extension reactions, amplification, reverse transcription, transposase reactions (e.g., tagmentation), etc.

The wells may be provided as a part of a kit. For example, a kit may comprise instructions for use, a microwell array or device, and reagents (e.g., beads). The kit may comprise any useful reagents for performing the processes described herein, e.g., nucleic acid reactions, barcoding of nucleic acid molecules, sample processing (e.g., for cell lysis, fixation, and/or permeabilization).

In some cases, a well comprises a microcapsule, bead, or droplet that comprises a set of reagents that has a similar attribute (e.g., a set of enzymes, a set of minerals, a set of oligonucleotides, a mixture of different barcode molecules, a mixture of identical barcode molecules). In other cases, a microcapsule, bead, or droplet comprises a heterogeneous mixture of reagents. In some cases, the heterogeneous mixture of reagents can comprise all components necessary to perform a reaction. In some cases, such mixture can comprise all components necessary to perform a reaction, except for 1, 2, 3, 4, 5, or more components necessary to perform a reaction. In some cases, such additional components are contained within, or otherwise coupled to, a different microcapsule, droplet, or bead, or within a solution within a partition (e.g., microwell) of the system.

Figure 5:
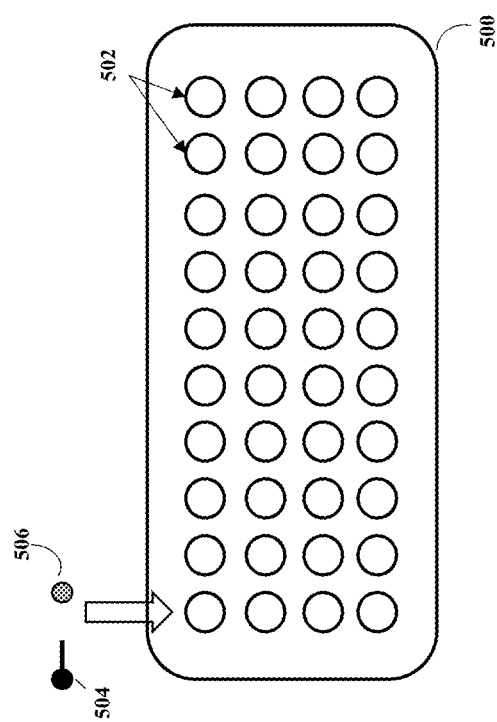
FIG. 5 schematically illustrates an example microwell array.

FIG. 5 schematically illustrates an example of a microwell array. The array can be contained within a substrate 500.

The substrate 500 comprises a plurality of wells 502. The wells 502 may be of any size or shape, and the spacing between the wells, the number of wells per substrate, as well as the density of the wells on the substrate 500 can be modified, depending on the particular application. In one such example application, a sample molecule 506, which may comprise a cell or cellular components (e.g., nucleic acid molecules) is co-partitioned with a bead 504, which may comprise a nucleic acid barcode molecule coupled thereto. The wells 502 may be loaded using gravity or other loading technique (e.g., centrifugation, liquid handler, acoustic loading, optoelectronic, etc.). In some instances, at least one of the wells 502 contains a single sample molecule 506 (e.g., cell) and a single bead 504.

Reagents may be loaded into a well either sequentially or concurrently. In some cases, reagents are introduced to the device either before or after a particular operation. In some cases, reagents (which may be provided, in certain instances, in microcapsules, droplets, or beads) are introduced sequentially such that different reactions or operations occur at different steps. The reagents (or microcapsules, droplets, or beads) may also be loaded at operations interspersed with a reaction or operation step. For example, microcapsules (or droplets or beads) comprising reagents for fragmenting polynucleotides (e.g., restriction enzymes) and/or other enzymes (e.g., transposases, ligases, polymerases, etc.) may be loaded into the well or plurality of wells, followed by loading of microcapsules, droplets, or beads comprising reagents for attaching nucleic acid barcode molecules to a sample nucleic acid molecule. Reagents may be provided concurrently or sequentially with a sample, e.g., a cell or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a microcapsule, bead, or droplet. These microcapsules, beads, or droplets may be loaded into a partition (e.g., a microwell) before, after, or concurrently with the loading of a cell, such that each cell is contacted with a different microcapsule, bead, or droplet. This technique may be used to attach a unique nucleic acid barcode molecule to nucleic acid molecules obtained from each cell. Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell, cell bead, or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell) and a single bead (such as those described herein, which may, in some instances, also be encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where intact or live cells are loaded in the microwells, one of the droplets may comprise lysis reagents for lysing the cell upon droplet merging.

A droplet or microcapsule may be partitioned into a well. The droplets may be selected or subjected to pre-processing prior to loading into a well. For instance, the droplets may comprise cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecules may be attached to a droplet or bead that has been partitioned into the well. The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. In some instances, the nucleic acid barcode molecules may be releasable from the bead or droplet. For instance, the nucleic acid barcode molecules may comprise a chemical cross-linker which may be cleaved upon application of a stimulus (e.g., photo-, magnetic, chemical, biological, stimulus). The nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell, cell bead, or cellular components) or derivatives thereof. Characterization techniques such as microscopy or imaging may be useful in measuring sample profiles in fixed spatial locations. For instance, when cells are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, etc. In some instances, imaging may be used to characterize live cells in the wells, including, but not limited to: dynamic live-cell tracking, cell-cell interactions (when two or more cells are co-partitioned), cell proliferation, etc. Alternatively or in addition to, imaging may be used to characterize a quantity of amplification products in the well.

In operation, a well may be loaded with a sample and reagents, simultaneously or sequentially. When cells or cell beads are loaded, the well may be subjected to washing, e.g., to remove excess cells from the well, microwell array, or plate. Similarly, washing may be performed to remove excess beads or other reagents from the well, microwell array, or plate. In the instances where live cells are used, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 6:
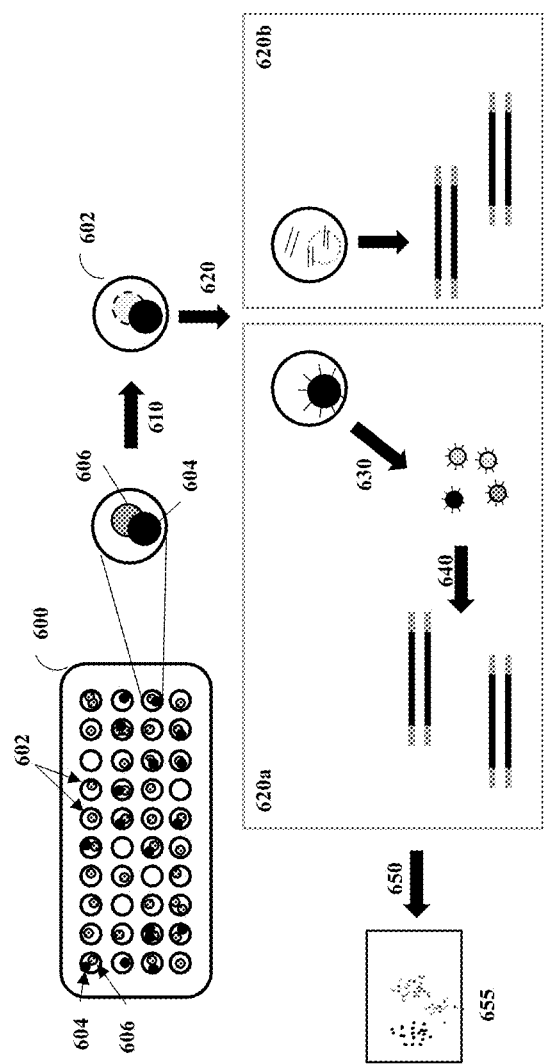
FIG. 6 schematically illustrates an example workflow for processing nucleic acid molecules.
Figure 7B:
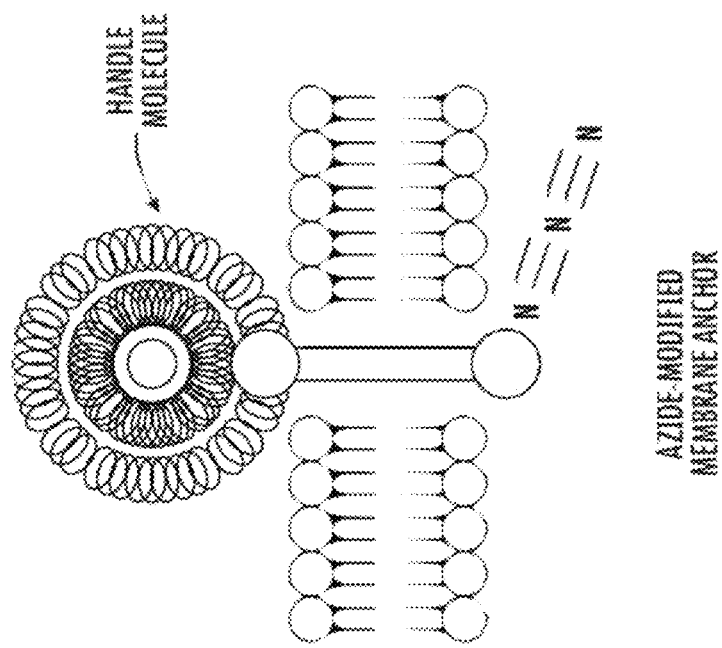
FIGS. 7A-7B depict examples of triblock copolymers with a hydrophobic region inserted into a cell membrane, a first hydrophilic region that includes a bioorthogonal reactive moiety, an alkyne moiety (FIG. 7A) or an azide moiety (FIG. 7B), and a second hydrophilic region that contains a cell membrane impermeable handle molecule.
Figure 7A:
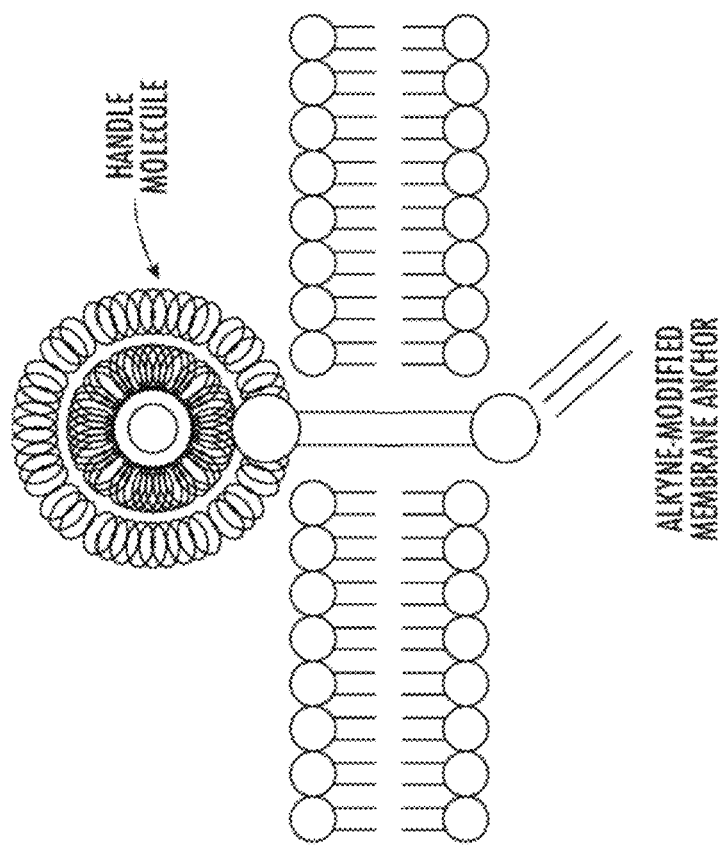
Figure 8:
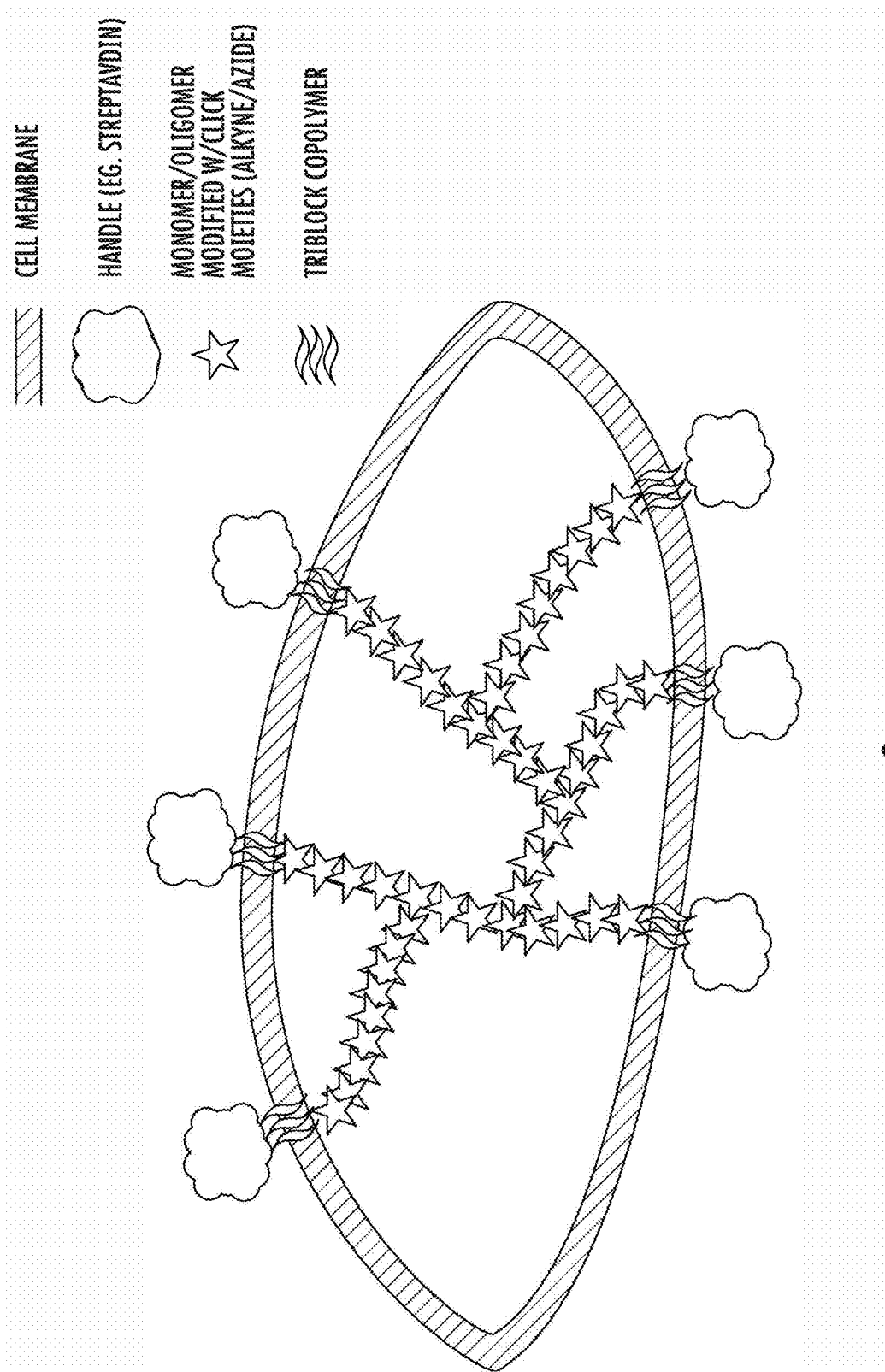
FIG. 8 depicts triblock copolymers inserted into a cell membrane and polymerized with monomers/oligomers to form an polymer network on the inside of the cell.

FIG. 6 schematically shows an example workflow for processing nucleic acid molecules within a sample. A substrate 600 comprising a plurality of microwells 602 may be provided. A sample 606 which may comprise a cell, cell bead, cellular components or analytes (e.g., proteins and/or nucleic acid molecules) can be co-partitioned, in a plurality of microwells 602, with a plurality of beads 604 comprising nucleic acid barcode molecules. During process 610, the sample 606 may be processed within the partition. For instance, in the case of live cells, the cell may be subjected to conditions sufficient to lyse the cells and release the analytes contained therein. In process 620, the bead 604 may be further processed. By way of example, processes 620a and 620b schematically illustrate different workflows, depending on the properties of the bead 604.

In 620a, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 630, the beads 604 from multiple wells 602 may be collected and pooled. Further processing may be performed in process 640. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

In 620b, the bead comprises nucleic acid barcode molecules that are releasably attached thereto, as described below. The bead may degrade or otherwise release the nucleic acid barcode molecules into the well 602; the nucleic acid barcode molecules may then be used to barcode nucleic acid molecules within the well 602. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

D. Nucleic Acid Barcode Molecules

Nucleic acid barcode molecules may be delivered to a partition (e.g., a droplet or well). Such nucleic acid barcode molecules may be delivered to the partition via a solid support or carrier (e.g., a bead). In some cases, nucleic acid barcode molecules are initially associated with the solid support and then released from the solid support upon application of a stimulus, which allows the nucleic acid barcode molecules to dissociate or to be released from the solid support. In specific examples, nucleic acid barcode molecules are initially associated with the solid support (e.g., bead) and then released from the solid support upon application of a biological stimulus, a chemical stimulus, a thermal stimulus, an electrical stimulus, a magnetic stimulus, and/or a photo stimulus.

A nucleic acid barcode molecule may contain a barcode sequence and a functional sequence, such as a nucleic acid primer sequence or a template switch oligonucleotide (TSO) sequence.

The solid support may be a bead. A solid support, e.g., a bead, may be porous, non-porous, hollow (e.g., a microcapsule), solid, semi-solid, and/or a combination thereof. Beads may be solid, semi-solid, semi-fluidic, fluidic, and/or a combination thereof. In some instances, a solid support, e.g., a bead, may be at least partially dissolvable, disruptable, and/or degradable. In some cases, a solid support, e.g., a bead, may not be degradable. In some cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In some cases, the solid support, e.g., the bead, may be a silica bead. In some cases, the solid support, e.g., a bead, can be rigid. In other cases, the solid support, e.g., a bead, may be flexible and/or compressible.

A partition may comprise one or more unique identifiers, such as barcodes. Barcodes may be previously, subsequently or concurrently delivered to the partitions that hold the compartmentalized or partitioned biological particle. For example, barcodes may be injected into droplets or deposited in microwells previous to, subsequent to, or concurrently with droplet generation or providing of reagents in the microwells, respectively. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a bead. Beads are described in further detail below.

In some cases, barcoded nucleic acid molecules can be initially associated with the bead and then released from the bead. Release of the barcoded nucleic acid molecules can be passive (e.g., by diffusion out of the bead). In addition or alternatively, release from the bead can be upon application of a stimulus which allows the barcoded nucleic acid nucleic acid molecules to dissociate or to be released from the bead. Such stimulus may disrupt the bead, an interaction that couples the barcoded nucleic acid molecules to or within the bead, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof. Methods and systems for partitioning barcode carrying beads into droplets are provided in US. Patent Publication Nos. 2019/0367997 and 2019/0064173, and International Application No. PCT/US20/17785, each of which is herein entirely incorporated by reference for all purposes.

In some examples, beads, biological particles, and droplets may flow along channels (e.g., the channels of a microfluidic device), in some cases at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

A bead may be porous, non-porous, solid, semi-solid, semi-fluidic, fluidic, and/or a combination thereof. In some instances, a bead may be dissolvable, disruptable, and/or degradable. Degradable beads, as well as methods for degrading beads, are described in PCT/US2014/044398, which is hereby incorporated by reference in its entirety. In some cases, any combination of stimuli, e.g., stimuli described in PCT/US2014/044398 and US Patent Application Pub. No. 2015/0376609, hereby incorporated by reference in its entirety, may trigger degradation of a bead. For example, a change in pH may enable a chemical agent (e.g., DTT) to become an effective reducing agent.

In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer ($\mu$m), 5 $\mu$m, 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 250 $\mu$m, 500 $\mu$m, 1 mm, or greater. In some cases, a bead may have a diameter of less than about 10 nm, 100 nm, 500 nm, 1 $\mu$m, 5 $\mu$m, 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 250 $\mu$m, 500 $\mu$m, 1 mm, or less. In some cases, a bead may have a diameter in the range of about 40-75 $\mu$m, 30-75 $\mu$m, 20-75 $\mu$m, 40-85 $\mu$m, 40-95 $\mu$m, 20-100 $\mu$m, 10-100 $\mu$m, 1-100 $\mu$m, 20-250 $\mu$m, or 20-500 $\mu$m.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers.

See, e.g., PCT/US2014/044398, which is hereby incorporated by reference in its entirety. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

In some cases, a plurality of nucleic acid barcode molecules may be attached to a bead. The nucleic acid barcode molecules may be attached directly or indirectly to the bead. In some cases, the nucleic acid barcode molecules may be covalently linked to the bead. In some cases, the nucleic acid barcode molecules are covalently linked to the bead via a linker. In some cases, the linker is a degradable linker. In some cases, the linker comprises a labile bond configured to release said nucleic acid barcode molecule of said plurality of nucleic acid barcode molecules. In some cases, the labile bond comprises a disulfide linkage. Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

Activation of disulfide linkages within a bead can be controlled such that only a small number of disulfide linkages are activated. Methods of controlling activation of disulfide linkages within a bead are described in PCT/US2014/044398, WO2014210353, which is hereby incorporated by reference in its entirety. In some cases, chitosan, a linear polysaccharide polymer, may be crosslinked with glutaraldehyde via hydrophilic chains to form a bead. Cross-linking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid barcode molecules (e.g., barcode sequence, nucleic acid barcode molecule, barcoded oligonucleotide, primer, or other oligonucleotide) to the bead. Acrydite moieties, as well as their uses in attaching nucleic acid molecules to beads, are described in PCT/US2014/044398, which is hereby incorporated by reference in its entirety.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule, e.g., a nucleic acid barcode molecule described herein.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. Exemplary precursors comprising functional groups are described in PCT/US2014/044398, which is hereby incorporated by reference in its entirety.

Other non-limiting examples of labile bonds that may be coupled to a precursor or bead are described in PCT/US2014/044398, which is hereby incorporated by reference in its entirety. A bond may be cleavable via other nucleic acid molecule targeting enzymes, such as restriction enzymes (e.g., restriction endonucleases), as described further below.

A nucleic acid barcode molecule may contain one or more barcode sequences. A plurality of nucleic acid barcode molecules may be coupled to a bead. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

Nucleic acid barcode molecules can comprise one or more functional sequences for coupling to an analyte or analyte tag such as a reporter oligonucleotide. Such functional sequences can include, e.g., a template switch oligonucleotide (TSO) sequence, a primer sequence (e.g., a poly T sequence, or a nucleic acid primer sequence complementary to a target nucleic acid sequence and/or for amplifying a target nucleic acid sequence, a random primer, and a primer sequence for messenger RNA).

In some cases, the nucleic acid molecule can further comprise a unique molecular identifier (UMI). In some cases, the nucleic acid barcode molecule can comprise one or more functional sequences, for example, for attachment to a sequencing flow cell, such as, for example, a P5 sequence (or a portion thereof) for Illumina® sequencing. In some cases, the nucleic acid barcode molecule or derivative thereof (e.g., oligonucleotide or polynucleotide generated from the nucleic acid molecule) can comprise another functional sequence, such as, for example, a P7 sequence (or a portion thereof) for attachment to a sequencing flow cell for Illumina sequencing. In some cases, the nucleic acid molecule can comprise an R1 primer sequence for Illumina sequencing. In some cases, the nucleic acid molecule can comprise an R2 primer sequence for Illumina sequencing. In some cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In some cases, a downstream procedure may extend the partial sequence, or derivative thereof, to achieve a full sequence of the partial sequence, or derivative thereof. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 3:
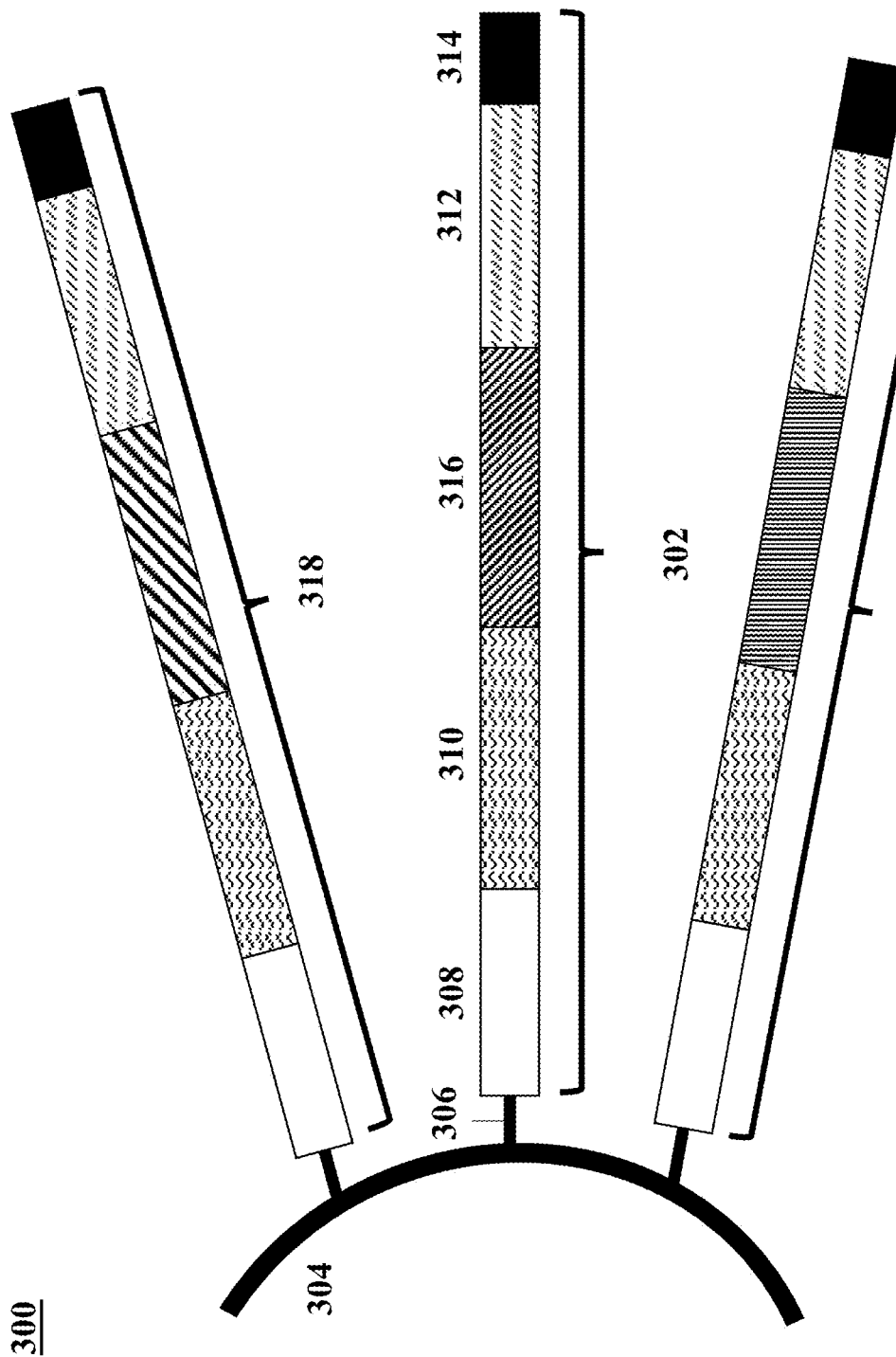
FIG. 3 illustrates an example of a barcode carrying bead.

FIG. 3 illustrates an example of a barcode carrying bead. A nucleic acid molecule 302, such as an oligonucleotide, can be coupled to a bead 304 by a releasable linkage 306, such as, for example, a disulfide linker. The same bead 304 may be coupled (e.g., via releasable linkage) to one or more other nucleic acid molecules 318, 320. The nucleic acid molecule 302 may be or comprise a barcode. As noted elsewhere herein, the structure of the barcode may comprise a number of sequence elements. The nucleic acid molecule 302 may comprise a functional sequence 308 that may be used in subsequent processing. For example, the functional sequence 308 may include one or more of a sequencer specific flow cell attachment sequence (e.g., a P5 sequence for Illumina® sequencing systems) and a sequencing primer sequence (e.g., a R1 primer for Illumina® sequencing systems), or partial sequence(s) thereof. The nucleic acid molecule 302 may comprise a barcode sequence 310 for use in barcoding the sample (e.g., DNA, RNA, protein, etc.). In some cases, the barcode sequence 310 can be bead-specific such that the barcode sequence 310 is common to all nucleic acid molecules (e.g., including nucleic acid molecule 302) coupled to the same bead 304. Alternatively or in addition, the barcode sequence 310 can be partition-specific such that the barcode sequence 310 is common to all nucleic acid molecules coupled to one or more beads that are partitioned into the same partition. The nucleic acid molecule 302 may comprise a specific priming sequence 312, such as an mRNA specific priming sequence (e.g., poly-T sequence), a targeted priming sequence, and/or a random priming sequence. The nucleic acid molecule 302 may comprise an anchoring sequence 314 to ensure that the specific priming sequence 312 hybridizes at the sequence end (e.g., of the mRNA). For example, the anchoring sequence 314 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 302 may comprise a unique molecular identifying sequence 316 (e.g., unique molecular identifier (UMI)). In some cases, the unique molecular identifying sequence 316 may comprise from about 5 to about 8 nucleotides. Alternatively, the unique molecular identifying sequence 316 may compress less than about 5 or more than about 8 nucleotides. The unique molecular identifying sequence 316 may be a unique sequence that varies across individual nucleic acid molecules (e.g., 302, 318, 320, etc.) coupled to a single bead (e.g., bead 304). In some cases, the unique molecular identifying sequence 316 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 3 shows three nucleic acid molecules 302, 318, 320 coupled to the surface of the bead 304, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 308, 310, 312, etc.) and variable or unique sequence segments (e.g., 316) between different individual nucleic acid molecules coupled to the same bead.

In operation, a biological particle (e.g., cell, DNA, RNA, etc.) can be co-partitioned along with a barcode bearing bead 304. The nucleic acid barcode molecules 302, 318, 320 can be released from the bead 304 in the partition. By way of example, in the context of analyzing sample RNA, the poly-T segment (e.g., 312) of one of the released nucleic acid molecules (e.g., 302) can hybridize to the poly-A tail of a mRNA molecule. Reverse transcription may result in a cDNA transcript of the mRNA, but which transcript includes each of the sequence segments 308, 310, 316 of the nucleic acid molecule 302. Because the nucleic acid molecule 302 comprises an anchoring sequence 314, it will more likely hybridize to and prime reverse transcription at the sequence end of the poly-A tail of the mRNA. Within any given partition, all of the cDNA transcripts of the individual mRNA molecules may include a common barcode sequence segment 310. However, the transcripts made from the different mRNA molecules within a given partition may vary at the unique molecular identifying sequence 312 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing).

The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where analytes from the sample are captured by the nucleic acid barcode molecules in a partition (e.g., by hybridization), captured analytes from various partitions may be collected, pooled, and subjected to further processing (e.g., reverse transcription, adapter attachment, amplification, clean up, sequencing). For example, in cases wherein the nucleic acid molecules from the sample remain attached to the bead, the beads from various partitions may be collected, pooled, and subjected to further processing (e.g., reverse transcription, adapter attachment, amplification, clean up, sequencing). In other instances, one or more of the processing methods, e.g., reverse transcription, may occur in the partition. For example, conditions sufficient for barcoding, adapter attachment, reverse transcription, or other nucleic acid processing operations may be provided in the partition and performed prior to clean up and sequencing.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc.

A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte.

In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, an biological particle (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead. In some instances, a capture sequence coupled to a bead (or other support) may be configured to attach to a linker molecule, such as a splint molecule, wherein the linker molecule is configured to couple the bead (or other support) to other molecules through the linker molecule, such as to one or more analytes or one or more other linker molecules.

Figure 4:
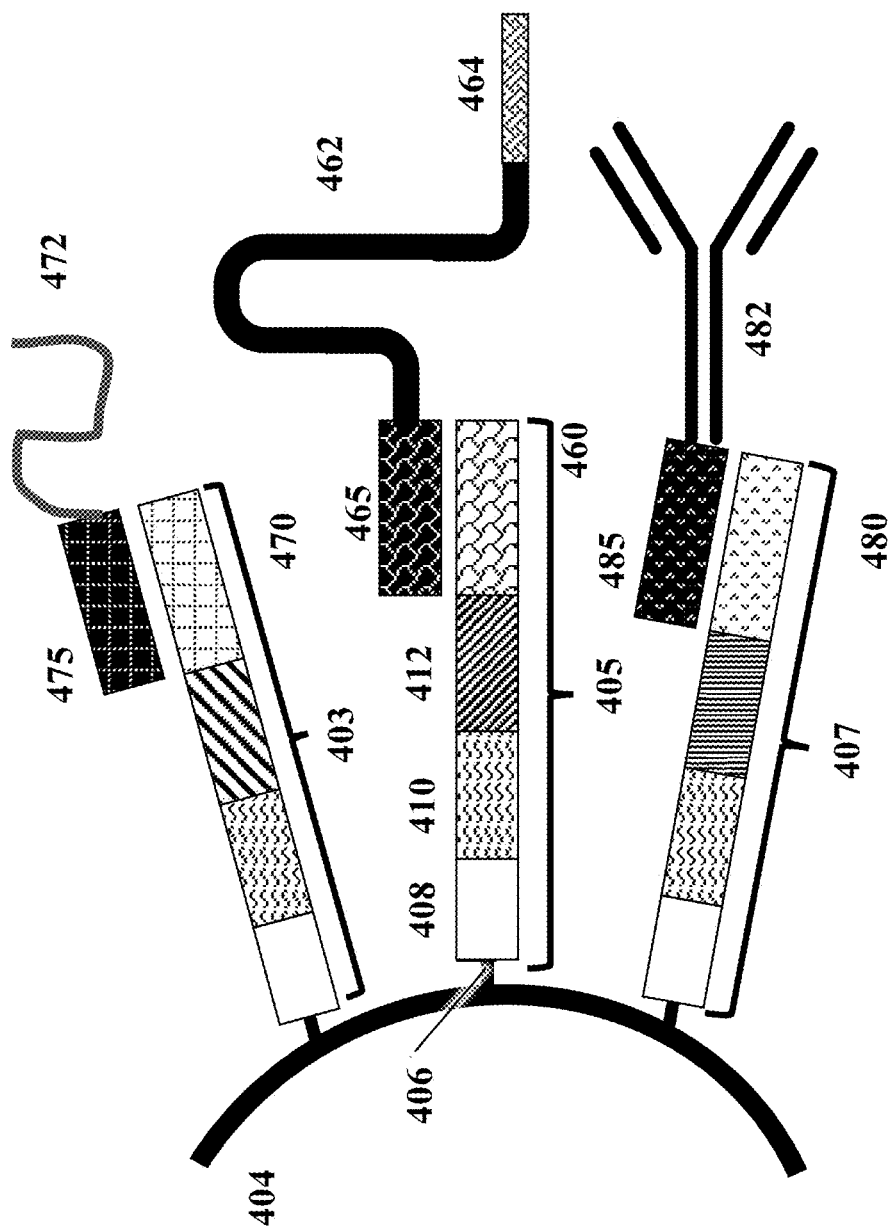
FIG. 4 illustrates another example of a barcode carrying bead

FIG. 4 illustrates another example of a barcode carrying bead. A nucleic acid molecule 405, such as an oligonucleotide, can be coupled to a bead 404 by a releasable linkage 406, such as, for example, a disulfide linker. The nucleic acid molecule 405 may comprise a first capture sequence 460. The same bead 404 may be coupled (e.g., via releasable linkage) to one or more other nucleic acid molecules 403, 407 comprising other capture sequences. The nucleic acid molecule 405 may be or comprise a barcode. As noted elsewhere herein, the structure of the barcode may comprise a number of sequence elements, such as a functional sequence 408 (e.g., flow cell attachment sequence, sequencing primer sequence, etc.), a barcode sequence 410 (e.g., bead-specific sequence common to bead, partition-specific sequence common to partition, etc.), and a unique molecular identifier 412 (e.g., unique sequence within different molecules attached to the bead), or partial sequences thereof. The capture sequence 460 may be configured to attach to a corresponding capture sequence 465. In some instances, the corresponding capture sequence 465 may be coupled to another molecule that may be an analyte or an intermediary carrier. For example, as illustrated in FIG. 4, the corresponding capture sequence 465 is coupled to a guide RNA molecule 462 comprising a target sequence 464, wherein the target sequence 464 is configured to attach to the analyte. Another oligonucleotide molecule 407 attached to the bead 404 comprises a second capture sequence 480 which is configured to attach to a second corresponding capture sequence 485. As illustrated in FIG. 4, the second corresponding capture sequence 485 is coupled to an antibody 482. In some cases, the antibody 482 may have binding specificity to an analyte (e.g., surface protein). Alternatively, the antibody 482 may not have binding specificity. Another oligonucleotide molecule 403 attached to the bead 404 comprises a third capture sequence 470 which is configured to attach to a second corresponding capture sequence 475. As illustrated in FIG. 4, the third corresponding capture sequence 475 is coupled to a molecule 472. The molecule 472 may or may not be configured to target an analyte. The other oligonucleotide molecules 403, 407 may comprise the other sequences (e.g., functional sequence, barcode sequence, UMI, etc.) described with respect to oligonucleotide molecule 405. While a single oligonucleotide molecule comprising each capture sequence is illustrated in FIG. 4, it will be appreciated that, for each capture sequence, the bead may comprise a set of one or more oligonucleotide molecules each comprising the capture sequence. For example, the bead may comprise any number of sets of one or more different capture sequences. Alternatively or in addition, the bead 404 may comprise other capture sequences. Alternatively or in addition, the bead 404 may comprise fewer types of capture sequences (e.g., two capture sequences). Alternatively or in addition, the bead 404 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmaleimide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent: gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In some cases, a species (e.g., oligonucleotide molecules comprising barcodes) that are attached to a solid support (e.g., a bead) may comprise a U-excising element that allows the species to release from the bead. In some cases, the U-excising element may comprise a single-stranded DNA (ssDNA) sequence that contains at least one uracil. The species may be attached to a solid support via the ssDNA sequence containing the at least one uracil. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about $\frac{1}{10}$th, less than about $\frac{1}{50}$th, or even less than about $\frac{1}{100}$th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may comprise pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

In some examples, a partition of the plurality of partitions may comprise a single biological particle (e.g., a single cell or a single nucleus of a cell). In some examples, a partition of the plurality of partitions may comprise multiple biological particles. Such partitions may be referred to as multiply occupied partitions, and may comprise, for example, two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction. In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition). 12971 The partitions described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Multiplexing

The present disclosures provides methods and systems for multiplexing, and otherwise increasing throughput in, analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cell features may be used to characterize biological particles and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, each of which is herein entirely incorporated by reference for all purposes.

In a particular example, a library of potential cell feature labelling agents may be provided, where the respective cell feature labelling agents are associated with nucleic acid reporter molecules, such that a different reporter oligonucleotide sequence is associated with each labelling agent capable of binding to a specific cell feature. In some aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

Labelling agents capable of binding to or otherwise coupling to one or more biological particles may be used to characterize an biological particle as belonging to a particular set of biological particles. For example, labeling agents may be used to label a sample of cells or a group of cells. In this way, a group of cells may be labeled as different from another group of cells. In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling an biological particle may comprise subjecting the antibody-linked barcode molecule or the epitope binding fragment-linked barcode molecule to conditions suitable for binding the antibody to a molecule present on a surface of the biological particle. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as partitioning and/or nucleic acid amplification or extension. A dissociation constant (Kd) between the antibody or an epitope binding fragment thereof and the molecule to which it binds may be less than about 100 µM, 90 µM, 80 µM, 70 µM, 60 µM, 50 µM, 40 µM, 30 µM, 20 µM, 10 µM, 9 µM, 8 µM, 7 µM, 6 µM, 5 µM, 4 µM, 3 µM, 2 µM, 1 µM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM 60 pM, 50 pM, 40 pM, 30 pM, 20 pM, 10 pM, 9 pM, 8 pM, 7 pM, 6 pM, 5 pM, 4 pM, 3 pM, 2 pM, or 1 pM. For example, the dissociation constant may be less than about 10 µM.

In another example, a reporter oligonucleotide may be coupled to a cell-penetrating peptide (CPP), and labeling cells may comprise delivering the CPP coupled reporter oligonucleotide into a biological particle. Labeling biological particles may comprise delivering the CPP conjugated oligonucleotide into a cell and/or cell bead by the cell-penetrating peptide. A cell-penetrating peptide that can be used in the methods provided herein can comprise at least one non-functional cysteine residue, which may be either free or derivatized to form a disulfide link with an oligonucleotide that has been modified for such linkage. Non-limiting examples of cell-penetrating peptides that can be used in embodiments herein include penetratin, transportan, plsl, TAT(48-60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The cell-penetrating peptide may be an arginine-rich peptide transporter. The cell-penetrating peptide may be Penetratin or the Tat peptide.

In another example, a reporter oligonucleotide may be coupled to a fluorophore or dye, and labeling cells may comprise subjecting the fluorophore-linked barcode molecule to conditions suitable for binding the fluorophore to the surface of the biological particle. In some instances, fluorophores can interact strongly with lipid bilayers and labeling biological particles may comprise subjecting the fluorophore-linked barcode molecule to conditions such that the fluorophore binds to or is inserted into a membrane of the biological particle. In some cases, the fluorophore is a water-soluble, organic fluorophore. In some instances, the fluorophore is Alexa 532 maleimide, tetramethylrhodamine-5-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B, Alexa 594 maleimide, Texas Red maleimide, Alexa 633 maleimide, Abberior STAR 635P azide, Atto 647N maleimide, Atto 647 SE, or Sulfo-Cy5 maleimide. See, e.g., Hughes L D, et al. PLoS One. 2014 Feb. 4; 9(2):e87649, which is hereby incorporated by reference in its entirety for all purposes, for a description of organic fluorophores.

A reporter oligonucleotide may be coupled to a lipophilic molecule, and labeling biological particles may comprise delivering the nucleic acid barcode molecule to a membrane of the biological particle or a nuclear membrane by the lipophilic molecule. Lipophilic molecules can associate with and/or insert into lipid membranes such as cell membranes and nuclear membranes. In some cases, the insertion can be reversible. In some cases, the association between the lipophilic molecule and biological particle may be such that the biological particle retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to partitioning, the cells may be incubated with the library of labelling agents, that may be labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, which is hereby entirely incorporated by reference for all purposes.

As described elsewhere herein, libraries of labelling agents may be associated with a particular cell feature as well as be used to identify analytes as originating from a particular biological particle, population, or sample. The biological particles may be incubated with a plurality of libraries and a given biological particle may comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In some instances, these reporter oligonucleotides may comprise nucleic acid barcode sequences that permit identification of the labelling agent which the reporter oligonucleotide is coupled to. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment), e.g., via a linker, using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2): 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 10:
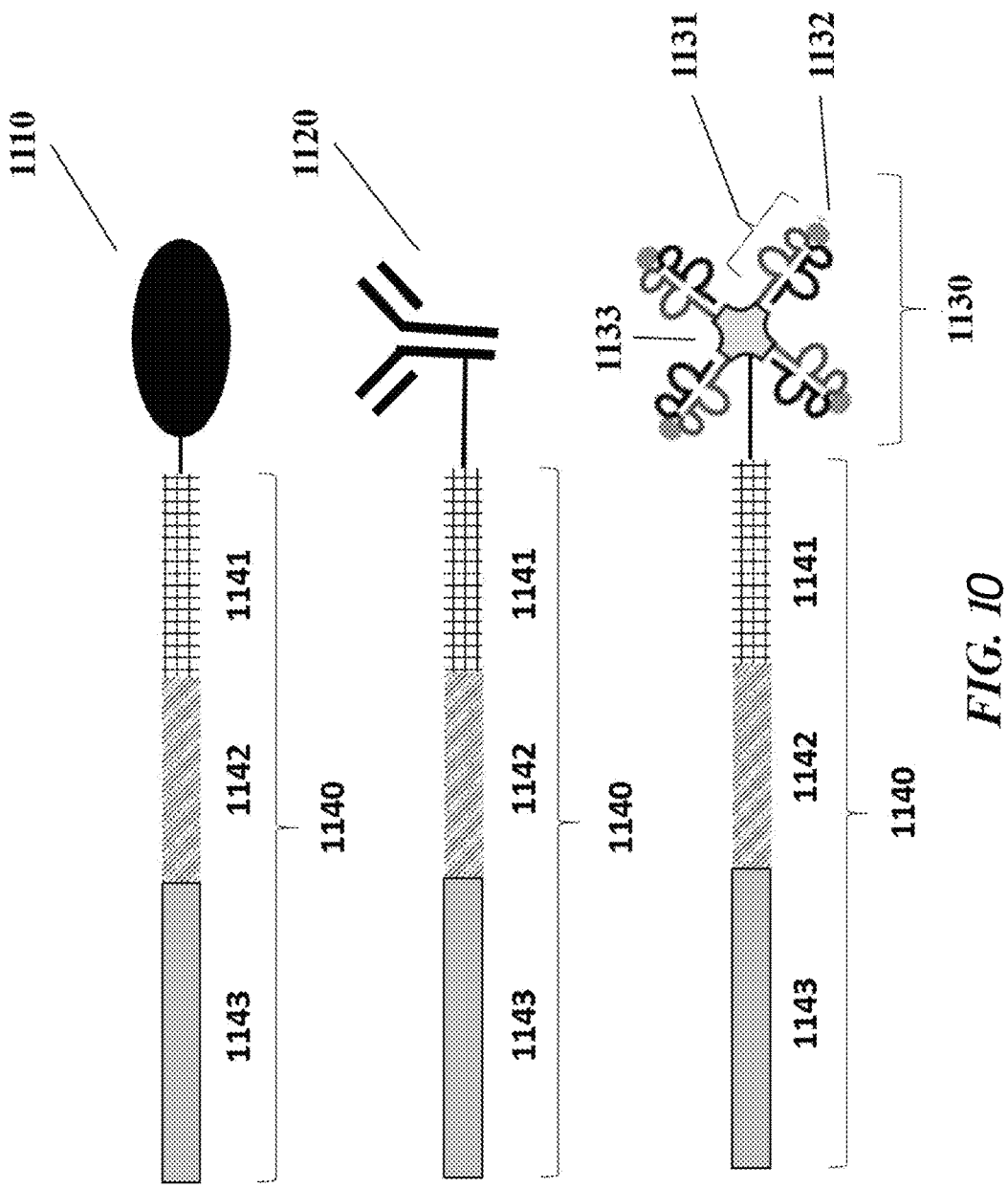
FIG. 10 schematically illustrates example labelling agents with nucleic acid molecules attached thereto.

FIG. 10 describes exemplary labelling agents (1110, 1120, 1130) comprising reporter oligonucleotides (1140) attached thereto. Labelling agent 1110 (e.g., any of the labelling agents described herein) is attached (either directly, e.g., covalently attached, or indirectly) to reporter oligonucleotide 1140. Reporter oligonucleotide 1140 may comprise barcode sequence 1142 that identifies labelling agent 1110. Reporter oligonucleotide 1140 may also comprise one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 10, in some instances, reporter oligonucleotide 1140 conjugated to a labelling agent (e.g., 1110, 1120, 1130) comprises a functional sequence 1141 (e.g., a primer sequence), a barcode sequence that identifies the labelling agent (e.g., 1110, 1120, 1130), and functional sequence 1143. Functional sequence 1143 can be a reporter capture handle sequence configured to hybridize to a complementary sequence, such as a complementary sequence present on a nucleic acid barcode molecule 1190 (not shown), such as those described elsewhere herein. In some instances, nucleic acid barcode molecule 1190 is attached to a support (e.g., a bead, such as a gel bead), such as those described elsewhere herein. For example, nucleic acid barcode molecule 1190 may be attached to the support via a releasable linkage (e.g., comprising a labile bond), such as those described elsewhere herein. In some instances, reporter oligonucleotide 1140 comprises one or more additional functional sequences, such as those described above.

In some instances, the labelling agent 1110 is a protein or polypeptide (e.g., an antigen or prospective antigen) comprising reporter oligonucleotide 1140. Reporter oligonucleotide 1140 comprises barcode sequence 1142 that identifies polypeptide 1110 and can be used to infer the presence of an analyte, e.g., a binding partner of polypeptide 1110 (i.e., a molecule or compound to which polypeptide 1110 can bind). In some instances, the labelling agent 1110 is a lipophilic moiety (e.g., cholesterol) comprising reporter oligonucleotide 1140, where the lipophilic moiety is selected such that labelling agent 1110 integrates into a membrane of a cell or nucleus. Reporter oligonucleotide 1140 comprises barcode sequence 1142 that identifies lipophilic moiety 1110 which in some instances is used to tag cells (e.g., groups of cells, cell samples, etc.) and may be used for multiplex analyses as described elsewhere herein. In some instances, the labelling agent is an antibody 1120 (or an epitope binding fragment thereof) comprising reporter oligonucleotide 1140. Reporter oligonucleotide 1140 comprises barcode sequence 1142 that identifies antibody 1120 and can be used to infer the presence of, e.g., a target of antibody 1120 (i.e., a molecule or compound to which antibody 1120 binds). In other embodiments, labelling agent 1130 comprises an MHC molecule 1131 comprising peptide 1132 and reporter oligonucleotide 1140 that identifies peptide 1132. In some instances, the MHC molecule is coupled to a support 1133. In some instances, support 1133 may be a polypeptide, such as streptavidin, or a polysaccharide, such as dextran. In some instances, reporter oligonucleotide 1140 may be directly or indirectly coupled to MHC labelling agent 1130 in any suitable manner. For example, reporter oligonucleotide 1140 may be coupled to MHC molecule 1131, support 1133, or peptide 1132. In some embodiments, labelling agent 1130 comprises a plurality of MHC molecules, (e.g. is an MHC multimer, which may be coupled to a support (e.g., 1133)). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of exemplary labelling agents, including antibody and MHC-based labelling agents, reporter oligonucleotides, and methods of use, see, e.g., U.S. Pat. No. 10,550,429 and U.S. Pat. Pub. 20190367969, each of which is herein entirely incorporated by reference for all purposes.

Figure 11C:
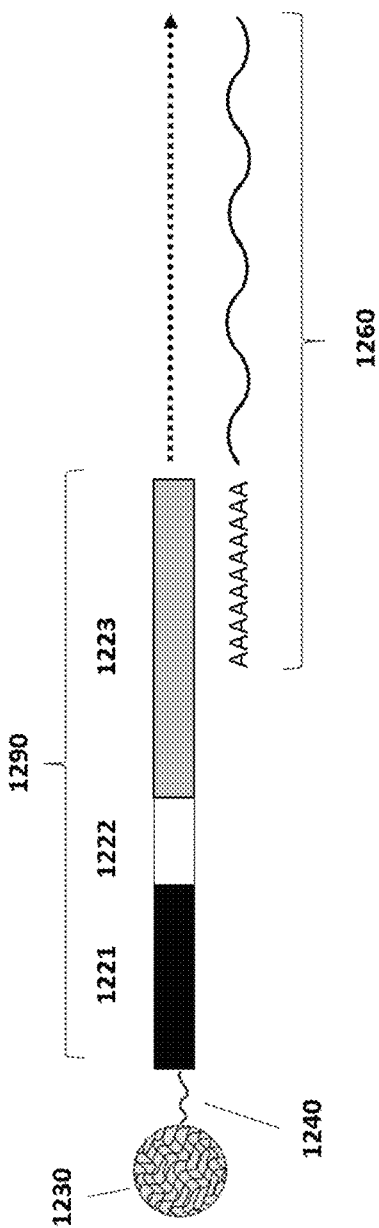
FIG. 11C schematically shows another example workflow for processing nucleic acid molecules.
Figure 12:
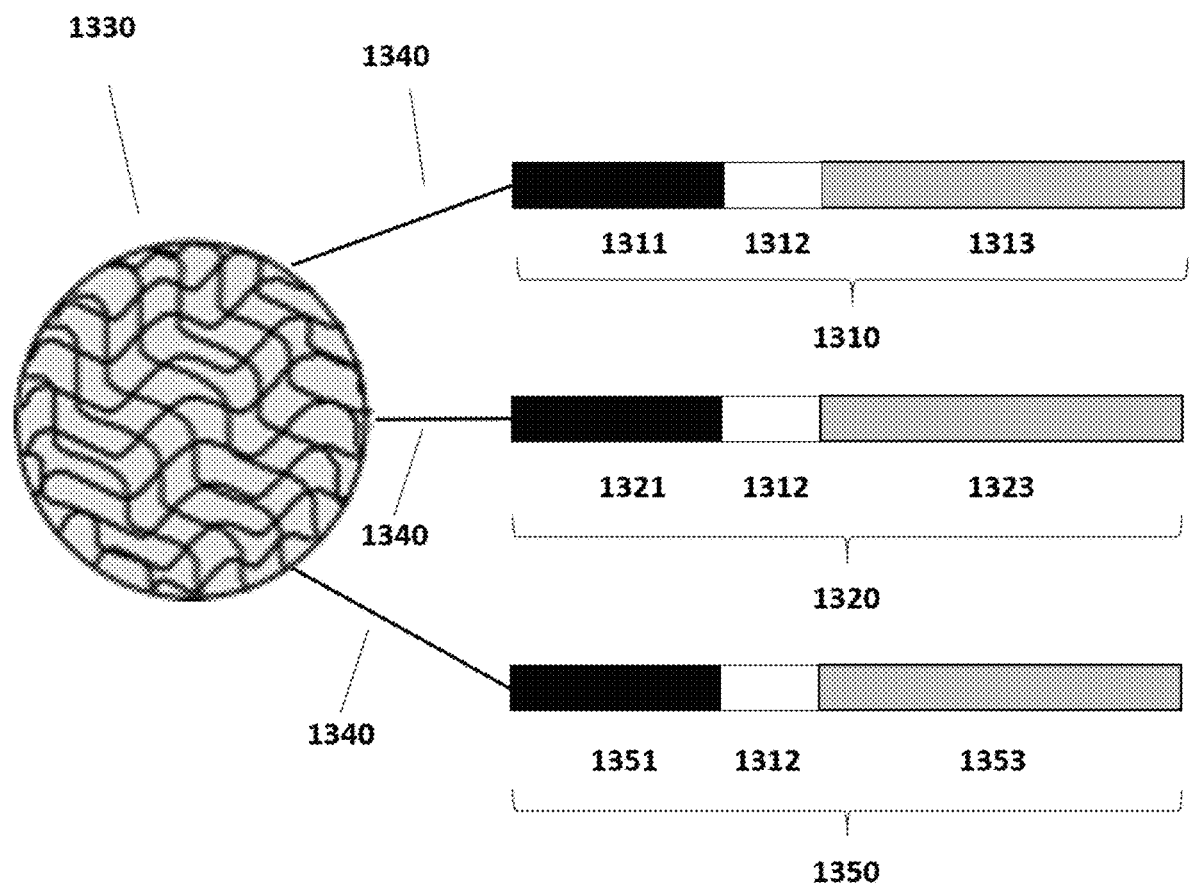
FIG. 12 schematically shows another example of a barcode-carrying bead.

FIG. 12 illustrates another example of a barcode carrying bead. In some embodiments, analysis of multiple analytes (e.g., RNA and one or more analytes using labelling agents described herein) may comprise nucleic acid barcode molecules as generally depicted in FIG. 12. In some embodiments, nucleic acid barcode molecules 1310 and 1320 are attached to support 1330 via a releasable linkage 1340 (e.g., comprising a labile bond) as described elsewhere herein. Nucleic acid barcode molecule 1310 may comprise adapter sequence 1311, barcode sequence 1312 and capture sequence 1313. Nucleic acid barcode molecule 1320 may comprise adapter sequence 1321, barcode sequence 1312, and capture sequence 1323, wherein capture sequence 1323 comprises a different sequence than capture sequence 1313. In some instances, adapter 1311 and adapter 1321 comprise the same sequence. In some instances, adapter 1311 and adapter 1321 comprise different sequences. Although support 1330 is shown comprising nucleic acid barcode molecules 1310 and 1320, any suitable number of barcode molecules comprising common barcode sequence 1312 are contemplated herein. For example, in some embodiments, support 1330 further comprises nucleic acid barcode molecule 1350. Nucleic acid barcode molecule 1350 may comprise adapter sequence 1351, barcode sequence 1312 and capture sequence 1353, wherein capture sequence 1353 comprises a different sequence than capture sequence 1313 and 1323. In some instances, nucleic acid barcode molecules (e.g., 1310, 1320, 1350) comprise one or more additional functional sequences, such as a UMI or other sequences described herein. The nucleic acid barcode molecules 1310, 1320 or 1350 may interact with analytes as described elsewhere herein, for example, as depicted in FIGS. 11A-C.

Referring to FIG. 11A, in an instance where cells are labelled with labeling agents, capture sequence 1223 may be complementary to an adapter sequence of a reporter oligonucleotide. Cells may be contacted with one or more reporter oligonucleotide 1220 conjugated labelling agents 1210 (e.g., polypeptide, antibody, or others described elsewhere herein). In some cases, the cells may be further processed prior to barcoding. For example, such processing steps may include one or more washing and/or cell sorting steps. In some instances, a cell that is bound to labelling agent 1210 which is conjugated to oligonucleotide 1220 and support 1230 (e.g., a bead, such as a gel bead) comprising nucleic acid barcode molecule 1290 is partitioned into a partition amongst a plurality of partitions (e.g., a droplet of a droplet emulsion or a well of a microwell array). In some instances, the partition comprises at most a single cell bound to labelling agent 1210. In some instances, reporter oligonucleotide 1220 conjugated to labelling agent 1210 (e.g., polypeptide, an antibody, pMHC molecule such as an MHC multimer, etc.) comprises a first adapter sequence 1211 (e.g., a primer sequence), a barcode sequence 1212 that identifies the labelling agent 1210 (e.g., the polypeptide, antibody, or peptide of a pMHC molecule or complex), and an capture handle sequence 1213. Capture handle sequence 1213 may be configured to hybridize to a complementary sequence, such as a capture sequence 1223 present on a nucleic acid barcode molecule 1290. In some instances, oligonucleotide 1220 comprises one or more additional functional sequences, such as those described elsewhere herein.

Barcoded nucleic may be generated (e.g., via a nucleic acid reaction, such as nucleic acid extension or ligation) from the constructs described in FIGS. 11A-C. For example, capture handle sequence 1213 may then be hybridized to complementary sequence, such as capture sequence 1223 to generate (e.g., via a nucleic acid reaction, such as nucleic acid extension or ligation) a barcoded nucleic acid molecule comprising cell (e.g., partition specific) barcode sequence 1222 (or a reverse complement thereof) and reporter barcode sequence 1212 (or a reverse complement thereof). In some embodiments, the nucleic acid barcode molecule 1290 (e.g., partition-specific barcode molecule) further includes a UMI (not shown). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, which is hereby entirely incorporated by reference for all purposes. Barcoded nucleic acid molecules, or derivatives generated therefrom, can then be sequenced on a suitable sequencing platform.

In some instances, analysis of multiple analytes (e.g., nucleic acids and one or more analytes using labelling agents described herein) may be performed. For example, the workflow may comprise a workflow as generally depicted in any of FIGS. 11A-C, or a combination of workflows for an individual analyte, as described elsewhere herein. For example, by using a combination of the workflows as generally depicted in FIGS. 11A-C, multiple analytes can be analyzed.

In some instances, analysis of an analyte (e.g. a nucleic acid, a polypeptide, a carbohydrate, a lipid, etc.) comprises a workflow as generally depicted in FIG. 11A. A nucleic acid barcode molecule 1290 may be co-partitioned with the one or more analytes. In some instances, nucleic acid barcode molecule 1290 is attached to a support 1230 (e.g., a bead, such as a gel bead), such as those described elsewhere herein. For example, nucleic acid barcode molecule 1290 may be attached to support 1230 via a releasable linkage 1240 (e.g., comprising a labile bond), such as those described elsewhere herein. Nucleic acid barcode molecule 1290 may comprise a functional sequence 1221 and optionally comprise other additional sequences, for example, a barcode sequence 1222 (e.g., common barcode, partition-specific barcode, or other functional sequences described elsewhere herein), and/or a UMI sequence (not shown). The nucleic acid barcode molecule 1290 may comprise a capture sequence 1223 that may be complementary to another nucleic acid sequence, such that it may hybridize to a particular sequence, e.g., capture handle sequence 1213.

For example, capture sequence 1223 may comprise a poly-T sequence and may be used to hybridize to mRNA. Referring to FIG. 11C, in some embodiments, nucleic acid barcode molecule 1290 comprises capture sequence 1223 complementary to a sequence of RNA molecule 1260 from a cell. In some instances, capture sequence 1223 comprises a sequence specific for an RNA molecule. Capture sequence 1223 may comprise a known or targeted sequence or a random sequence. In some instances, a nucleic acid extension reaction may be performed, thereby generating a barcoded nucleic acid product comprising capture sequence 1223, the functional sequence 1221, barcode sequence 1222, any other functional sequence, and a sequence corresponding to the RNA molecule 1260.

In another example, capture sequence 1223 may be complementary to an overhang sequence or an adapter sequence that has been appended to an analyte. For example, referring to FIG. 11B, panel 1201, in some embodiments, primer 1250 comprises a sequence complementary to a sequence of nucleic acid molecule 1260 (such as an RNA encoding for a BCR sequence) from an biological particle. In some instances, primer 1250 comprises one or more sequences 1251 that are not complementary to RNA molecule 1260. Sequence 1251 may be a functional sequence as described elsewhere herein, for example, an adapter sequence, a sequencing primer sequence, or a sequence the facilitates coupling to a flow cell of a sequencer. In some instances, primer 1250 comprises a poly-T sequence. In some instances, primer 1250 comprises a sequence complementary to a target sequence in an RNA molecule. In some instances, primer 1250 comprises a sequence complementary to a region of an immune molecule, such as the constant region of a TCR or BCR sequence. Primer 1250 is hybridized to nucleic acid molecule 1260 and complementary molecule 1270 is generated (see Panel 1202). For example, complementary molecule 1270 may be cDNA generated in a reverse transcription reaction. In some instances, an additional sequence may be appended to complementary molecule 1270. For example, the reverse transcriptase enzyme may be selected such that several non-templated bases 1280 (e.g., a poly-C sequence) are appended to the cDNA. In another example, a terminal transferase may also be used to append the additional sequence. Nucleic acid barcode molecule 1290 comprises a sequence 1224 complementary to the non-templated bases, and the reverse transcriptase performs a template switching reaction onto nucleic acid barcode molecule 1290 to generate a barcoded nucleic acid molecule comprising cell (e.g., partition specific) barcode sequence 1222 (or a reverse complement thereof) and a sequence of complementary molecule 1270 (or a portion thereof). In some instances, sequence 1223 comprises a sequence complementary to a region of an immune molecule, such as the constant region of a TCR or BCR sequence. Sequence 1223 is hybridized to nucleic acid molecule 1260 and a complementary molecule 1270 is generated. For example complementary molecule 1270 may be generated in a reverse transcription reaction generating a barcoded nucleic acid molecule comprising cell (e.g., partition specific) barcode sequence 1222 (or a reverse complement thereof) and a sequence of complementary molecule 1270 (or a portion thereof). Additional methods and compositions suitable for barcoding cDNA generated from mRNA transcripts including those encoding V(D)J regions of an immune cell receptor and/or barcoding methods and composition including a template switch oligonucleotide are described in International Patent Application WO2018/075693, U.S. Patent Publication No. 2018/0105808, U.S. Patent Publication No. 2015/0376609, filed Jun. 26, 2015, and U.S. Patent Publication No 2019/0367969, each of which applications is herein entirely incorporated by reference for all purposes.

The methods described herein may comprise templated ligation. A templated ligation process may comprise contacting a nucleic acid molecule (e.g., an RNA molecule) with a probe molecule. The probe molecule may interact with one or more other probe molecules, for example, comprising a barcode sequence, to generate a probe-barcode complex. An extension reaction may be performed on at least a portion of the probe-barcode complex to generate a nucleic acid product that comprises the barcode sequence and is associated with a sequence of the nucleic acid molecule. Beneficially, the methods described herein may allow barcoding of the nucleic acid molecule without performing reverse transcription on the nucleic acid molecule. The methods herein may comprise ligation-mediated reactions.

A method may comprise contacting a nucleic acid molecule (e.g., an RNA molecule) with a first probe molecule, comprising a first sequence and a second sequence, under conditions sufficient for the first sequence to hybridize to a sequence of the nucleic acid molecule. A second probe molecule comprising a third sequence may hybridize to the second sequence of the first probe molecule. The first probe or the second probe molecule may comprise a barcode sequence (e.g., as described herein). For example, the second probe molecule may be a nucleic acid molecule (e.g., as described herein). In some cases, a splint molecule may be used to link the first and second probe molecules. For example, a fourth sequence of the splint molecule may hybridize to the second sequence of the first probe molecule and a fifth sequence of the splint molecule may hybridize to the third sequence of the second probe molecule.

In another example, a first probe molecule with a first reactive moiety and a second probe molecule with a second reactive moiety may be used. A first sequence of the first probe molecule may hybridize to a first sequence of a nucleic acid molecule and a second sequence of the second probe molecule may hybridize to a second sequence of the nucleic acid molecule. The first and second sequences of the nucleic acid molecule may be adjacent or may be separated by a gap of one or more nucleotides, which gap may optionally be filled (e.g., using a polymerase). The first reactive moiety of the first probe molecule and the second reactive moiety of the second probe molecule may be subjected to conditions sufficient for the first and second reactive moieties to react to provide a linking moiety. For example, a click chemistry reaction involving an alkyne moiety and an azide moiety may be used to provide a triazole linking moiety. In other examples, an iodide moiety may be chemically ligated to a phosphorothioate moiety to form a phosphorothioate bond, an acid may be ligated to an amine to form an amide bond, or a phosphate may be ligated to an amine to form a phosphoramidate bond. In some cases, the probes may be subjected to an enzymatic ligation reaction, using a ligase, e.g., SplintR ligases, T4 ligases, KOD ligases, PBCV1 enzymes, etc. to form a probe-linked nucleic acid molecule. Where the two probes are non-adjacent, gap regions between the probes may be filled prior to ligation. In some instances, ribonucleotides or deoxyribonucleotides are ligated between the first and second probes.

Prior to, in parallel, or subsequent to linking of the first and second probe molecules (e.g., via reaction between their respective reactive moieties), a third probe molecule (e.g., a nucleic acid barcode molecule) may be subjected to conditions sufficient to hybridize to a third sequence of the first probe molecule. The third probe molecule may comprise a barcode sequence. In some cases, a splint molecule may be used to link the first and third probe molecules. In some cases, the first and second probe molecules may be linked to one another such that a loop or "padlock" is formed after hybridization of the first sequence of the first probe molecule to the first sequence of the nucleic acid molecule and the second sequence of the second probe molecule to the second sequence of the nucleic acid molecule. A linkage between the first and second probe molecules may be generated after hybridization of the first and second probe molecules to the nucleic acid molecule, such as via reaction between two reactive moieties to form a linking moiety. Alternatively, the first and second probe molecules may be linked to one another before the first and second probe molecules hybridize to the nucleic acid molecule.

All or a portion of the templated ligation processes described herein may be performed within a partition (e.g., as described herein). Alternatively, one or more such processes may be performed within a bulk solution. For example, one or more probe molecules may be subjected to conditions sufficient to hybridize to a nucleic acid molecule (e.g., a nucleic acid molecule included in an biological particle such as a cell) within a bulk solution. The nucleic acid molecule may be partitioned within various reagents (e.g., as described herein) including a nucleic acid barcode molecule, such as a nucleic acid barcode molecule releasably coupled to a bead (e.g., as described herein). Within the partition, the nucleic acid barcode molecule may hybridize to a sequence of a probe molecule hybridized to the nucleic acid molecule, thereby generated a barcode-linked nucleic acid molecule. Templated ligation processes may permit indirect barcoding of a nucleic acid molecule without the use of reverse transcription. Details of such processes and additional schemes are included in, for example, International Patent Publication No. WO2019/165318, which is herein entirely incorporated by reference for all purposes.

I. Methods, Compositions, and Systems for Spatial Analysis

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363(6434):1463-1467, 2019; Lee et al., Nat. Protoc. 10(3):442-458, 2015; Trejo et al., PLOS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev D, dated October 2020), and/or the Visium Spatial Tissue Optimization Reagent Kits User Guide (e.g., Rev D, dated October 2020), both of which are available at the 10× Genomics Support Documentation website, and can be used herein in any combination. Further non-limiting aspects of spatial analysis methodologies and compositions are described herein.

Some general terminologies that may be used in this disclosure can be found in Section (I)(b) of WO 2020/176788 and/or U.S. Patent Application Publication No. 2020/0277663.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)).

Figure 13:
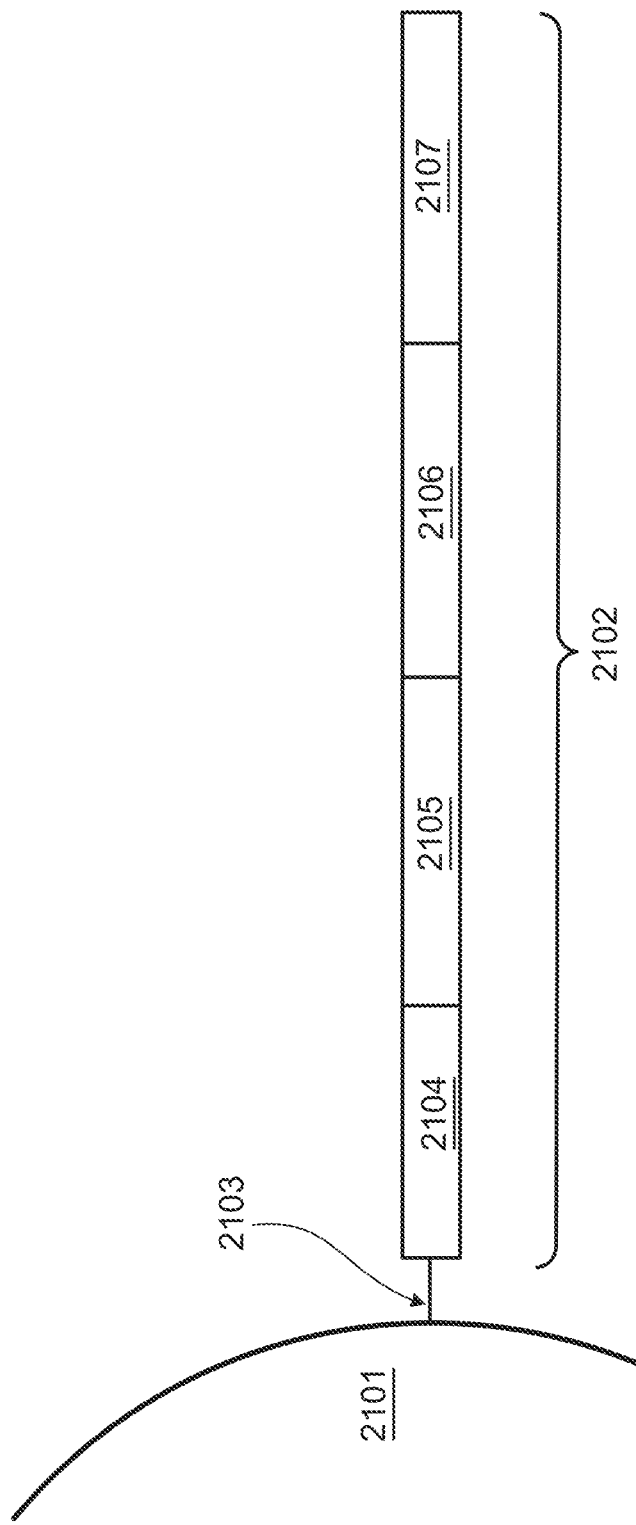
FIG. 13 is a schematic diagram showing another example of a barcoded capture probe, as described herein.

FIG. 13 is a schematic diagram showing an exemplary capture probe, as described herein. As shown, the capture probe 2102 is optionally coupled to a feature 2101 by a cleavage domain 2103, such as a disulfide linker. The capture probe can include a functional sequence 2104 that is useful for subsequent processing. The functional sequence 2104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 2105. The capture probe can also include a unique molecular identifier (UMI) sequence 2106. While FIG. 13 shows the spatial barcode 2105 as being located upstream (5') of UMI sequence 2106, it is to be understood that capture probes wherein UMI sequence 2106 is located upstream (5') of the spatial barcode 2105 is also suitable for use in any of the methods described herein. The capture probe can also include a capture domain 2107 to facilitate capture of a target analyte. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 2105 and functional sequences 2104 are common to all of the probes attached to a given feature. In some embodiments, the UMI sequence 2106 of a capture probe attached to a given feature is different from the UMI sequence of a different capture probe attached to the given feature.

Figure 14:
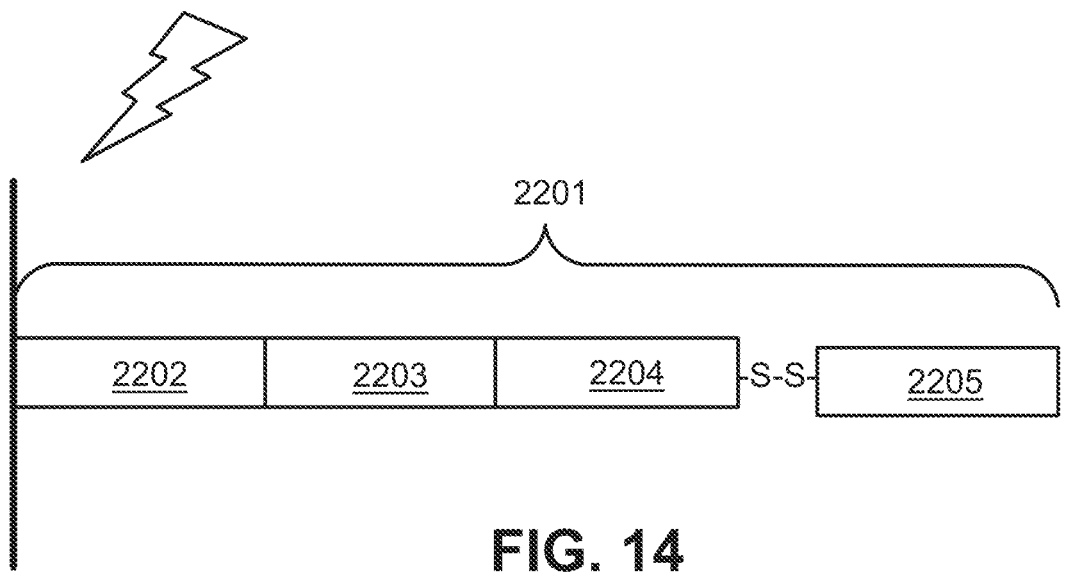
FIG. 14 is a schematic illustrating a cleavable capture probe, wherein the cleaved capture probe can enter into a non-permeabilized cell and bind to target analytes within the sample.

FIG. 14 is a schematic illustrating a cleavable capture probe, wherein the cleaved capture probe can enter into a non-permeabilized cell and bind to analytes within the sample. The capture probe 2201 contains a cleavage domain 2202, a cell penetrating peptide 2203, a reporter molecule 2204, and a disulfide bond (—S—S—). 2205 represents all other parts of a capture probe, for example a spatial barcode and a capture domain.

Figure 15:
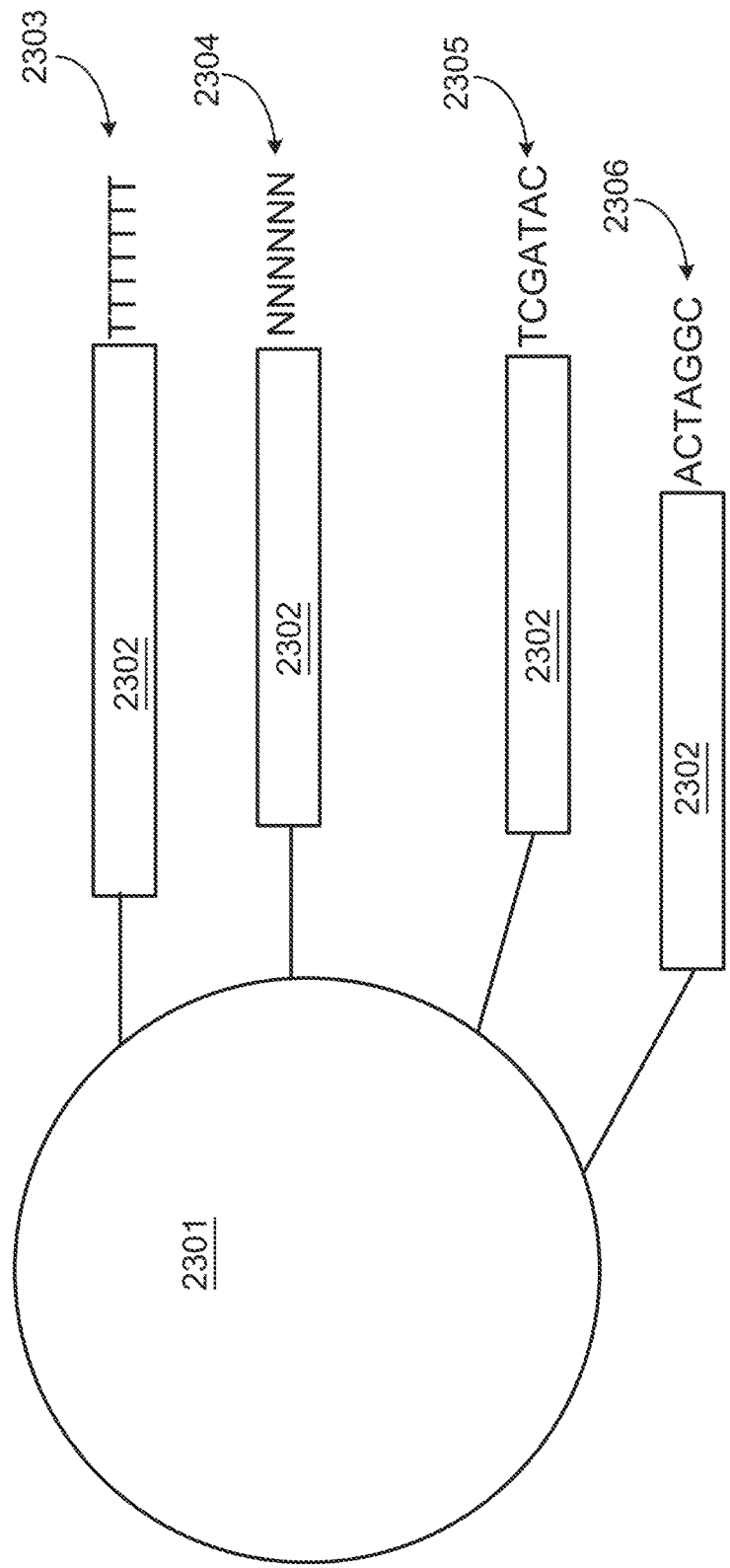
FIG. 15 is a schematic diagram of an exemplary multiplexed spatially-barcoded feature.

FIG. 15 is a schematic diagram of an exemplary multiplexed spatially-barcoded feature. In FIG. 15, the feature 2301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 2302. One type of capture probe associated with the feature includes the spatial barcode 2302 in combination with a poly(T) capture domain 2303, designed to capture mRNA target analytes. A second type of capture probe associated with the feature includes the spatial barcode 2302 in combination with a random N-mer capture domain 2304 for gDNA analysis. A third type of capture probe associated with the feature includes the spatial barcode 2302 in combination with a capture domain complementary to a capture handle sequence of an analyte capture agent of interest 2305. A fourth type of capture probe associated with the feature includes the spatial barcode 2302 in combination with a capture domain that can specifically bind a nucleic acid molecule 2306 that can function in a CRISPR assay (e.g., CRISPR/Cas9). While only four different capture probe-barcoded constructs are shown in FIG. 15, capture-probe barcoded constructs can be tailored for analyses of any given analyte associated with a nucleic acid and capable of binding with such a construct. For example, the schemes shown in FIG. 15 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(dxii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof, (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 16:
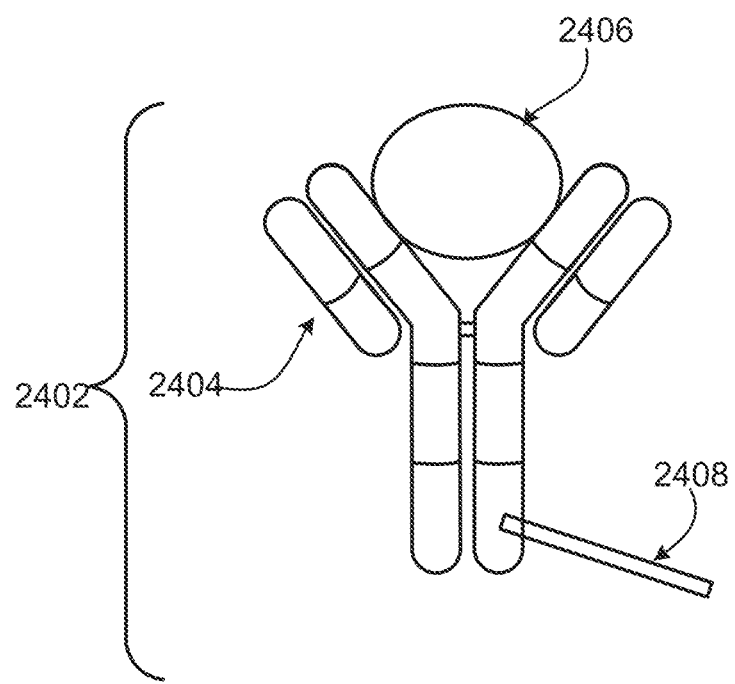
FIG. 16 is a schematic diagram of an exemplary analyte capture agent.

FIG. 16 is a schematic diagram of an exemplary analyte capture agent 2402 comprised of an analyte-binding moiety 2404 and an analyte-binding moiety barcode domain 2408. The exemplary analyte-binding moiety 2404 is a molecule capable of binding to an analyte 2406 and the analyte capture agent is capable of interacting with a spatially-barcoded capture probe. The analyte-binding moiety can bind to the analyte 2406 with high affinity and/or with high specificity. The analyte capture agent can include an analyte-binding moiety barcode domain 2408, a nucleotide sequence (e.g., an oligonucleotide), which can hybridize to at least a portion or an entirety of a capture domain of a capture probe. The analyte-binding moiety barcode domain 2408 can comprise an analyte binding moiety barcode and a capture handle sequence described herein. The analyte-binding moiety 2404 can include a polypeptide and/or an aptamer. The analyte-binding moiety 2404 can include an antibody or antibody fragment (e.g., an antigen-binding fragment).

Figure 17:
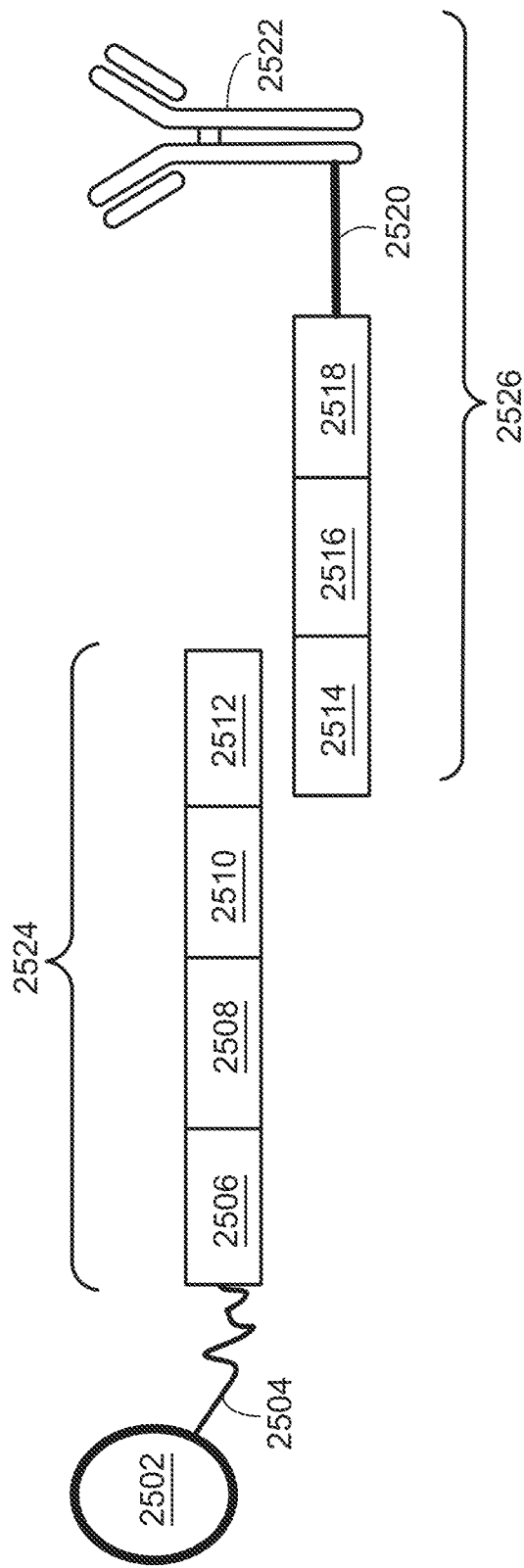
FIG. 17 is a schematic diagram depicting an exemplary interaction between a feature-immobilized capture probe 2524 and an analyte capture agent 2526.

FIG. 17 is a schematic diagram depicting an exemplary interaction between a feature-immobilized capture probe 2524 and an analyte capture agent 2526. The feature-immobilized capture probe 2524 can include a spatial barcode 2508 as well as functional sequences 2506 and UMI 2510, as described elsewhere herein. The capture probe can also include a capture domain 2512 that is capable of binding to an analyte capture agent 2526. The analyte capture agent 2526 can include a functional sequence 2518, analyte binding moiety barcode 2516, and a capture handle sequence 2514 that is capable of binding to the capture domain 2512 of the capture probe 2524. The analyte capture agent can also include a linker 2520 that allows the capture agent barcode domain 2516 to couple to the analyte binding moiety 2522.

Figure 18A:
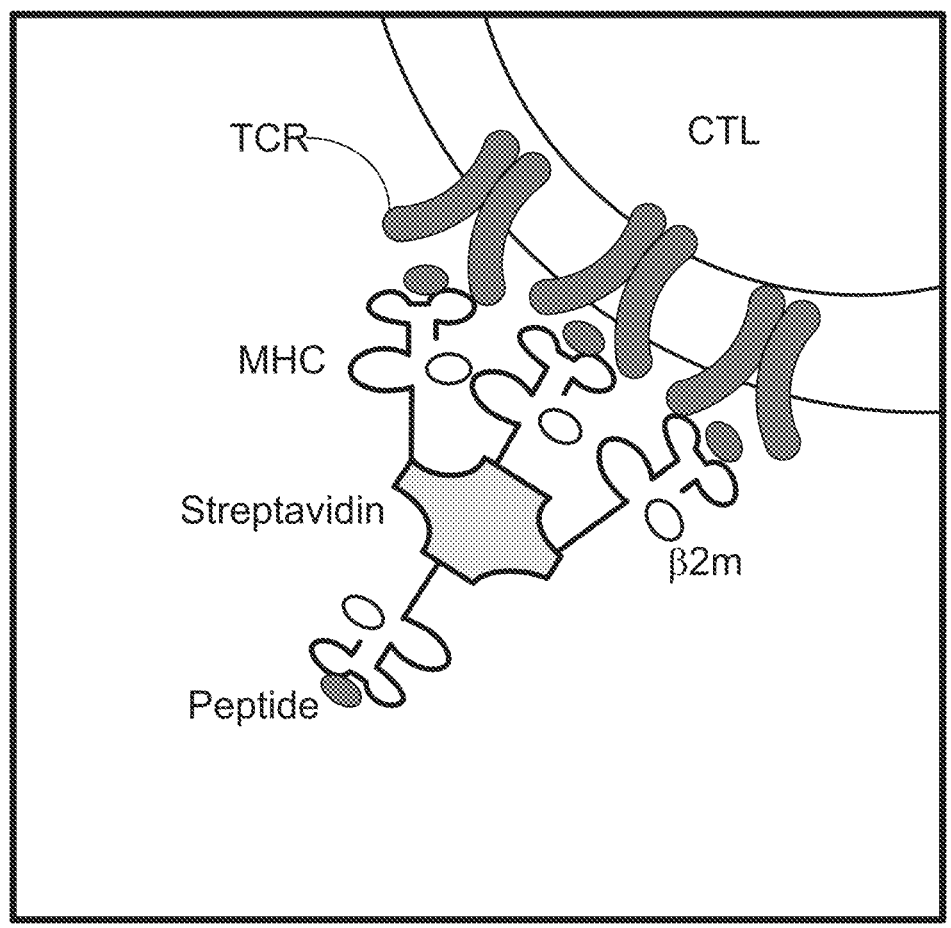
Figure 18B:
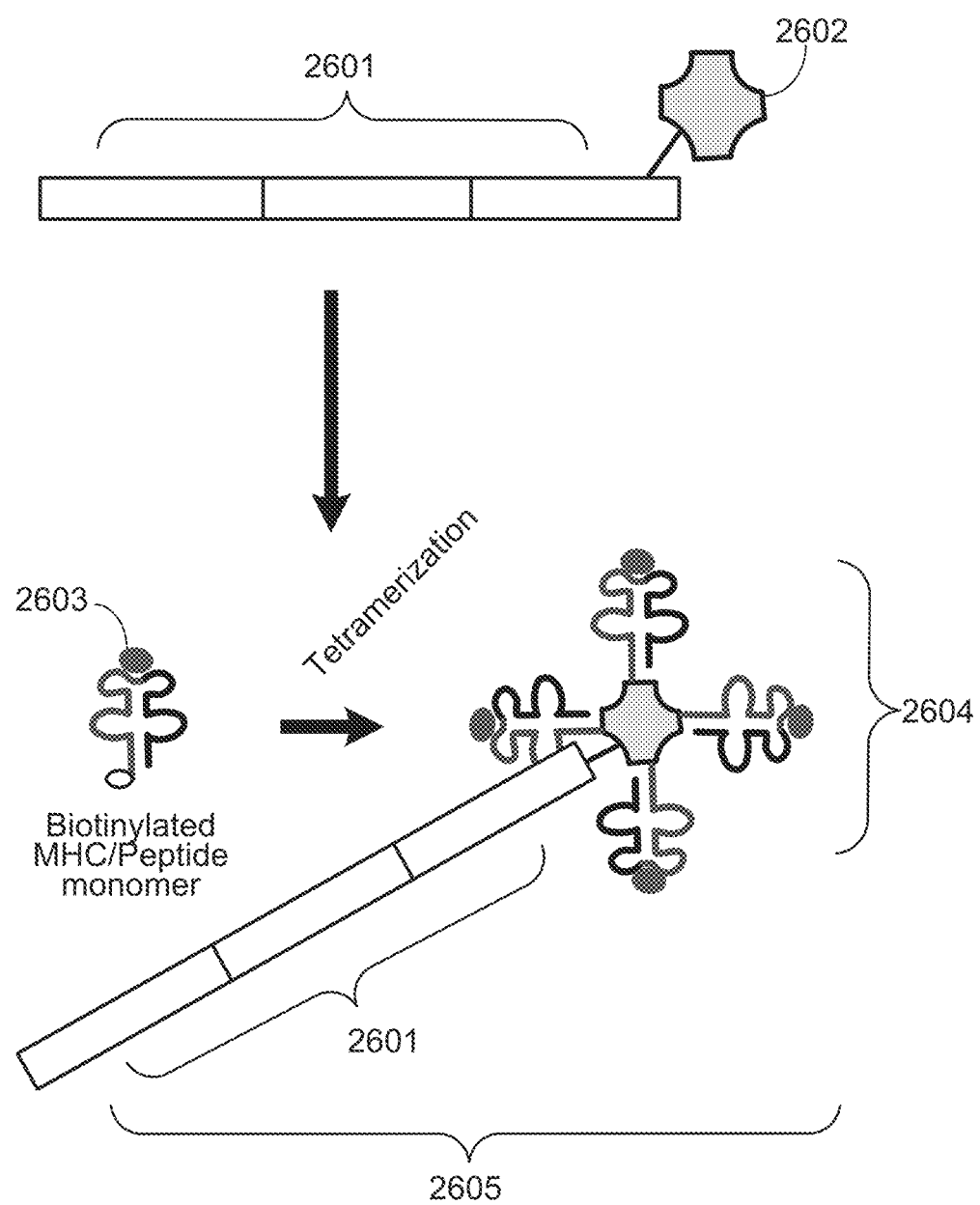

FIGS. 18A, 18B, and 18C are schematics illustrating how streptavidin cell tags can be utilized in an array-based system to produce a spatially-barcoded cell or cellular contents. For example, as shown in FIG. 18A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MHC/TCR binding interactions. Multiple interactions synergize and can substantially improve binding affinity. Such improved affinity can improve labelling of T-cells and also reduce the likelihood that labels will dissociate from T-cell surfaces. As shown in FIG. 18B, a capture agent barcode domain 2601 can be associated with streptavidin 2602 and contacted with multiple molecules of biotinylated MHC 2603 such that the biotinylated MHC 2603 molecules are coupled with the streptavidin conjugated capture agent barcode domain 2601. The result is a barcoded MHC multimer complex 2605. As shown in FIG. 18B, the capture agent barcode domain sequence 2601 can identify the MHC as its associated label and also includes optional functional sequences such as sequences for hybridization with other oligonucleotides. As shown in FIG. 18C, one example oligonucleotide is capture probe 2606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 2606 may at first be associated with a feature (e.g., a gel bead) and released from the feature. In other embodiments, capture probe 2606 can hybridize with a capture agent barcode domain 2601 of the MHC-oligonucleotide complex 2605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of the corresponding sequences may be a complement of the original sequence in capture probe 2606 or capture agent barcode domain 2601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 2606 spatial barcode sequence may be used to identify a feature and the sequence derived from spatial barcode sequence on the capture agent barcode domain 2601 may be used to identify the particular peptide MHC complex 2604 bound on the surface of the cell (e.g., when using MHC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663. 13591 In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., Nucleic Acids Res. 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a connected probe (e.g., a ligation product). In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the connected probe (e.g., a ligation product) is released from the analyte. In some instances, the connected probe (e.g., a ligation product) is released using an endonuclease. In some embodiments, the endonuclease is an RNAse. In some embodiments, the endonuclease is one of RNase A, RNase C, RNase H, and RNase I. In some embodiments, the endonuclease is RNAse H. In some embodiments, the RNase H is RNase H1 or RNase H2. The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev D, dated October 2020), and/or the Visium Spatial Tissue Optimization Reagent Kits User Guide (e.g., Rev D, dated October 2020). In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

The following examples are intended to illustrate, but not limit, the invention.

EXAMPLES

Example 1

Cell-Internal Polymer Stabilization (CIPS)

Starting from a single cell suspension, cells are pelleted and resuspended in buffer containing a triblock copolymer as described above (e.g., for about 15 minutes) to allow insertion of the copolymer in the membrane (e.g., at a temperature of about 4° C. to about 20° C.).

Cells are optionally pelleted and washed (e.g., 1-3 times) with buffer, to remove unbound copolymer from solution. However, this may not be necessary if polymerization of unbound copolymer with monomers/oligomers in solution does not affect downstream assays or procedures.

Cells are resuspended in buffered solution containing monomers/oligomers as described above (e.g., for about 5 minutes) to allow accumulation of monomers/oligomers inside the cells and formation of polymer network inside the cells (e.g., at a temperature of about 4° C. to about 20° C.).

If a bioorthogonal chemistry employing a catalyst is used, the catalyst is added to the cell suspension either with the monomer/oligomer or after the monomer/oligomer. If added after the monomer/oligomer, the cells are washed with buffer prior to the catalyst addition.

After formation of the polymer network, cells are pelleted and washed with buffer, to remove unreacted monomer/oligomer from solution. The cells are polymer-network stabilized and may be further fixed and/or frozen.

For some applications, the polymer network is dissociated prior to an application of use such as biomolecule quantitation and/or analysis. Cells are thawed, if frozen, and resuspended in media containing a depolymerization agent for a period of time sufficient to depolymerize at least a portion of the polymer network (e.g., 5 min). The cells are washed with buffer (e.g., 1-3 times) to remove depolymerized monomer/oligomer and depolymerization agent.

In some applications of use, depolymerization may not be required. For example, membrane destabilization during formation of Gel Bead-In Emulsions (GEMs) (10× Genomics Chromium system) may be sufficient to free biomolecules (e.g., RNA for reverse transcription). Alternatively, the depolymerization agent may be included in the gel beads, either during manufacturing or immediately prior to GEM generation.

Depolymerization may not be required for 10× Genomics single cell assays, as membrane destabilization during GEM generation may be sufficient to free RNA for RT.

Alternatively, a depolymerization agent can be included as part of the gel beads—so if this fixation method was used, the depolymerization agent would be added to the gel beads either during manufacturing or immediately prior to GEM generation on the Chromium system.

Tissue-Internal Polymer Stabilization (TIPS)

Tissue is harvested, and immersed in buffered solution containing a triblock copolymer as described above (e.g., for about 15 minutes) to allow insertion of the copolymer in the membrane (e.g., at a temperature of about 4° C. to about 20° C.).

The tissue is washed (e.g., 1-3 times) with buffer, to remove unbound copolymer from solution.

The tissue is immersed in buffered solution containing monomers/oligomers as described above (e.g., for about 15 minutes) to allow accumulation of monomers/oligomers inside cells of the tissue and formation of polymer network inside the cells (e.g., at a temperature of about 4° C. to about 20° C.).

If a bioorthogonal chemistry employing a catalyst is used, the catalyst is added to the tissue either with the monomer/oligomer or after the monomer/oligomer. If added after the monomer/oligomer, the tissue is washed with buffer prior to the catalyst addition.

After formation of the polymer network, the tissue is washed with buffer, to remove unreacted monomer/oligomer from solution. The cells in the tissue are polymer-network stabilized and may be further fixed. For some applications, the tissue is dissociated to generate a single cell suspension containing stabilized cells, for example, using a gentleMACS™ Dissociator (www.miltenyibiotec.com/US-en/products/gentlemacsdissociator.html#gref).

For some applications, the polymer network is dissociated prior to an application of use such as biomolecule quantitation and/or analysis, and/or spatial localization and/or quantitation within the tissue. The tissue is optionally dissociated to generate a single cell suspension containing stabilized cells. The cells are resuspended in media containing a depolymerization agent for a period of time sufficient to depolymerize at least a portion of the polymer network (e.g., 5 min). The cells are washed with buffer (e.g., 1-3 times) to remove depolymerized monomer/oligomer and depolymerization agent.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

I claim:

1. A method for stabilization of a biological particle for biomolecule analysis, comprising:
    (a) contacting a biological particle that comprises a biological particle membrane with a plurality of block copolymers, wherein the biological particle membrane comprises an intra-biological particle facing side that faces the inside of the biological particle and an extra-biological particle facing side that faces the outside of the biological particle, and
    wherein a block copolymer of the plurality of block copolymers comprises:
        (i) a hydrophobic core region comprising a first end and a second end; and
        (ii) a first hydrophilic region and a second hydrophilic region adjacent to the first end and the second end of the hydrophobic core region, respectively, wherein the first hydrophilic region comprises a bioorthogonal reactive moiety,
    wherein, upon said contacting, the block copolymer is inserted into the biological particle membrane at a first position such that (i) the hydrophobic core region is retained within the biological particle membrane, (ii) the first hydrophilic region of the block copolymer is oriented on the intra-biological particle facing side of the biological particle membrane, and
        (iii) the second hydrophilic region of the block copolymer is oriented on the extra-biological particle facing side of the biological particle membrane; and
    (b) subjecting the bioorthogonal reactive moiety of the first block copolymer to conditions sufficient to form an intra-biological particle polymer network between the bioorthogonal reactive moiety of the block copolymer and another bioorthogonal reactive moiety of another block copolymer, wherein a biomolecule of interest is retained within the biological particle and is not degraded by formation of the intra-biological particle polymer network.

2. The method of claim 1, wherein (b) comprises contacting the biological particle with a plurality of monomers or oligomers that are capable of accumulating within the biological particle, wherein a monomer or oligomer of the plurality of monomers or oligomers comprises (i) a first bioorthogonal moiety that reacts with the bioorthogonal reactive moiety of the first hydrophilic region of the block copolymer and (ii) a second bioorthogonal moiety that reacts with the first bioorthogonal moiety, and
    wherein the intra-biological particle polymer network is formed via (1) reaction of the first bioorthogonal moiety with the bioorthogonal reactive moiety of the first hydrophilic region of the block copolymer and (2) reaction of the second bioorthogonal reactive moiety of the monomer or oligomer and another first bioorthogonal moiety of another monomer or oligomer inside the biological particle.

3. The method of claim 2, wherein the second hydrophilic region of the block copolymer comprises an extra-bioorthogonal reactive moiety on the extra-biological particle facing side of the biological particle, and
    wherein (b) further comprises polymerizing the extra-bioorthogonal reactive moiety of the second hydrophilic region to form an extra-biological particle polymer network.

4. The method of claim 3, wherein polymerizing the extra-bioorthogonal reactive moiety of the second hydrophilic region to form the extra-biological particle polymer network comprises (i) reaction of the extra-bioorthogonal moiety of the second hydrophilic region with the first bioorthogonal moiety or second bioorthogonal moiety of the monomer or oligomer; and (ii) reaction of the first bioorthogonal moiety or second bioorthogonal moiety with another first bioorthogonal moiety or another second bioorthogonal moiety of another monomer or oligomer outside of the biological particle.

5. The method of claim 1, wherein the second hydrophilic region of the block copolymer comprises a membrane impermeable moiety, and wherein the second hydrophilic region of the block copolymer is oriented on the extra-biological particle side of the biological particle membrane.

6. The method of claim 5, wherein the membrane impermeable moiety comprises an affinity moiety.

7. The method of claim 6, wherein the affinity moiety comprises a member of an affinity binding pair.

8. The method of claim 6, further comprising isolating the biological particle by contacting the biological particle with a molecule that binds to the affinity moiety.

9. The method of claim 5, wherein the membrane impermeable moiety comprises a detectable label.

10. The method of claim 1, wherein the biomolecule of interest is a nucleic acid, a protein, a lipid, or a carbohydrate.

11. The method of claim 10, wherein the biomolecule of interest is ribonucleic acid (RNA), and wherein the method further comprises reverse transcribing the RNA.

12. The method of claim 1, comprising:
    (c) contacting the biological particle with a fixative to stabilize architecture of the biological particle.

13. The method of claim 12, wherein the fixative comprises paraformaldehyde, formalin, methanol, hypothermisol, or RNAlater.

14. The method of claim 1, wherein the hydrophobic core region of the block copolymer comprises poly(propylene oxide).

15. The method of claim 1, wherein the first hydrophilic region or the second hydrophilic region of the block copolymer comprises poly(ethylene oxide).

16. The method of claim 1, wherein the bioorthogonal reactive moiety of the first hydrophilic region of the block copolymer comprises an alkyne group or an azide group.

17. The method of claim 1, further comprising:
    (d) depolymerizing the intra-biological particle polymer network; and
    (e) determining presence, absence, quantity, or spatial location of the biomolecule of interest in the biological particle or in a biological sample from which the biological particle is derived.

18. The method of claim 1, further comprising isolating the biological particle from a biological sample prior to (a) or after (b).

19. The method of claim 1, further comprising:
    (c) determining presence, absence, quantity, or spatial location of the biomolecule of interest in a biological sample from which the biological particle is derived.

20. The method of claim 1, wherein said biological particle comprises a cell or an organelle.

21. The method of claim 1, wherein the conditions sufficient to form the intra-biological particle polymer network comprise (1) providing a bioorthogonal reactive moiety subject to ring strain or (2) providing a catalyst to the bioorthogonal reactive moiety and the another bioorthogonal reactive moiety.

22. The method of claim 1, wherein the bioorthogonal reactive moiety is selected from the group consisting of an alkyne, an azide, a phosphine, a cyclooctyne, a nitrone, a norbornene, an oxanorbornadiene, a tetrazine, an isocyanide, a tetrazole, a quadricyclane, and a nitrile imine.

\* \* \* \* \*